(12) United States Patent
Bhatia et al.

(10) Patent No.: US 11,428,689 B2
(45) Date of Patent: Aug. 30, 2022

(54) METHODS AND USES FOR REMOTELY TRIGGERED PROTEASE ACTIVITY MEASUREMENTS

(71) Applicant: Massachusetts Institute of Technology, Cambridge, MA (US)

(72) Inventors: Sangeeta N. Bhatia, Lexington, MA (US); Gabriel A. Kwong, Atlanta, GA (US); Piyush K. Jain, Somerville, MA (US); Jaideep S. Dudani, Boston, MA (US); Simone Schurle, Zurich (CH)

(73) Assignee: Massachusetts Institute of Technology, Cambridge, MA (US)

( * ) Notice: Subject to any disclaimer, the term of this patent is extended or adjusted under 35 U.S.C. 154(b) by 758 days.

(21) Appl. No.: 16/099,147

(22) PCT Filed: May 5, 2017

(86) PCT No.: PCT/US2017/031401
§ 371 (c)(1),
(2) Date: Nov. 5, 2018

(87) PCT Pub. No.: WO2017/193070
PCT Pub. Date: Nov. 9, 2017

(65) Prior Publication Data
US 2019/0144917 A1    May 16, 2019

Related U.S. Application Data

(60) Provisional application No. 62/332,096, filed on May 5, 2016.

(51) Int. Cl.
*G01N 33/68* (2006.01)
*G01N 33/58* (2006.01)
(Continued)

(52) U.S. Cl.
CPC ......... *G01N 33/54346* (2013.01); *C12Q 1/37* (2013.01); *G01N 33/58* (2013.01);
(Continued)

(58) Field of Classification Search
CPC ........... G01N 33/54346; G01N 33/587; G01N 33/58; G01N 33/68
See application file for complete search history.

(56) References Cited

U.S. PATENT DOCUMENTS

| 5,500,161 A | 3/1996 | Andrianov et al. |
| 5,811,252 A | 9/1998 | Verheijen |

(Continued)

FOREIGN PATENT DOCUMENTS

| CN | 102558362 A | 7/2012 |
| CN | 103012595 A | 4/2013 |

(Continued)

OTHER PUBLICATIONS

Kulkarni et al. MMP-9 Responsive PEG Cleavable Nanovesicles for Efficient Delivery of Chemotherapeutics to Pancreatic Cancer. Mol. Pharmaceutics 11: 2390-2399 (2014).*

(Continued)

*Primary Examiner* — Gailene Gabel
(74) *Attorney, Agent, or Firm* — Wolf, Greenfield & Sacks, P.C.

(57) ABSTRACT

The present disclosure relates to methods and products associated with in vitro and in vivo protease activity measurements and enzyme profiling. Some aspects of the present disclosure relate to measuring remotely triggered protease activity. In particular, the disclosure relates to methods of in vivo processing of exogenous molecules followed by detection of signature molecules as representative of the presence or absence of active enzymes associated with disease or conditions. The disclosure also relates to prod- (Continued)

ucts, kits, and databases for use in the methods of the disclosure.

9 Claims, 36 Drawing Sheets

Specification includes a Sequence Listing.

(51) Int. Cl.
  G01N 33/543 (2006.01)
  C12Q 1/37 (2006.01)
  B82Y 15/00 (2011.01)
  B82Y 5/00 (2011.01)
(52) U.S. Cl.
  CPC ........... *G01N 33/587* (2013.01); *G01N 33/68* (2013.01); *B82Y 5/00* (2013.01); *B82Y 15/00* (2013.01); *C12Y 304/21014* (2013.01)

(56) References Cited

U.S. PATENT DOCUMENTS

| | | |
|---|---|---|
| 5,885,775 A | 3/1999 | Haff et al. |
| 6,312,390 B1 | 11/2001 | Phillips |
| 6,335,429 B1 | 1/2002 | Cai et al. |
| 6,592,847 B1 | 7/2003 | Weissleder et al. |
| 6,597,996 B1 | 7/2003 | Venkataraman et al. |
| 6,629,040 B1 | 9/2003 | Goodlett et al. |
| 6,824,981 B2 | 11/2004 | Chait et al. |
| 7,041,453 B2 | 5/2006 | Yang |
| 7,169,892 B2 | 1/2007 | Atsushi et al. |
| 7,179,655 B2 | 2/2007 | Patricelli |
| 7,329,506 B2 | 2/2008 | William |
| 7,412,332 B1 | 8/2008 | Venkataraman et al. |
| 7,456,269 B2 | 11/2008 | Gurney et al. |
| 7,468,258 B2 | 12/2008 | Owen |
| 7,544,518 B2 | 6/2009 | Aebersold et al. |
| 7,595,155 B2 | 9/2009 | Murakami |
| 7,879,574 B2 | 2/2011 | Packard et al. |
| 7,985,401 B2 | 7/2011 | Jiang et al. |
| 8,673,267 B2 | 3/2014 | Bhatia et al. |
| 8,841,085 B2 | 9/2014 | Kwon et al. |
| 8,969,027 B2 | 3/2015 | Bossmann et al. |
| 9,006,415 B2 | 4/2015 | Ren et al. |
| 9,072,792 B2 | 7/2015 | Jiang et al. |
| 9,155,471 B2 | 10/2015 | Lee et al. |
| 9,657,326 B2 | 5/2017 | Ruether et al. |
| 9,808,532 B2 | 11/2017 | Tsien et al. |
| 9,913,917 B2 | 3/2018 | Groves et al. |
| 9,970,941 B2 | 5/2018 | Bhatia et al. |
| 10,006,916 B2 | 6/2018 | Kwong et al. |
| 10,527,619 B2 | 1/2020 | Bhatia et al. |
| 10,883,998 B2* | 1/2021 | Bhatia ................... C12Q 1/37 |
| 11,054,428 B2 | 7/2021 | Bhatia et al. |
| 2002/0119490 A1 | 8/2002 | Aebersold et al. |
| 2003/0059952 A1 | 3/2003 | Chait et al. |
| 2004/0014652 A1 | 1/2004 | Dubois et al. |
| 2004/0091943 A1 | 5/2004 | Schneider |
| 2005/0107583 A1 | 5/2005 | Jiang et al. |
| 2005/0260695 A1 | 11/2005 | Fleming et al. |
| 2006/0008856 A1 | 1/2006 | Singh et al. |
| 2006/0257883 A1 | 11/2006 | Bjoraker et al. |
| 2006/0292631 A1 | 12/2006 | Broberg et al. |
| 2007/0010433 A1 | 1/2007 | Albrechtsen et al. |
| 2007/0048752 A1 | 3/2007 | Yan et al. |
| 2007/0207555 A1 | 9/2007 | Guerra et al. |
| 2008/0026480 A1 | 1/2008 | Guerra |
| 2008/0064607 A1 | 3/2008 | Yang |
| 2008/0095758 A1 | 4/2008 | Lee et al. |
| 2008/0113875 A1 | 5/2008 | Chaurand et al. |
| 2008/0213377 A1 | 9/2008 | Bhatia et al. |
| 2008/0226562 A1 | 9/2008 | Groves et al. |
| 2008/0241955 A1 | 10/2008 | Purkayastha et al. |
| 2008/0253960 A1 | 10/2008 | Zheng et al. |
| 2009/0016988 A1 | 1/2009 | Buckley |
| 2009/0088332 A1 | 4/2009 | Ju et al. |
| 2009/0156424 A1 | 6/2009 | Thompson |
| 2009/0230300 A1 | 9/2009 | Trevejo et al. |
| 2009/0246142 A1 | 10/2009 | Bhatia et al. |
| 2009/0252677 A1 | 10/2009 | Bogyo et al. |
| 2010/0022408 A1 | 1/2010 | Singh et al. |
| 2010/0124757 A1 | 5/2010 | Kwon et al. |
| 2010/0190193 A1 | 7/2010 | Calatzis et al. |
| 2010/0240050 A1 | 9/2010 | Bhatia et al. |
| 2010/0317542 A1 | 12/2010 | Lim et al. |
| 2011/0014125 A1 | 1/2011 | Bossmann et al. |
| 2011/0021908 A1 | 1/2011 | Lee et al. |
| 2011/0104052 A1 | 5/2011 | Barnett et al. |
| 2011/0104071 A1 | 5/2011 | Lee et al. |
| 2012/0039990 A1 | 2/2012 | Reshetnyak et al. |
| 2012/0150164 A1 | 6/2012 | Lee et al. |
| 2013/0078188 A1 | 3/2013 | Tsein et al. |
| 2013/0295129 A1 | 11/2013 | Irvine et al. |
| 2013/0315906 A1 | 11/2013 | Lowman et al. |
| 2014/0207129 A1 | 7/2014 | Lee |
| 2014/0234431 A1* | 8/2014 | Bhatia ................... C12Q 1/37 |
| | | 424/491 |
| 2014/0255313 A1 | 9/2014 | Vasiljeva et al. |
| 2014/0276102 A1 | 9/2014 | Lee et al. |
| 2014/0276103 A1 | 9/2014 | Lee et al. |
| 2014/0301950 A1 | 10/2014 | Lee et al. |
| 2014/0303014 A1 | 10/2014 | Kwong et al. |
| 2014/0363833 A1 | 12/2014 | Bhatia et al. |
| 2014/0364368 A1* | 12/2014 | Lin ......................... A61P 7/02 |
| | | 514/14.9 |
| 2015/0051153 A1 | 2/2015 | Reshetnyak et al. |
| 2015/0080721 A1 | 3/2015 | Novak et al. |
| 2015/0104381 A1 | 4/2015 | Maina-Nock et al. |
| 2015/0165062 A1 | 6/2015 | Liao et al. |
| 2016/0025632 A1 | 1/2016 | Lee et al. |
| 2016/0096869 A1 | 4/2016 | Hansen et al. |
| 2016/0184459 A1 | 6/2016 | Ueki et al. |
| 2016/0289324 A1 | 10/2016 | Moore et al. |
| 2016/0317037 A1 | 11/2016 | Lee et al. |
| 2017/0267727 A1 | 9/2017 | Thevenin et al. |
| 2017/0305968 A1 | 10/2017 | Tsein et al. |
| 2018/0021090 A1 | 1/2018 | Lee et al. |
| 2018/0196058 A1 | 7/2018 | Kwong et al. |
| 2018/0328941 A1 | 11/2018 | Bhatia et al. |
| 2018/0335429 A1 | 11/2018 | Bhatia et al. |
| 2019/0076081 A1 | 3/2019 | Hyde et al. |
| 2019/0128873 A1 | 5/2019 | Bhatia et al. |
| 2019/0212291 A1 | 7/2019 | Dudani et al. |
| 2019/0271704 A1 | 9/2019 | Bhatia et al. |
| 2019/0345534 A1 | 11/2019 | Kwong et al. |
| 2019/0376113 A1 | 12/2019 | Kwong et al. |
| 2020/0096514 A1 | 3/2020 | Bhatia et al. |
| 2020/0116725 A1 | 4/2020 | Bhatia et al. |
| 2020/0225231 A1 | 7/2020 | Bhatia et al. |
| 2020/0232986 A1 | 7/2020 | Bhatia et al. |
| 2020/0249194 A9 | 8/2020 | Dudani et al. |
| 2021/0148926 A1 | 5/2021 | Bhatia et al. |
| 2021/0262025 A1 | 8/2021 | Bhatia et al. |

FOREIGN PATENT DOCUMENTS

| | | |
|---|---|---|
| CN | 108484847 A | 9/2018 |
| JP | 2004-506900 | 3/2004 |
| JP | 2004-129651 | 4/2004 |
| JP | 2007-24631 A2 | 2/2007 |
| JP | 2007-206054 A | 8/2007 |
| JP | 2009-108037 | 5/2009 |
| JP | 2009-524688 | 7/2009 |
| JP | 2009-538430 A | 11/2009 |
| JP | 2013-060452 | 4/2013 |
| JP | 2016-520327 | 7/2016 |
| WO | WO 2002/014867 A2 | 2/2002 |
| WO | WO 2006/034370 A2 | 3/2006 |
| WO | WO 2007/060921 A1 | 5/2007 |
| WO | WO 2007/072070 A1 | 6/2007 |
| WO | WO 2008/072676 A1 | 6/2008 |
| WO | WO 2008/093513 A1 | 8/2008 |
| WO | WO 2008/127019 A1 | 10/2008 |
| WO | WO 2009/124265 A1 | 10/2009 |

(56) References Cited

FOREIGN PATENT DOCUMENTS

| | | |
|---|---|---|
| WO | WO 2010/101628 A2 | 9/2010 |
| WO | WO 2011/008996 A2 | 1/2011 |
| WO | WO 2012/031250 A2 | 3/2012 |
| WO | WO 2012/085080 A1 | 6/2012 |
| WO | WO 2012/125808 A1 | 9/2012 |
| WO | WO 2014/107599 A2 | 7/2014 |
| WO | WO 2014/120619 A2 | 8/2014 |
| WO | WO 2014/120974 A1 | 8/2014 |
| WO | WO 2014/176284 A1 | 10/2014 |
| WO | WO 2014/197816 | 12/2014 |
| WO | WO 2014/197840 A1 | 12/2014 |
| WO | WO 2015/042202 A1 | 3/2015 |
| WO | WO 2017/044894 A2 | 3/2017 |
| WO | WO 2017/120410 A1 | 7/2017 |
| WO | WO 2017/177115 A1 | 10/2017 |
| WO | WO 2017/180789 A2 | 10/2017 |
| WO | WO 2017/181149 A1 | 10/2017 |
| WO | WO 2018/049285 A1 | 3/2018 |
| WO | WO 2018/064383 A1 | 4/2018 |
| WO | WO 2018/187688 A1 | 10/2018 |
| WO | WO 2018/227132 A1 | 12/2018 |
| WO | WO 2019/071051 A1 | 4/2019 |
| WO | WO 2019/075292 A1 | 4/2019 |
| WO | WO 2019/089804 A1 | 5/2019 |
| WO | WO 2019/089820 A1 | 5/2019 |
| WO | WO 2019/126577 A2 | 6/2019 |
| WO | WO 2019/126716 A1 | 6/2019 |
| WO | WO 2019/126762 A2 | 6/2019 |
| WO | WO 2019/148206 A1 | 8/2019 |

OTHER PUBLICATIONS

Welser et al. Protease responsive nanoprobes with tethered fluorogenic peptidyl 3-arylcoumarin substrates. Chem. Commun. 671-673 (2009).*
McCarter et al. Substrate Specificity of the *Escherichia coli* Outer Membrane Protease OmpT. Journal of Bacteriology 186 (17): 5919-5925 (Sep. 2004).*
Extended European Search Report for EP 17793501.2 dated Oct. 11, 2019.
[No Author Listed] Summary for peptidase S01.010: granzyme B. MEROPS. Retrieved from <https://www.ebi.ac.uk/merops/cgi-bin/pepsum?id=S01.010;type=P>. Apr. 26, 2019. 2 pages.
[No Author Listed] Summary for peptidase S01.135: granzyme A. MEROPS. Retrieved from <https://www.ebi.ac.uk/merops/cgi-bin/pepsum?id=S01.135;type=P>. Apr. 26, 2019. 2 pages.
[No Author Listed] Summary for peptidase S01.146: granzyme K. MEROPS. Retrieved from <https://www.ebi.ac.uk/merops/cgi-bin/pepsum?id=S01.146;type=P>. Apr. 26, 2019. 2 pages.
[No Author Listed], DQ™ Gelatin From Pig Skin, Fluorescein Conjugate—Special Packaging. ThermoFisher Scientific. Enzchek® Gelatinase/Collagenase Assay Kit Product Information Sheet. Accessed on Jul. 14, 2020. Retrieved from: <https://www.thermofisher.com/order/catalog/product/D12054#/D12054>. 4 pages.
Aalipour et al., Engineered immune cells as highly sensitive cancer diagnostics. Nat Biotechnol. 2019;37:531-9.
Acharige et al., Breath-based diagnosis of fungal infections. J Breath Res. Feb. 6, 2018;12(2):027108. doi: 10.1088/1752-7163/aa98a1.
Amstad et al., Photo- and thermoresponsive polymersomes for triggered release. Angew Chem Int Ed. 2012;51:1-6.
Bartlett, Diagnostic tests for agents of community-acquired pneumonia. Clin Infect Dis. May 2011;52 Suppl 4:S296-304. doi: 10.1093/cid/cir045.
Bascomb et al., Use of Enzyme Tests in Characterization and Identification of Aerobic and Facultatively Anaerobic Gram-Positive Cocci. Clin Microbiol Rev. Apr. 1998; 11(2): 318-340.
Beauchamp et al., Real-time breath gas analysis for pharmacokinetics: monitoring exhaled breath by on-line proton-transfer-reaction mass spectrometry after ingestion of eucalyptol-containing capsules. J Breath Res. Jun. 2010;4(2):026006. doi: 10.1088/1752-7155/4/2/026006. Epub Apr. 22, 2010.
Berger, Helicobacter pylori breath tests. BMJ. 2002;324:1263.
Bonomi et al., Detection of enzyme activity through catalytic signal amplification with functionalized gold nanoparticles. Angew Chem Int Ed. 2011;50:2307-12.
Buss et al., Protease activity sensors noninvasively classify bacterial infections and antibiotic responses. EBioMedicine. Dec. 2018;38:248-56. doi:10.1016/j.ebiom.2018.11.031.
Caliendo et al., Better Tests, Better Care: Improved Diagnostics for Infectious Diseases. Clin Infect Dis. Dec. 2013;57(3):S139-S170.
Castillo et al., Sensitive substrates for human leukocyte and porcine pancreatic elastase: A study of the merits of various chromophoric and fluorogenic leaving groups in assays for serine proteases. Anal Biochem. Oct. 1979;99(1):53-64.
Chan et al., Engineering synthetic breath biomarkers for respiratory disease. Nature Nanotechnol. Jul. 20, 2020;15:792-800.
Chan et al., Inhalable Nanosensors for Rapid Breath-Based Pathogen Identification in Respiratory Infection. Revolutions in Biotechnology. MIT. Presented Mar. 5-6, 2018 at Tang Center, MIT Campus. 1 page.
Chen et al., CRISPR-Cas12a target binding unleashes indiscriminate single-stranded DNase activity. Science. Apr. 27, 2018;360(6387):436-439. Erratum in: Science. Feb. 19, 2021;371(6531): 1-4.
Cheng et al., Multifunctional nanoparticles: Cost versus benefit of adding targeting and imaging capabilities. Sci. Nov. 16, 2012;338(6109):903-10.
Cheng et al., Ultrasensitive scanometric strategy for detection of matrix metalloproteinases using a histidine tagged peptide—Au nanoparticle probe. Chem Commun. 2011;47:2877-9.
Coelho et al., Usefulness of C-reactive protein in monitoring the severe community-acquired pneumonia clinical course. Crit Care. Aug. 2007; 11(4):R92.
Cohen et al., Detection and localization of surgically resectable cancers with a multi-analyte blood test. Science. 2018;3247(80):1-10.
Danino et al., Programmable probiotics for detection of cancer in urine. Sci Transl Med. May 27, 2015;7(289):289ra84. doi: 10.1126/scitranslmed.aaa3519. PMID: 26019220; PMCID: PMC4511399.
El Badrawy et al., Matrix Metalloproteinase-9 Expression in Lung Cancer Patients and Its Relation to Serum MMP-9 Activity, Pathologic Type, and Prognosis. J Bronchol Interven Pulmonol. Oct. 2014; 21(4):327-34. doi: 10.1097/LBR.0000000000000094.
Elegbede et al., Mechanistic studies of the triggered release of liposomal contents by matrix metalloproteinase-9. J Am Chem Soc. Aug. 13, 2008;130(32):10633-42. doi: 10.1021/ja801548g. Epub Jul. 22, 2008.
Elston et al., New continuous and specific fluorometric assays for Pseudomonas aeruginosa elastase and LasA protease. Anal Biochem. Sep. 2007;368(1):87-94.
Farwell et al., PET/CT imaging in cancer: current applications and future directions. Cancer. Nov. 15, 2014;120(22):3433-45. doi: 10.1002/cncr.28860. Epub Jun. 19, 2014. PMID: 24947987.
Fernandez et al., Volatile Biomarkers in Breath Associated With Liver Cirrhosis—Comparisons of Pre- and Post-liver Transplant Breath Samples. EBIOM. 2015;2:1243-50.
Figueiredo et al., Near infrared thoracoscopy of tumoral protease activity for improved detection of peripheral lung cancer. Int J Cancer. Jun. 2006;118(11):2672-7. doi: 10.1002/ijc.21713.
Gaieska et al., Impact of time to antibiotics on survival in patients with severe sepsis or septic shock in whom early goal-directed therapy was initiated in the emergency department. Crit Care Med. Apr. 2010;38(4):1045-53. doi: 10.1097/CCM.0b013e3181cc4824.
Galati et al., Increased resistance of peptides to serum proteases by modification of their amino groups. Resist peptides against serum proteases. Jan. 8, 2003;58:558-61.
Ghoshal et al., How to Interpret Hydrogen Breath Tests. J Neurogastroenterol Motil. 2011;17:312-7.
Gootenberg et al., Multiplexed and portable nucleic acid detection platform with Cas13, Cas12a, and Csm6. Science. Apr. 27, 2018;360(6387):439-444. doi: 10.1126/science.aaq0179. Epub Feb. 15, 2018.

(56) References Cited

OTHER PUBLICATIONS

Guimaraes et al., Site-specific C-terminal internal loop labeling of proteins using sortase-mediated reactions. Nat Protoc. 2013;8:1787-99.

Haiko et al., The omptins of Yersinia pestis and *Salmonella enterica* cleave the reactive center loop of plasminogen activator inhibitor 1. J Bacteriol. Sep. 2010;192(18):4553-61. doi: 10.1128/JB.00458-10. Epub Jul. 16, 2010.

Harris et al., Protease-triggered unveiling of bioactive nanoparticles. Small. 2008;4(9):1307-12. doi: 10.1002/smll.200701319. Epub Aug. 8, 2008.

Haskins, The application of stable isotopes in biomedical research. Biomed Mass Spectrom. Jul. 1982;9(7):269-77.

Heaney et al., Real-time monitoring of exhaled volatiles using atmospheric pressure chemical ionization on a compact mass spectrometer. Bioanalysis. Jul. 2016;8(13):1325-36. doi: 10.4155/bio-2016-0045. Epub Jun. 9, 2016.

Herbig et al., Towards standardization in the analysis of breath gas volatiles. J Breath Res. 2014;8:1-11.

Holliday et al., Rapid Identification of *Staphylococcus aureus* by Using Fluorescent Staphylocoagulase Assays. J Clin Microbiol. Apr. 1999;37(4):1190-2.

Iwasaki et al., Control of adaptive immunity by the innate immune system. Nat Immunol. Mar. 19, 2015;16(4):343-53.

Janzen et al., Colorimetric sensor arrays for volatile organic compounds. Anal Chem. Jun. 1, 2006;78(11):3591-600.

Jiang et al., Tumor imaging by means of proteolytic activation of cell-penetrating peptides. Proc. Natl. Acad. Sci. U. S. A. 2004;101:17867-17872.

Johnson et al., Active-site gating regulates substrate selectivity in a chymotrypsin-like serine protease the structure of haemophilus influenzae immunoglobulin A1 protease. J Mol Biol. Jun. 12, 2009;389(3):559-74. doi: 10.1016/j.jmb.2009.04.041. Epub Apr. 23, 2009.

Kalinska et al., Substrate specificity of *Staphylococcus aureus* cysteine proteases— Staphopains A, B and C. Biochimie. Feb. 2012;94(2):318-27. doi: 10.1016/j.biochi.2011.07.020. Epub Jul. 23, 2011.

Kaman et al., Evaluation of a FRET-Peptide Substrate to Predict Virulence in Pseudomonas aeruginosa. PLoS One; Nov. 2013;8(11):e81428.

Kasperkiewicz et al., Design of ultrasensitive probes for human neutrophil elastase through hybrid combinatorial substrate library profiling. PNAS. 2014;111:2518-23.

Kim et al., Applications of stable, nonradioactive isotope tracers in in vivo human metabolic research. Exp Mol Med. Jan. 2016; 48(1): e203. Epub Jan. 15, 2016. doi: 10.1038/emm.2015.97.

Kirkpatrick et al., Noninvasive lung cancer detection via pulmonary protease profiling. bioRxiv. 36 pages. doi: https://doi.org/10.1101/495259, (2018).

Krebs et al., Molecular analysis of circulating tumour cells—biology and biomarkers. Nat Rev Clin Oncol. 2014;11:129-44.

Krilaviciute et al., Detection of cancer through exhaled breath : a systematic review Literature search. Oncotarget. 2015;6:38643-57.

Kulkarni et al., MMP-9 Responsive PEG Cleavable Nano vesicles for Efficient Delivery of Chemotherapeutics to Pancreatic Cancer. Mol Pharm. Jul. 7, 2014; 11(7): 2390-2399. doi: 10.1021/mp500108p.

Kwak et al., Volatile disease biomarkers in breath: a critique. Curr Pharm Biotechnol; 2011;12:1067-74.

Kwon et al., Porous Silicon Nanoparticle Delivery of Tandem Peptide Anti-Infectives for the Treatment of Pseudomonas aeruginosa Lung Infections. Adv Mat. Sep. 20, 2017;29(35). 21pages.

Laupland et al., The changing culture of the microbiology laboratory. Can J Infect Dis Med Microbiol. 2013 Autumn; 24(3):125-128. doi: 10.1155/2013/101630.

Liou et al., Nonisotropic Enzyme-Inhibitor Interactions: A Novel Nonoxidative Mechanism for Quantum Proteolysis by Human Neutrophils. Biochem. 1995;34(49):16171-7.

Liu et al., Structure-based programming of lymph-node targeting in molecular vaccines. Nature. Mar. 27, 2014;507(7493):519-22. doi: 10.1038/nature12978. Epub Feb. 16, 2014.

Longo et al., In Vivo Imaging of Tumor Metabolism and Acidosis by Combining PET and MRI-CEST pH Imaging. Cancer Res. Nov. 15, 2016;76(22):6463-6470. doi: 10.1158/0008-5472.CAN-16-0825. Epub Sep. 20, 2016. PMID: 27651313.

Loynachan et al., ANYL 234: Catalytic nanomaterials for amplified biosensing. Abstract of Papers, 256th National Meeting & Exposition of the ACS. ACS National Meeting & Exposition. Aug. 19, 2018. 1 page.

Matsumoto et al., Role of bacterial proteases in pseudomonal and serratial keratitis. Biol Chem. Jan. 2004;385(11):1007-16.

McCarter et al., Substrate Specificity of the *Escherichia coli* Outer Membrane Protease OmpT. J Bacteriol. Sep. 2004; 186(17): 5919-5925. doi: 10.1128/JB.186.17.5919-5925.2004.

Meyer et al., Respiratory protease / antiprotease balance determines susceptibility to viral infection and can be modified by nutritional antioxidants. Am J Physiol Lung Cell Mol Physiol. 2015;308:L1189-L1201.

Morihara, Pseudolysin and other pathogen endopeptidases of thermolysin family. Methods in Enzymol. 1995;248:242-53.

Murray, What Is New in Clinical Microbiology—Microbial Identification by MALDI-TOF Mass Spectrometry. JMDI. 2012;14:419-23.

Nizio et al., In vitro volatile organic compound profiling using GCxGC-TOFMS to differentiate bacteria associated with lung infections: a proof-of-concept study. J Breath Res. Apr. 27, 2016;10:026008, 12 pages.

Nouh et al., Cathepsin B: a potential prognostic marker for inflammatory breast cancer. J Transl Med. 2011;9(1):8 pages.

Olson et al., In vivo characterization of activatable cell penetrating peptides for targeting protease activity in cancer. Integr Biol (Camb). Jun. 2009; 1(5-6):382-93.

Ong et al., Inhalable nanosensors for rapid breath-based pathogen identification in respiratory infection. Adv Res Technol Symp. Mar. 5, 2018. 102 pages.

Ong et al., Use of Mass Spectrometric Vapor Analysis To Improve Canine Explosive Detection Efficiency. Anal Chem. 2017;89:6482-90.

Parks et al., Matrix metalloproteinases as modulators of inflammation and innate immunity. Nat Rev Immunol. Aug. 2004;4(8):617-29.

Patton et al., Inhaling medicines: delivering drugs to the body through the lungs. Nat Rev Drug Discov. Jan. 2007;6(1):67-74.

Patton et al., The lungs as a portal of entry for systemic drug delivery. Proc Am Thorac Soc. 2004;1(4):338-44.

Phillips et al., Variation in volatile organic compounds in the breath of normal humans. J Chromatogr B. 1999;729:75-88.

Potempa et al., Corruption of innate immunity by bacterial proteases. J Innate Immun. 2009;1(2):70-87.

Rashidian et al., Noninvasive imaging of immune responses. Proc Natl Acad Sci U S A. May 12, 2015;112(19):6146-51. doi: 10.1073/pnas.1502609112. Epub Apr. 20, 2015. Erratum in: Proc Natl Acad Sci U S A. Jul. 3, 2018;115(27):E6387. PMID: 25902531; PMCID: PMC4434737.

Rashidian et al., Predicting the response to CTLA-4 blockade by longitudinal noninvasive monitoring of CD8 T cells. J Exp Med. Aug. 7, 2017;214(8):2243-2255. doi: 10.1084/jem.20161950. Epub Jun. 30, 2017. PMID: 28666979; PMCID: PMC5551571.

Rawlings et al., The MEROPS database of proteolytic enzymes, their substrates and inhibitors in 2017 and a comparison with peptidases in the PANTHER database. Nucleic Acid Res. Jan. 4, 2018;46(D1):D624-D632.

Ross et al., Volatile compounds in blood headspace and nasal breath. J Breath Res. Sep. 13, 2017;11(4):046001. doi: 10.1088/1752-7163/aa7d10.

Rousalova et al., Granzyme B-induced apoptosis in cancer cells and its regulation (review). Int J Oncol. Dec. 2010;37(6):1361-78. doi: 10.3892/ijo_00000788. PMID: 21042704.

Roy et al., Matrix metalloproteinases as novel biomarkers and potential therapeutic targets in human cancer. J Clin Oncol. 2009;27:5287-97.

(56) References Cited

OTHER PUBLICATIONS

Schmid et al., Albumin-binding prodrugs of camptothecin and doxorubicin with an ala-leu-ala-leu-linker that are cleaved by cathepsin b: synthesis and antitumor efficacy. Bioconj Chem. 2007;18(3):702-16.

Sethi et al., Clinical application of volatile organic compound analysis for detecting infectious diseases. Clin Microbiol Rev. Jul. 2013;26(3):462-75. doi: 10.1128/CMR.00020-13.

Shaw et al., The role and regulation of the extracellular proteases of *Staphylococcus aureus*. Microbiol. Jan. 2004;150:217-28. doi: 10.1099/mic.0.26634-0.

Shibuya et al., Pseudomonas aeruginosa alkaline proteinase might share a biological function with plasmin. Biochim Biophys Acta. Apr. 29, 1991; 1077(3):316-24.

Stach et al., Unique Substrate Specificity of SplE Serine Protease from *Staphylococcus aureus*. Structure. Apr. 3, 2018;26(4):572-579. e4. doi: 10.1016/j.str.2018.02.008. Epub Mar. 8, 2018.

Sun et al., A PET imaging approach for determining EGFR mutation status for improved lung cancer patient management. Sci Transl Med. Mar. 7, 2018;10(431):eaan8840. doi: 10.1126/scitranslmed. aan8840. PMID: 29515002.

Sweeney et al., Robust classification of bacterial and viral infections via integrated host gene expression diagnostics. Sci Transl Med. Jul. 2016;8(346):346ra91.

Thomassin et al., OmpT Outer Membrane Proteases of Enterohemorrhagic and Enteropathogenic *Escherichia coli* Contribute Differently to the Degradation of Human LL-37. Infect Immun. Feb. 2012; 80(2): 483-492. doi: 10.1128/IAI.05674-11.

Trapani et al., Killing by cytotoxic T cells and natural killer cells: multiple granule serine proteases as initiators of DNA fragmentation. Immunol Cell Biol. 1993;71(3):201-8.

Van Der Schee et al., Breathomics in lung disease. Chest. 2015;147:224-31.

Vandooren et al., Zymography Methods for Visualizing Hydrolytic Enzymes. Nat Methods. Mar. 2013;10(3):211-20. doi: 10.1038/nmeth.2371.

Vasiljeva et al., Monitoring protease activity in biological tissues using antibody prodrugs as sensing probes. Sci Rep. Apr. 3, 2020;10(1):5894.

Vessillier et al., Hydrolysis of glycine-containing elastin pentapeptides by LasA, a metalloelastase from Pseudomonas aeruginosa. Eur J Biochem. Feb. 2001;268(4):1049-57.

Wang et al., Intrinsic enzyme mimicking activity of gold nanoclusters upon visible light triggering and its application for colorimetric trypsin detection. Biosens Bioelectronics. 2015;64:523-9. Epub Sep. 30, 2014.

Warren et al., Disease detection by ultrasensitive quantification of microdosed synthetic urinary biomarkers. J Am Chem Soc. 2014;136:13709-14.

Warren et al., Harnessing protease activity to improve cancer care. Annual Rev Cancer Biol. 2018;2:353-76.

Weerakkody et al., Family of pH (low) insertion peptides for tumor targeting. Proc Natl Acad Sci U S A. Apr. 9, 2013;110(15):5834-9. doi: 10.1073/pnas.1303708110. Epub Mar. 25, 2013. PMID: 23530249; PMCID: PMC3625278.

Wildeboer et al., Characterization of bacterial proteases with a panel of fluorescent peptide substrates. Anal Biochem. Jan. 15, 2009;384(2):321-8. doi: 10.1016/j.ab.2008.10.004. Epub Oct. 11, 2008.

Wilkinson et al., Ventilator-Associated Pneumonia Is Characterized by Excessive Release of Neutrophil Proteases in the Lung. Chest. Dec. 2012;142(6):1425-32.

Wilson et al., Applications and Advances in Electronic-Nose Technologies. Sensors (Basel). 2009;9(7):5099-148. doi: 10.3390/s90705099. Epub Jun. 29, 2009.

Wu et al., Expression and clinical significance of matrix metalloproteinase-9 in lymphatic invasiveness and metastasis of breast cancer. PLOS ONE. 2014;9(5):e97804.

Yan et al., In Situ Zymography: A Molecular Pathology Technique to Localize Endogenous Protease Activity in Tissue Sections. Vet Pathol May 2003;40(3):227-36.

Zheng et al., Dual-reaction triggered sensitivity amplification for ultrasensitive peptide-cleavage based electrochemical detection of matrix metalloproteinase-7. Biosens Bioelectronics. 2018;103:46-52. Epub Feb. 21, 2018.

Zhou et al., Thermo-sensitive microgels supported gold nanoparticles as temperature-mediated catalyst. Chinese J Polym Sci. 2019;37:235-42. Epub Aug. 30, 2018.

Zhu et al., Detecting bacterial lung infections: in vivo evaluation of in vitro volatile fingerprints. J Breath Res. Jan. 10, 2013;7(1):016003, 7 pages.

Zinnhardt et al., Combined PET Imaging of the Inflammatory Tumor Microenvironment Identifies Margins of Unique Radiotracer Uptake. Cancer Res. Apr. 15, 2017;77(8):1831-1841. doi: 10.1158/0008-5472.CAN-16-2628. Epub Jan. 30, 2017. PMID: 28137769.

Zumla et al., Rapid point of care diagnostic tests for viral and bacterial respiratory tract infections-needs, advances, and future prospects. Lancet Infect Dis. 2014;14(11):1123-35.

U.S. Appl. No. 16/159,340, filed Oct. 12, 2018, Dudani et al.

U.S. Appl. No. 16/091,145, filed Oct. 4, 2018, Bhatia et al.

PCT/US2017/031401, Jul. 3, 2017, International Search Report and Written Opinion.

PCT/US2017/031401, Nov. 15, 2018, International Preliminary Report on Patentability.

Abrahamson et al., Isolation of six cysteine proteinase inhibitors from human urine. Their physicochemical and enzyme kinetic properties and concentrations in biological fluids. J Biol Chem. Aug. 25, 1986;261(24):11282-9.

Abudayyeh, Nanoparticle-Chaperoned Urinary "Synthetic Biomarkers" for Profiling Proteases in Cancer. Thesis. Department of Mechanical Engineering. Jun. 2012.

Anderson et al., Mass spectrometric quantitation of peptides and proteins using Stable Isotope Standards and Capture by Anti-Peptide Antibodies (SISCAPA). J Proteome Res. Mar.-Apr. 2004;3(2):235-44.

Asai et al., A colorimetric assay for plasma antithrombin III using a new synthetic peptide substrate (PS-915). Clin Chim Acta. Dec. 29, 1984;144(2-3):163-71.

Baruch et al., Enzyme activity—it's all about image. Trends Cell Biol. Jan. 2004;14(1):29-35.

Becker et al., Thrombin: Structure, Biochemistry, Measurement, and Status in Clinical Medicine. J Thromb Thrombolysis. Jul. 1998;5(3):215-229.

Blum et al., Noninvasive optical imaging of cysteine protease activity using fluorescently quenched activity-based probes. Nat Chem Biol. Oct. 2007;3(10):668-77. Epub Sep. 9, 2007.

Böhm et al., uPA/PAI-1 ratios distinguish benign prostatic hyperplasia and prostate cancer. J Cancer Res Clin Oncol. Jul. 2013;139(7):1221-8. doi: 10.1007/s00432-013-1428-y. Epub Apr. 18, 2013.

Bounameaux et al., Plasma measurement of D-dimer as diagnostic aid in suspected venous thromboembolism: an overview. Thromb Haemost. Jan. 1994;71(1):1-6.

Chen et al., A unique substrate recognition profile for matrix metalloproteinase-2. J Biol Chem. Feb. 8, 2002;277(6):4485-91.

Daniel et al., Implantable diagnostic device for cancer monitoring. Biosens Bioelectron. Jul. 15, 2009;24(11):3252-7. Epub Apr. 16, 2009.

De La Rica et al., Enzyme-responsive nanoparticles for drug release and diagnostics. Adv Drug Deliv Rev. Aug. 2012;64(11):967-78. doi: 10.1016/j.addr.2012.01.002. Epub Jan. 14, 2012.

Deng et al., Gold nanoparticles based molecular beacons for in vitro and in vivo detection of the matriptase expression on tumor. Biosens Bioelectron. Nov. 15, 2013;49:216-21. doi: 10.1016/j.bios.2013.05. 018. Epub May 25, 2013.

Dennis et al., Albumin binding as a general strategy for improving the pharmacokinetics of proteins. J Biol Chem. Sep. 20, 2002;277(38):35035-43. Epub Jul. 15, 2002.

Deshpande et al., Current trends in the use of liposomes for tumor targeting. Nanomedicine (Lond). Sep. 2013;8(9):1509-28. doi:10.2217/nnm.13.118.

(56) References Cited

OTHER PUBLICATIONS

Dranoff, Cytokines in cancer pathogenesis and cancer therapy. Nat Rev Cancer. Jan. 2004;4(1):11-22.
D'Souza et al., A strategy for blood biomarker amplification and localization using ultrasound. Proc Natl Acad Sci U S A. Oct. 6, 2009;106(40):17152-7. doi: 10.1073/pnas.0903437106. Epub Sep. 23, 2009.
Dudani et al., Classification of prostate cancer using a protease activity nanosensor library. Proc Natl Acad Sci U S A. Sep. 4, 2018;115(36):8954-8959. doi: 10.1073/pnas.1805337115. Epub Aug. 20, 2018.
Dudani et al., Harnessing Protease Activity to Improve Cancer Care. Ann Rev Cancer Biol. Mar. 2018;2:353-376.
Dudani et al., Photoactivated Spatiotemporally-Responsive Nanosensors of in Vivo Protease Activity. ACS Nano. Dec. 22, 2015;9(12):11708-17. doi: 10.1021/acsnano.5b05946. Epub Nov. 13, 2015.
Dudani et al., Sustained-release synthetic biomarkers for monitoring thrombosis and inflammation using point-of-care compatible readouts. Adv Funct Mater. May 3, 2016;26(17):2919-2928. doi: 10.1002/adfm.201505142. Epub Mar. 22, 2016.
Farrell et al., Non-motor parkinsonian pathology in aging A53T α-synuclein mice is associated with progressive synucleinopathy and altered enzymatic function. J Neurochem. Feb. 2014;128(4):536-46. doi: 10.1111/jnc.12481. Epub Nov. 20, 2013.
Fowlkes et al., Proteolysis of insulin-like growth factor binding protein-3 during rat pregnancy: a role for matrix metalloproteinases. Endocrinology. Dec. 1994;135(6):2810-3.
Fusaro et al., Prediction of high-responding peptides for targeted protein assays by mass spectrometry. Nat Biotechnol. Feb. 2009;27(2):190-8. doi: 10.1038/nbt.1524. Epub Jan. 25, 2009.
Gartrell et al., Managing bone metastases and reducing skeletal related events in prostate cancer. Nat Rev Clin Oncol. Jun. 2014;11(6):335-45. doi: 10.1038/nrclinonc.2014.70. Epub May 13, 2014. Review. Erratum in: Nat Rev Clin Oncol. Jan. 2015;12(1). doi:10.1038/nrclinonc.2014.70.
Genbank Submission; NIH/NCBI, Accession No. 2WV1_A; Kovalevskiy et al.; Mar. 24, 2010.
Genbank Submission; NIH/NCBI, Accession No. CAG01641; Mar. 17, 2004.
Genbank Submission; NIH/NCBI, Accession No. NP_731669; Hoskins et al.; Dec. 18, 2009.
Genbank Submission; NIH/NCBI, Accession No. NP_938673; Cerdeno-Tarraga et al.; Jun. 3, 2010.
Genbank Submission; NIH/NCBI, Accession No. XP_001385378; Jeffries et al.; Apr. 11, 2008.
Genbank Submission; NIH/NCBI, Accession No. XP_002097000; Clark et al.; Aug. 12, 2009.
Genbank Submission; NIH/NCBI, Accession No. XP_00234527.; Jul. 7, 2006.
Genbank Submission; NIH/NCBI, Accession No. ZP_03507634; Gonzalez et al.; Dec. 19, 2008.
Genbank Submission; NIH/NCBI, Accession No. ZP_06431346; Small et al.; Jun. 9, 2010.
Ghadiali, James E. et al., "Enzyme-Responsive Nanoparticle Systems," Advanced Materials, vol. 20(22):4359-4363 (2008).
Giljohann, et al., Drivers of biodiagnostic development. Nature. Nov. 26, 2009;462(7272):461-4. doi: 10.1038/nature08605.
Ginsberg et al., Sensitivity and specificity of a rapid whole-blood assay for D-dimer in the diagnosis of pulmonary embolism. Ann Intern Med. Dec. 15, 1998;129(12):1006-11.
Grayson et al., Multi-pulse drug delivery from a resorbable polymeric microchip device. Nat Mater. Nov. 2003;2(11):767-72.
Gross, Mass Spectrometry: A Textbook. Springer. $2^{nd}$ ed. Mar. 1, 2011. Chapter 9. 415-452.
Haro et al., Matrix metalloproteinase-7-dependent release of tumor necrosis factor-alpha in a model of herniated disc resorption. J Clin Invest. Jan. 2000;105(2):143-50.
Haun et al., Micro-NMR for rapid molecular analysis of human tumor samples. Sci Transl Med. Feb. 23, 2011;3(71):71ra16. doi: 10.1126/scitranslmed.3002048.

Imai et al., Degradation of decorin by matrix metalloproteinases: identification of the cleavage sites, kinetic analyses and transforming growth factor-beta1 release. Biochem J. Mar. 15, 1997;322 (Pt 3):809-14.
Ito et al., Degradation of interleukin 1beta by matrix metalloproteinases. J Biol Chem. Jun. 21, 1996;271(25):14657-60.
Jaffer et al., In vivo imaging of thrombin activity in experimental thrombi with thrombin-sensitive near-infrared molecular probe. Arterioscler Thromb Vasc Biol. Nov. 1, 2002;22(11):1929-35.
Johnson et al., Computer program (SEQPEP) to aid in the interpretation of high-energy collision tandem mass spectra of peptides. Biomed Environ Mass Spectrom. Nov. 1989;18(11):945-57.
Kaminskas et al., Methotrexate-conjugated PEGylated dendrimers show differential patterns of deposition and activity in tumor-burdened lymph nodes after intravenous and subcutaneous administration in rats. Mol Pharm. Feb. 2, 2015;12(2):432-43. doi: 10.1021/mp500531e. Epub Jan. 20, 2015.
Kastelic et al., Stefin B, the major low molecular weight inhibitor in ovarian carcinoma. Cancer Lett. Jul. 15, 1994;82(1):81-8.
Kircher et al., A dual fluorochrome probe for imaging proteases. Bioconjug Chem. Mar.-Apr. 2004;15(2):242-8.
Klotz et al., Management of low risk prostate cancer-active surveillance and focal therapy. Nat Rev Clin Oncol. Jun. 2014;11(6):324-34. doi: 10.1038/nrclinonc.2014.73. Epub May 13, 2014.
Ku et al., In vivo sensing of proteolytic activity with an NSET-based NIR fluorogenic nanosensor. Biosens Bioelectron. Mar. 15, 2016;77:471-7. doi: 10.1016/j.bios.2015.09.067. Epub Sep. 30, 2015.
Kuhn et al., Developing multiplexed assays for troponin I and interleukin-33 in plasma by peptide immunoaffinity enrichment and targeted mass spectrometry. Clin Chem. Jun. 2009;55(6):1108-17. doi: 10.1373/clinchem.2009.123935. Epub Apr. 16, 2009.
Kwon et al., Ultrasensitive tumour-penetrating nanosensors of protease activity. Nat Biomed Eng. 2017;1. pii: 0054. doi:10.1038/s41551-017-0054. Epub Apr. 10, 2017.
Kwong et al., Mass-encoded synthetic biomarkers for multiplexed urinary monitoring of disease. Nat Biotechnol. Jan. 2013;31(1):63-70. doi: 10.1038/nbt.2464. Epub Dec. 16, 2012.
Kwong et al., Mathematical framework for activity-based cancer biomarkers. Proc Natl Acad Sci U S A. Oct. 13, 2015;112(41):12627-32. doi: 10.1073/pnas.1506925112. Epub Sep. 28, 2015.
Lange et al., Selected reaction monitoring for quantitative proteomics: a tutorial. Mol Syst Biol. 2008;4:222. doi: 10.1038/msb.2008.61. Epub Oct. 14, 2008.
Larsen et al., Assay of plasma heparin using thrombin and the chromogenic substrate H-D-Phe-Pip-Arg-pNA (S-2238). Thromb Res. Aug. 1978;13(2):285-8.
Lebeau et al., Imaging active urokinase plasminogen activator in prostate cancer. Cancer Res. Apr. 1, 2015;75(7):1225-35. doi:10.1158/0008-5472.CAN-14-2185. Epub Feb. 11, 2015.
Levi et al., Matrix metalloproteinase 2 releases active soluble ectodomain of fibroblast growth factor receptor 1. Proc Natl Acad Sci U S A. Jul. 9, 1996;93(14):7069-74.
Lin et al., Drug-induced amplification of nanoparticle targeting to tumors. Nano Today. Oct. 2014;9(5):550-559. doi:10.1016/j.nantod.2014.09.001. Epub Sep. 23, 2014.
Lin et al., Nanoparticles that sense thrombin activity as synthetic urinary biomarkers of thrombosis. ACS Nano. Oct. 22, 2013;7(10):9001-9. doi: 10.1021/nn403550c. Epub Sep. 12, 2013.
Mallick et al., Computational prediction of proteotypic peptides for quantitative proteomics. Nat Biotechnol. Jan. 2007;25(1):125-31. Epub Dec. 31, 2006.
Mañes et al., The matrix metalloproteinase-9 regulates the insulin-like growth factor-triggered autocrine response in DU-145 carcinoma cells. J Biol Chem. Mar. 12, 1999;274(11):6935-45.
Martinez et al., Diagnostics for the developing world: microfluidic paper-based analytical devices. Anal Chem. Jan. 1, 2010;82(1):3-10. doi: 10.1021/ac9013989.
McLennan et al., Subcutaneous drug delivery and the role of the lymphatics. Drug Discov Today Technol. 2005 Spring;2(1):89-96. doi:10.1016/j.ddtec.2005.05.006.
Mira et al., Insulin-like growth factor I-triggered cell migration and invasion are mediated by matrix metalloproteinase-9. Endocrinology. Apr. 1999;140(4):1657-64.

(56) References Cited

OTHER PUBLICATIONS

Mirtti et al., Expression of cystatins, high molecular weight cytokeratin, and proliferation markers in prostatic adenocarcinoma and hyperplasia. Prostate. Mar. 1, 2003;54(4):290-8.

Mitchell et al., Assay for plasma heparin using a synthetic peptide substrate for thrombin: introduction of the fluorophore aminoisophthalic acid, dimethyl ester. Thromb Res. Jul. 1978;13(1):47-52.

Morgia et al., Matrix metalloproteinases as diagnostic (MMP-13) and prognostic (MMP-2, MMP-9) markers of prostate cancer. Urol Res. Feb. 2005;33(1):44-50. Epub Oct. 22, 2004.

Morris et al., Urine and plasma levels of fibrinopeptide B in patients with deep vein thrombosis and pulmonary embolism. Thromb Res. May 1, 2003;110(2-3):159-65.

Nagase et al., Matrix metalloproteinases. J Biol Chem. Jul. 30, 1999;274(31):21491-4.

Nahrendorf et al., Hybrid in vivo FMT-CT imaging of protease activity in atherosclerosis with customized nanosensors. Arterioscler Thromb Vasc Biol. Oct. 2009;29(10):1444-51. doi:10.1161/ATVBAHA.109.193086. Epub Jul. 16, 2009. Supplemental Material.

Nomura et al., Activity-based protein profiling for biochemical pathway discovery in cancer. Nat Rev Cancer. Sep. 2010;10(9):630-8. doi: 10.1038/nrc2901. Epub Aug. 12, 2010.

Olson et al., In vivo fluorescence imaging of atherosclerotic plaques with activatable cell-penetrating peptides targeting thrombin activity. Integr Biol (Camb). Jun. 2012;4(6):595-605. doi: 10.1039/c2ib00161f. Epub Apr. 26, 2012.

Park et al., Magnetic Iron Oxide Nanoworms for Tumor Targeting and Imaging. Adv Mater. May 5, 2008;20(9):1630-1635.

Park et al., Systematic surface engineering of magnetic nanoworms for in vivo tumor targeting. Small. Mar. 2009;5(6):694-700. doi: 10.1002/smll.200801789.

Peer et al., Nanocarriers as an emerging platform for cancer therapy. Nat Nanotechnol. Dec. 2007;2(12):751-60.

Pomerantz et al., Determination of oligonucleotide composition from mass spectrometrically measured molecular weight. J Am Soc Mass Spectrom. Mar. 1993;4(3):204-9. doi: 10.1016/1044-0305(93)85082-9.

Posthuma-Trumpie et al., Lateral flow (immuno)assay: its strengths, weaknesses, opportunities and threats. A literature survey. Anal Bioanal Chem. Jan. 2009;393(2):569-82. doi: 10.1007/s00216-008-2287-2. Epub Aug. 13, 2008.

Powell et al., The metalloproteinase matrilysin proteolytically generates active soluble Fas ligand and potentiates epithelial cell apoptosis. Curr Biol. Dec. 16-30, 1999;9(24):1441-7.

Prensner et al., Beyond PSA: the next generation of prostate cancer biomarkers. Sci Transl Med. Mar. 28, 2012;4(127):127rv3. doi:10.1126/scitranslmed.3003180.

Rajah et al., Elevated levels of the IGF-binding protein protease MMP-1 in asthmatic airway smooth muscle. Am J Respir Cell Mol Biol. Feb. 1999;20(2):199-208.

Rennke, How does glomerular epithelial cell injury contribute to progressive glomerular damage? Kidney Int Suppl. Feb. 1994;45:S58-63.

Rijkers et al., Design and synthesis of thrombin substrates with modified kinetic parameters. Thromb Res. Sep. 15, 1995;79(5-6):491-9.

Roepstorff et al., Proposal for a common nomenclature for sequence ions in mass spectra of peptides. Biomed Mass Spectrom. Nov. 1984;11(11):601.

Ross et al., Multiplexed protein quantitation in *Saccharomyces cerevisiae* using amine-reactive isobaric tagging reagents. Mol Cell Proteomics. Dec. 2004;3(12):1154-69. Epub Sep. 22, 2004.

Ruoslahti et al., Targeting of drugs and nanoparticles to tumors. J Cell Biol. Mar. 22, 2010;188(6):759-68. doi: 10.1083/jcb.200910104. Epub Mar. 15, 2010.

Santini et al., A controlled-release microchip. Nature. Jan. 28, 1999;397(6717):335-8.

Sawyers, The cancer biomarker problem. Nature. Apr. 3, 2008;452(7187):548-52. doi: 10.1038/nature06913.

Schonbeck et al., Generation of biologically active IL-1 beta by matrix metalloproteinases: a novel caspase-1-independent pathway of IL-1 beta processing. J Immunol. Oct. 1, 1998;161(7):3340-6.

Schuerle et al., Magnetically Actuated Protease Sensors for in Vivo Tumor Profiling. Nano Lett. Oct. 12, 2016;16(10):6303-6310. Epub Sep. 13, 2016.

Shariat et al., Urine detection of survivin is a sensitive marker for the noninvasive diagnosis of bladder cancer. J Urol. Feb. 2004;171(2 Pt 1):626-30.

Smith et al., Rapid identification of highly active and selective substrates for stromelysin and matrilysin using bacteriophage peptide display libraries. J Biol Chem. Mar. 24, 1995;270(12):6440-9

Stein et al., Ultrasensitive Scaffold-Dependent Protease Sensors with Large Dynamic Range. ACS Synth Biol. Jul. 21, 2017;6(7):1337-1342. doi: 10.1021/acssynbio.6b00370. Epub Mar. 28, 2017.

Sugahara et al., Coadministration of a tumor-penetrating peptide enhances the efficacy of cancer drugs. Science. May 21, 2010;328(5981):1031-5. doi:10.1126/science.1183057. Epub Apr. 8, 2010.

Sutherland et al., RGD-Binding Integrins in Prostate Cancer: Expression Patterns and Therapeutic Prospects against Bone Metastasis. Cancers (Basel). Oct. 26, 2012;4(4):1106-45. doi:10.3390/cancers4041106.

Suzuki et al., Matrix metalloproteinase-3 releases active heparin-binding EGF-like growth factor by cleavage at a specific juxtamembrane site. J Biol Chem. Dec. 12, 1997;272(50):31730-7.

Tascilar et al., Role of tumor markers and mutations in cells and pancreatic juice in the diagnosis of pancreatic cancer. Ann Oncol. 1999;10 Suppl 4:107-10.

Taylor et al., Integrative genomic profiling of human prostate cancer. Cancer Cell. Jul. 13, 2010;18(1):11-22. doi:10.1016/j.ccr.2010.05.026. Epub Jun. 24, 2010.

Thompson et al., Tandem mass tags: a novel quantification strategy for comparative analysis of complex protein mixtures by MS/MS. Anal Chem. Apr. 15, 2003;75(8):1895-904. Erratum in: Anal Chem. Sep. 15, 2003;75(18):4942. Johnstone, R [added]. Anal Chem. Jun. 15, 2006;78(12):4235. Mohammed, A Karim A [added].

Thorek et al., Internalization of secreted antigen-targeted antibodies by the neonatal Fc receptor for precision imaging of the androgen receptor axis. Sci Transl Med. Nov. 30, 2016;8(367):367ra167.

Tockman et al., Considerations in bringing a cancer biomarker to clinical application. Cancer Res. May 1, 1992;52(9 Suppl):2711s-2718s.

Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. Epub Aug. 30, 2016.

Truong et al., Isotope-coded chemical reporter and acid-cleavable affinity reagents for monitoring protein sulfenic acids. Bioorg Med Chem Lett. Sep. 1, 2011;21(17):5015-20. doi: 10.1016/j.bmcl.2011.04.115. Epub May 3, 2011.

Tung et al., A novel near-infrared fluorescence sensor for detection of thrombin activation in blood. Chembiochem. Mar. 1, 2002;3(2-3):207-11.

Warren et al., Point-of-care diagnostics for noncommunicable diseases using synthetic urinary biomarkers and paper microfluidics. Proc Natl Acad Sci U S A. Mar. 11, 2014;111(10):3671-6. doi:10.1073/pnas.1314651111. Epub Feb. 24, 2014.

Weissleder et al., In vivo imaging of tumors with protease-activated near-infrared fluorescent probes. Nat Biotechnol. Apr. 1999;17(4):375-8.

Welser et al., Protease responsive nanoprobes with tethered fluorogenic peptidyl 3-arylcoumarin substrates. Chem Commun (Camb). Feb. 14, 2009;(6):671-3. Epub Dec. 8, 2008.

Welser et al., Protease sensing with nanoparticle based platforms. Analyst. Jan. 7, 2011;136(1):29-41. doi: 10.1039/c0an00429d. Epub Sep. 28, 2010.

Whiteaker et al., An automated and multiplexed method for high throughput peptide immunoaffinity enrichment and multiple reaction monitoring mass spectrometry-based quantification of protein biomarkers. Mol Cell Proteomics. Jan. 2010;9(1):184-96. doi: 10.1074/mcp.M900254-MCP200. Epub Oct. 20, 2009.

(56) References Cited

OTHER PUBLICATIONS

Whiteaker et al., Antibody-based enrichment of peptides on magnetic beads for mass-spectrometry-based quantification of serum biomarkers. Anal Biochem. Mar. 1, 2007;362(1):44-54. Epub Dec. 20, 2006.
Whitney et al., Ratiometric activatable cell-penetrating peptides provide rapid in vivo readout of thrombin activation. Angew Chem Int Ed Engl. Jan. 2, 2013;52(1):325-30. doi: 10.1002/anie.201205721. Epub Oct. 18, 2012.
Withana et al., Labeling of active proteases in fresh-frozen tissues by topical application of quenched activity-based probes. Nat Protoc. Jan. 2016;11(1):184-91. doi: 10.1038/nprot.2016.004. Epub Dec. 30, 2015.
Wollscheid et al., Mass-spectrometric identification and relative quantification of N-linked cell surface glycoproteins. Nat Biotechnol. Apr. 2009;27(4):378-86. doi: 10.1038/nbt.1532. Epub Apr. 6, 2009. Erratum in: Nat Biotechnol. Sep. 2009;27(9):864.
Xia et al., Multiplex detection of protease activity with quantum dot nanosenors prepared by Intein-Mediated specific bioconjugation. Analytical Chemistry. Nov. 15, 2008; 22(80) 8649-8655.
Yager et al., Point-of-care diagnostics for global health. Annu Rev Biomed Eng. 2008; 10:107-44. doi: 10.1146/annurev.bioeng.10.061807.160524.
Yu et al., Cell surface-localized matrix metalloproteinase-9 proteolytically activates TGF-beta and promotes tumor invasion and angiogenesis. Genes Dev. Jan. 15, 2000;14(2):163-76.
Zhang et al., Identification and quantification of N-linked glycoproteins using hydrazide chemistry, stable isotope labeling and mass spectrometry. Nat Biotechnol. Jun. 2003;21(6):660-6. Epub May 18, 2003.
Zieske, A perspective on the use of iTRAQ reagent technology for protein complex and profiling studies. J Exp Bot. 2006;57(7):1501-8. Epub Mar. 30, 2006.
U.S. Appl. No. 17/091,075, filed Nov. 6, 2020, Bhatia et al.
U.S. Appl. No. 17/124,999, filed Dec. 17, 2020, Bhatia et al.
EP 17793501.2, Oct. 11, 2019, Extended European Search Report.
[No Author Listed], EMBOSS Needle Sequence Alignment. 2021. 2 pages.
[No Author Listed], Amidase Protein Classification Interpro. 2021. 2 pages.
Gatter et al., Transferrin receptors in human tissues: their distribution and possible clinical relevance. J Clin Pathol. May 1983;36(5):539-45. doi: 10.1136/jcp.36.5.539. PMID: 6302135; PMCID: PMC498283.
Hao et al., CRISPR-Cas-amplified urine biomarkers for multiplexed and portable cancer diagnostics. bioRxiv Jun. 17, 2020.
Jambunathan et al., Prolyl endopeptidase activity in bronchoalveolar lavage fluid: a novel diagnostic biomarker in a guinea pig model of invasive pulmonary aspergillosis. Med Mycol. Aug. 2013;51(6):592-602. doi: 10.3109/13693786.2012.761360. Epub Jan. 28, 2013.
Klan et al., Photoremovable protecting groups in chemistry and biology: reaction mechanisms and efficacy. Chem Rev. Jan. 9, 2013;113(1):119-91. doi: 10.1021/cr300177k. Epub Dec. 21, 2012.
Loynachan et al., Renal clearable catalytic gold nanoclusters for in vivo disease monitoring. Nat Nanotechnol. Sep. 2019;14(9):883-890. doi: 10.1038/s41565-019-0527-6. Epub Sep. 2, 2019. PMID: 31477801; PMCID: PMC7045344.
Parker et al., Folate receptor expression in carcinomas and normal tissues determined by a quantitative radioligand binding assay. Anal Biochem. Mar. 15, 2005;338(2):284-93. doi: 10.1016/j.ab.2004.12.026. PMID: 15745749.
Soleimany et al., Activity-Based Diagnostics: An Emerging Paradigm for Disease Detection and Monitoring. Trends Mol Med. May 2020;26(5):450-468. doi: 10.1016/j.molmed.2020.01.013. Epub Apr. 5, 2020. PMID: 32359477; PMCID: PMC8290463.
Yoo et al., 2'-O-methyl-modified phosphorothioate antisense oligonucleotides have reduced non-specific effects in vitro. Nucleic Acids Res. Apr. 2, 2004;32(6):2008-16. doi: 10.1093/nar/gkh516. PMID: 15064360; PMCID: PMC390367.

\* cited by examiner

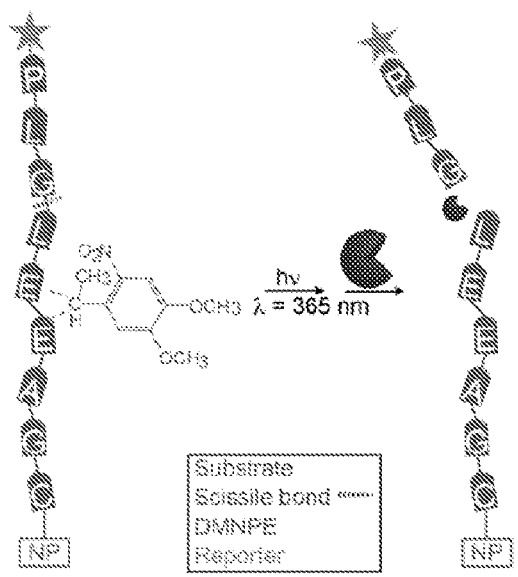
FIG. 2A
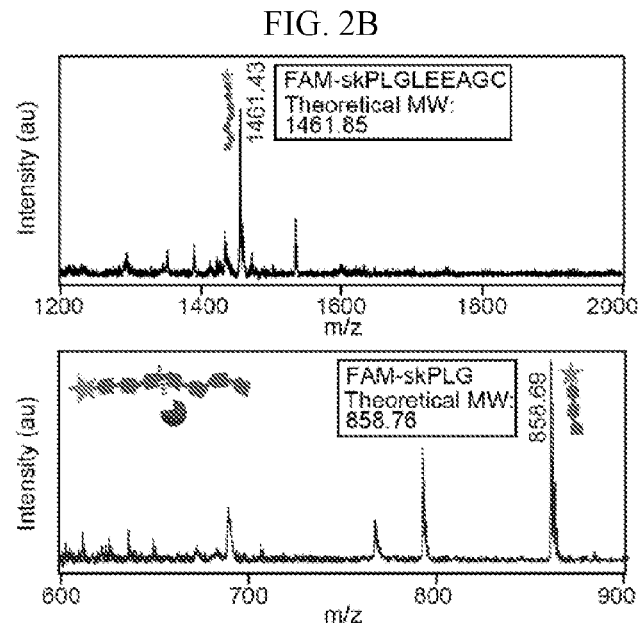
FIG. 2B
FIG. 2C
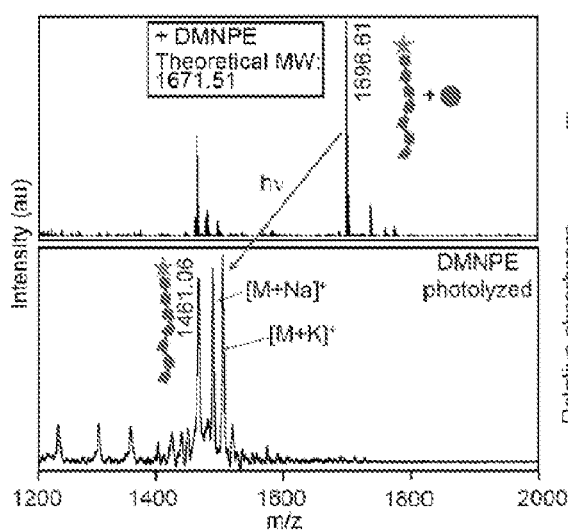
FIG. 2D
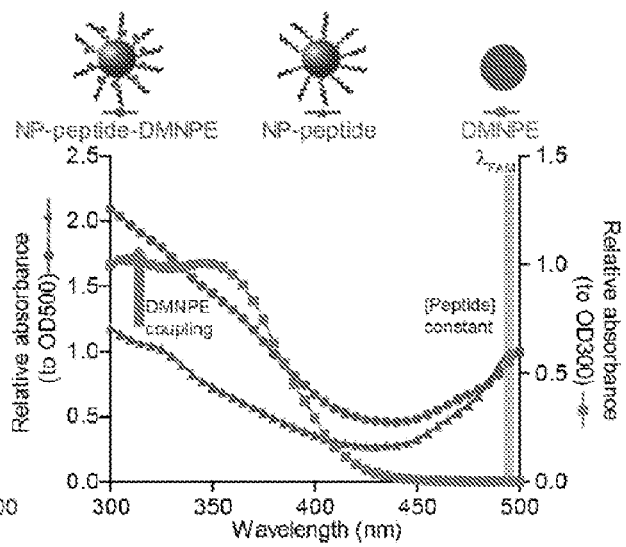
FIG. 2E

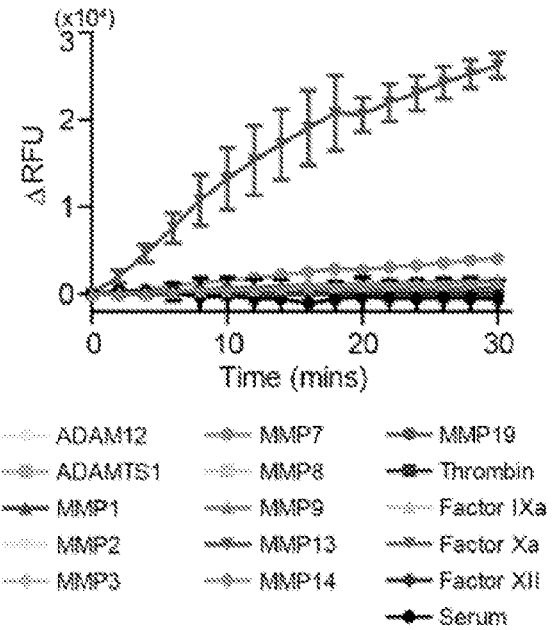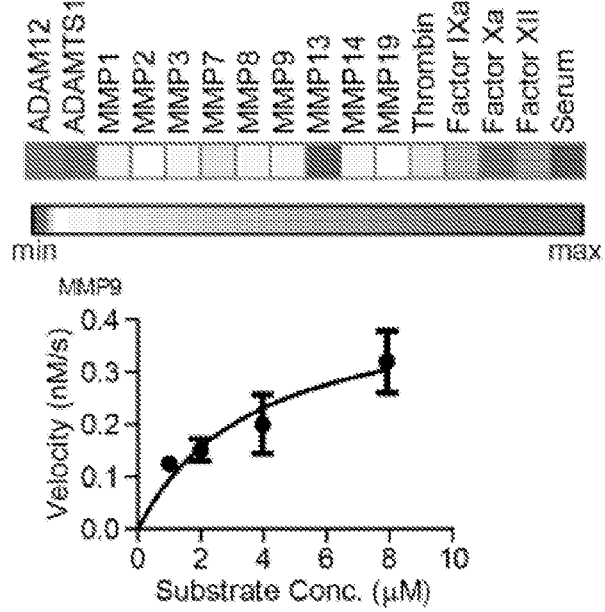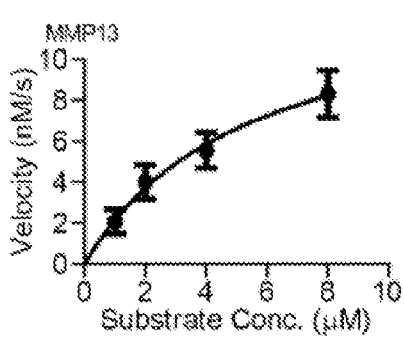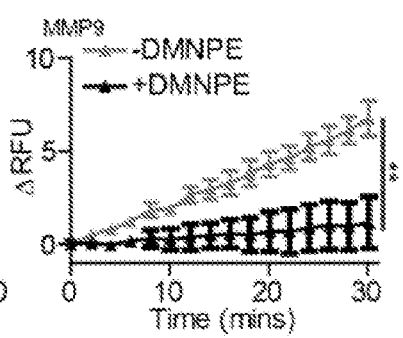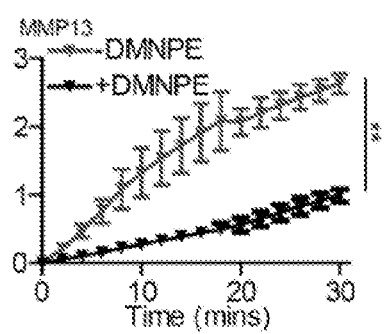
FIG. 3A  FIG. 3B  FIG. 3C  FIG. 3D  FIG. 3E  FIG. 3F FIG. 6A
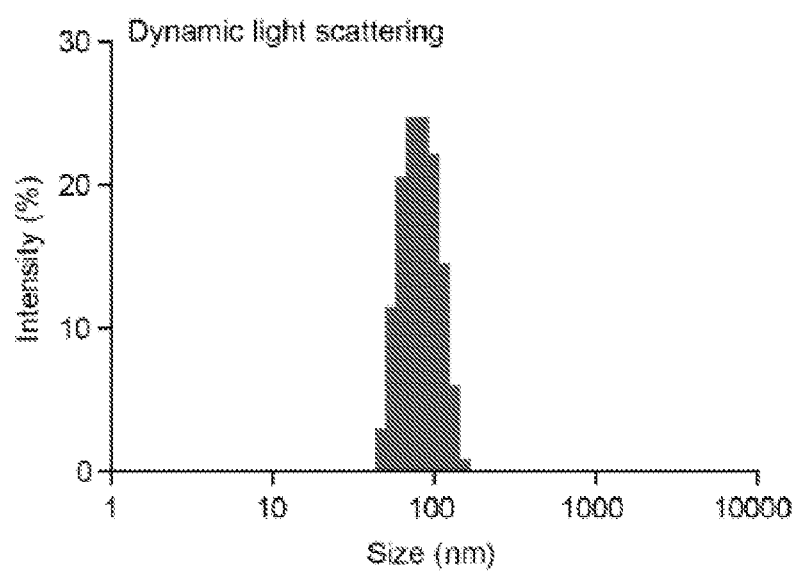
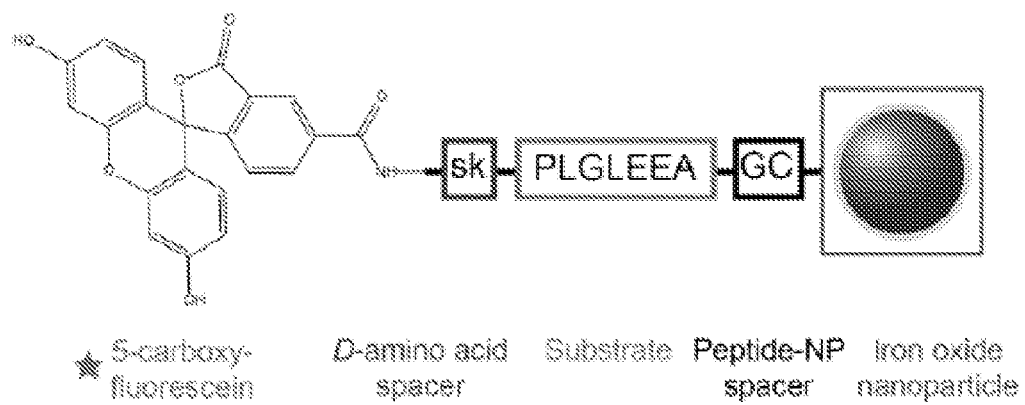
FIG. 6B

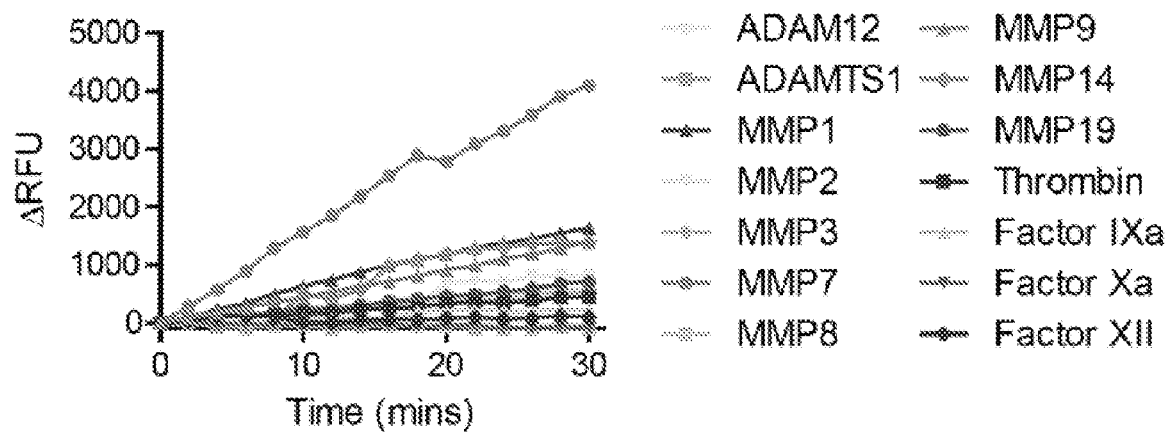
FIG. 8A
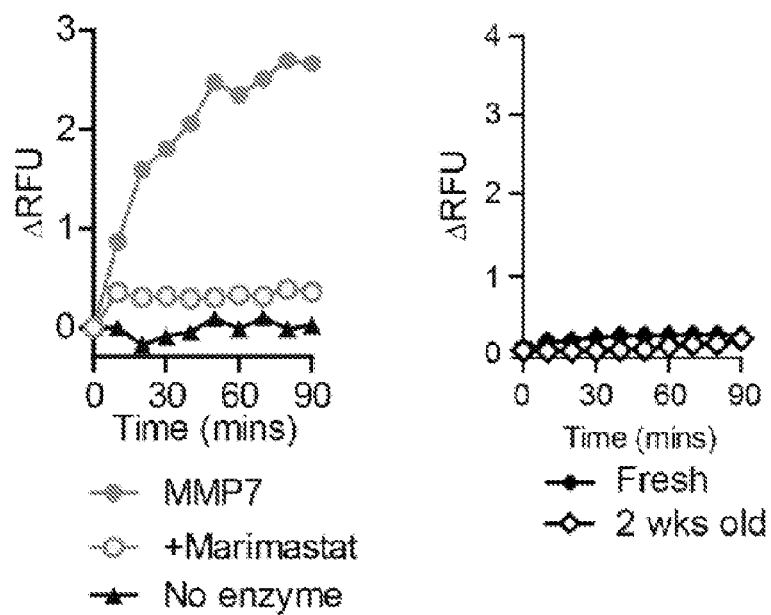
FIG. 8B
FIG. 8C

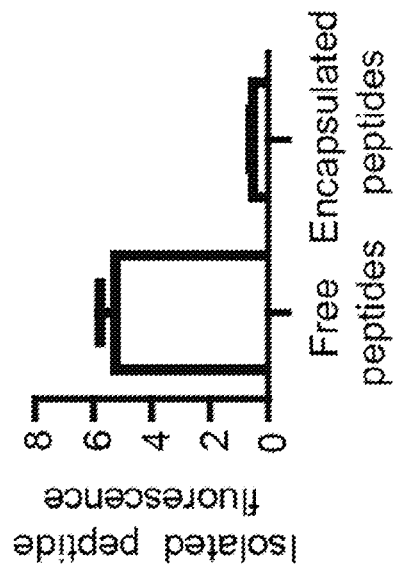
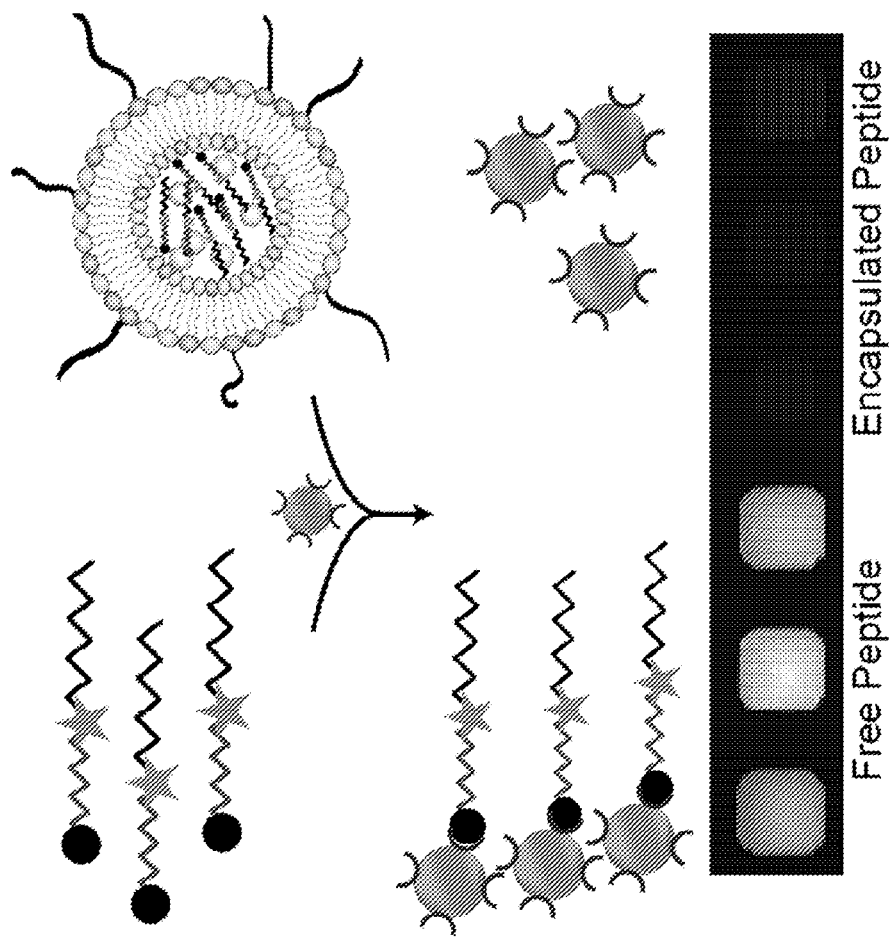
FIG. 27A
FIG. 27B

METHODS AND USES FOR REMOTELY TRIGGERED PROTEASE ACTIVITY MEASUREMENTS

RELATED APPLICATIONS

This application is a national stage filing under 35 U.S.C. § 371 of international application number PCT/US2017/031401, filed May 5, 2017, and claims priority under 35 U.S.C. § 119(e) to U.S. Provisional Application Ser. No. 62/332,096, entitled "METHODS AND USES FOR REMOTELY TRIGGERED PROTEASE ACTIVITY MEASUREMENTS" filed on May 5, 2016, each of which is herein incorporated by reference in its entirety.

BACKGROUND

Targeted cancer therapies require a precise determination of the underlying biological processes driving tumorigenesis. Tumors are complex systems, with the tumor microenvironment, including stroma, extracellular matrix factors, and immune cells, actively contributing to disease progression. Therefore, new diagnostic tools that capture the activity at the disease site in vivo are needed to better understand individual tumor behavior and ultimately maximize therapeutic response. Matrix metalloproteinases (MMPs) play an important role in driving multiple aspects of tumorigenesis, and their activity can be monitored using engineered peptide substrates as protease-specific probes. To identify tumor specific activity profiles, enhanced specific sampling of the tumor microenvironment is necessary. Current strategies for detecting protease activity are focused on functionalizing synthetic peptide substrates with reporters that emit detection signals following peptide cleavage. However, these activity-based probes lack the capacity to be turned on at sites of interest and, therefore, are subject to off-target activation.

SUMMARY

The present disclosure relates to methods and products associated with in vitro and in vivo protease activity measurements and enzyme profiling. Some aspects of the present disclosure relate to measuring remotely triggered protease activity. In particular, the disclosure relates to methods of in vivo processing of exogenous molecules followed by detection of signature molecules as representative of the presence or absence of active enzymes associated with disease or conditions. The disclosure also relates to products, kits, and databases for use in the methods as described by the disclosure.

In some aspects, the disclosure provides a composition of a biomarker nanoparticle, wherein the biomarker nanoparticle comprises a modular structure having a carrier domain linked to an enzyme susceptible detectable marker, wherein the enzyme susceptible detectable marker is comprised of an enzyme susceptible domain linked to a detectable marker and a protecting group, whereby the detectable marker is capable of being released from the biomarker nanoparticle when exposed to an enzyme when the protecting group is deactivated.

In some embodiments, the protecting group is positioned at a residue adjacent to an enzyme-target scissile bond in the enzyme susceptible detectable marker. In some embodiments, the protecting group is a photolabile group. In some embodiments, the protecting group is a thermosensitive molecule, such as a thermosensitive liposome. In some embodiments, the photolabile group is a large molecule that provides steric hindrance protection from enzymatic cleavage.

The enzyme susceptible domain, in some embodiments, is a cancer substrate.

In some embodiments, the carrier domain is an iron oxide nanoparticle and the enzyme susceptible detectable marker is fluorescein-conjugated.

A method is provided according to other aspects of the disclosure. In some embodiments, the method involves administering to a subject a biomarker nanoparticle as described herein; exposing the subject to an external force to deactivate the protecting group; analyzing a biological sample from the subject, wherein the biological sample is not a sample from the site of administration of the biomarker nanoparticle, and determining whether the detectable marker is in the biological sample, wherein the presence of the detectable marker in the biological sample is indicative of the enzyme being present in an active form within the subject.

In some embodiments, the biological sample is urine.

The biomarker nanoparticle, in some embodiments, is a multiplexed library of enzyme susceptible detectable markers. In some embodiments, the multiplexed library of enzyme susceptible detectable markers is 2 or more enzyme susceptible detectable markers, 5 or more enzyme susceptible detectable markers, or 10 or more enzyme susceptible detectable markers.

In some embodiments, the enzyme susceptible detectable markers are mass encoded protease substrates or ligand encoded protease substrates. The step of analyzing the biological sample detectable markers involves, in some embodiments, identifying mass-encoded protease substrates using LC-MS/MS.

The external force may be any kind of force that exerts an effect on the protecting group. For instance, the external force may be a magnetic field source such as an alternating magnetic field (AMF), an ultraviolet A (UVA) light source or an infrared light source. In some embodiments, the UVA light is 365 nm. In some embodiments, the UVA light is administered via photon upconversion or two-photon technology. In some embodiments, the UVA light is administered via an implantable light source.

In some embodiments, the protecting group is a photolabile group. The photolabile group may be a small molecule responsive to different wavelength activations. In some embodiments, the photolabile group is 1-(4,5-dimethoxy-2-nitrophenyl) diazoethane (DMNPE), coumarin, or benoquinolone.

In some embodiments, the protecting group is a thermosensitive molecule, such as a thermosensitive liposome. In some embodiments, the thermosensitive liposome is a liposome nanocarrier containing magnetic nanoparticles.

In some embodiments, the protecting group is a liposomal carrier containing gold nanoparticles, a pH-responsive liposomal nanocarrier or a reactive oxygen-responsive liposomal nanocarrier.

Each of the embodiments of the disclosure can encompass various recitations made herein. It is, therefore, anticipated that each of the recitations of the disclosure involving any one element or combinations of elements can, optionally, be included in each aspect of the disclosure.

BRIEF DESCRIPTION OF THE DRAWINGS

FIG. 1A shows the enablement of remotely activated protease activity measurements via the coupling of photolabile groups directly to peptide substrates, hindering protease access until activation. The photolabile groups can be efficiently photolyzed with 365 nm light to unveil enzyme cleavage sites and enable local protease activity measurements. The principle was used to probe local protease activity in models of cancer.

FIGS. 2A-2E show that protecting groups can be coupled to amino acids adjacent to the scissile bond. FIG. 2A shows that the peptide backbone can be directly modified with a photolabile group (DMNPE) at acidic residues. Adjacent to the peptide substrate, reporters that can be either fluorigenic or ligand-encoded are released upon cleavage. Activation by light removes the photolabile group and enables proteases to access the peptide. The sequences correspond to SEQ ID NOs: 9 and 10 from left to right, respectively. FIG. 2B shows a mass spectrometry analysis of the native peptide sequence (SEQ ID NO: 3). FIG. 2C shows identification of the scissile bond by mass spectrometry analysis of a MMP9-cleaved peptide fragment (SEQ ID NO: 11). In FIG. 2D, coupling of a DMNPE molecule is confirmed by an m/z shift corresponding to the mass of one DMNPE molecule. Photolysis results in a mass shift back to the original mass of the native peptide. FIG. 2E shows the spectral characteristic of NP-peptides (triangles) and spectral shift with DMNPE coupled (circle) that approximately matches spectra of free DMNPE.

FIGS. 3A-3H show STREAM sensing of recombinant proteases. FIG. 3A shows fluorescence dequenching measurements of protease cleavage by multiple enzymes targeting C1-NPs. MMP13, 7, 1, 9, and 14 are able to cleave the substrate, with MMP13 as the most efficient. FIG. 3B shows a heatmap of cleavage velocity of the different proteases. FIG. 3C shows the Michaelis-Menten analysis of MMP9 cleavage of C1-NPs. FIG. 3D shows the Michaelis-Menten analysis of MMP13 cleavage of C1-NPs. FIG. 3E shows dequenching measurements of MMP9 cleavage against unmodified C1-NPs and DMNPE-veiled C1-NPs. FIG. 3F shows dequenching measurements of MMP9 cleavage against unmodified C1-NPs and DMNPE-veiled C1-NPs. FIG. 3G shows light activation of particles and subsequent increase in MMP9 activity. FIG. 3H shows light activation of particles and subsequent increase in MMP13 activity. (All experiments: n=2-3; all error bars: (SD; e/f: **P<0.01, 2way ANOVA; g/h: *P<0.05, one-tail, Student's t-test; light exposure: 8 mW/cm$^2$).

FIG. 4A shows 3D collagen tissues containing embedded colorectal cancer cells established as an in vitro model of the tumor microenvironment. Cells inside the collagen gel can be visualized and are homogeneously distributed (scale bar: 200 μm). C1-NPs (veiled or unmodified, L and D stereoisomers) were also embedded. One day after forming the gel, the surrounding media was assessed for peptide fluorescence (FIG. 4B). Veiled substrates had significantly lower rates of proteolysis as did D-stereoisomer peptides compared to gels that contained L-stereoisomer particles (*P<0.05, two-tail Student's t-test, n=3, SEM). FIG. 4C shows spatial and temporal activation of STREAMs in cancer collagen tissue. The left half of gels was exposed to light on day 1, and total peptide signal was measured in collected supernatant. Three days later, the right half of gels was activated, and peptide signal was measured (**P<0.01, *P<0.05, two-tail, paired Student's t-test; n=3, SEM; light exposure: 30 s at 200 mW/cm$^2$.)

FIG. 5A shows V1-NPs were veiled with DMNPE and injected into healthy mice. This resulted in a ~4-fold decrease in signal compared to unmodified substrates. Ex vivo activation and subsequent infusion into mice resulted in a signal increase of a ~3-fold (***P<0.001, two-tail Student's t-test). FIG. 5B shows urinary reporter concentrations from tumor mice were significantly greater than healthy mice confirming that V1-NPs could be used as synthetic biomarkers of cancer (*P<0.05, two-tail Student's t-test). One hour after NP injection, mice were voided of urine, and STREAMs were activated at the tumor (FIG. 5C). Urine was collected 30 min after. Approximately a 2-fold increase could be detected with the addition of light at the tumor. The same protocol was followed using unmodified substrates. There was no significant difference between the tumor animals and the control animals with unmodified substrates being exposed to light at this 1.5 h time point, owing to rapid depletion of available substrates (*P<0.05, **P<0.01, two-tail Student's t-test; light exposure: 30 s at 200 mW/cm$^2$).

FIGS. 6A-6B shows the design of protease sensing nanoparticles for in vitro applications. FIG. 6A shows dynamic light scattering measurement of nanoparticle size. FIG. 6B shows the in vitro protease sensor (C1-NPs) is comprised of a fluorescent reporter connected to the substrate and coupled to NPs. The sequence corresponds to SEQ ID NO: 12.

FIG. 7A showed veiled sensors (DMNPE-NP) or unmodified sensors (NP) were exposed to light for 30 minutes, purified, and absorbance was compared to unexposed particles. The decrease in relative absorbance from the 300-400 nm window, indicates photolysis of the DMNPE. Normalized to the FAM absorbance ($\lambda$=500 nm). FIG. 7B shows quenching on nanoparticles is achieved at high-valency coupling, in comparison to free FAM (Excitation: 470 nm; emission: 500-700 nm; cutoff: 495 nm; quenching efficiency=81.8%). FIG. 7C shows nanoparticles added to human control serum and fluorescence was measured over 24 hours. No dequenching was observed.

FIGS. 8A-8C show the biochemical characterization of substrate susceptibility of substrate to proteases. FIG. 8A shows a subset of proteases from FIG. 3A that can cleave the substrate. FIG. 8B shows that Marimastat, an MMP inhibitor, abrogates cleavage showing fluorescence is generated through proteolysis. FIG. 8C shows that DMNPE conjugation is stable. Samples tested for proteolysis against MMP9 two weeks after conjugation perform similarly to freshly coupled DMNPE-peptide conjugates.

FIG. 9A shows that two-photon light at 690 nm is able to unveil the STREAM particles. FIG. 9B shows NVOC-rhodamine used to test if exposure to two-photon light for 120 seconds would cause an increase in rhodamine fluorescence. Mean rhodamine intensity increased after light exposure. FIG. 9C shows two-photon unveiled STREAMs were exposed to MMP13 and activity was measured. MMP13 activity against the substrates increased with two-photon unveiling (n=2, ±s.e.m.; 50% power of laser operating at 1 W).

FIG. 10A shows alternate substrate/reporter pair veiled by DMNPE and tested against plasmin. FIG. 10B shows the addition of DMNPE confirmed by shifts in absorbance from 300-400 nm. Photolysis shifts the absorbance back towards unmodified. FIG. 10C shows proteolysis mitigated by DMNPE veiling, which is recovered by light unveiling.

FIG. 11A shows C1-NPs were exposed to supernatant from colorectal cancer cells (LS174 Ts) to determine if they can detect protease activity of a cellular origin. D-amino acid control sequence: c1, FAM-sk-pl-Gleea-GC (SEQ ID NO: 14). FIG. 11B shows protease sensors are sensitive to cellular concentration by incubating sensors at the same concentration in conditioned media from high or low-density cell cultures. FIG. 11C shows that secreted proteases from normal fibroblast cells (CCD-18Co cell line) cleaved the sensor to a lesser extent (n=3, s.e.m. for a-c, *P<0.05, Student's t-test).

FIG. 12A shows the fluorescence of light-sensitive rhodamine. After light activation on the left half of the gel, rhodamine fluorescence is visualized on the left side. Quantification of rhodamine intensity on either side of the gel. Increases can be detected in the side corresponding with side that was illuminated (*P<0.05, ns P>0.05, two-tail, Student's t-test). FIG. 12B shows unmodified substrates that were also embedded in another set of collagen cancer tissues. The signal for these stays high throughout (compared to protected; see FIGS. 4B-4C) and is unaffected by light exposure. Similar to protected sensors, the left half of gels was exposed on Day 1 and the right half on Day 4 (ns, P>0.05, two-tail, paired Student's t-test, n=3, s.e.m.).

FIG. 14A shows sandwich ELISA characterization with a strong linear signal corresponding to reporter concentration. ELISA can detect low picomolar concentrations, making it amenable for urine-based protease activity measurements (n=2, s.d.). FIG. 14B shows the absorbance spectra of nanoparticles used in experiments described in FIG. 5A. The same quantity of peptide for unmodified and veiled was injected in mice. FIG. 14C shows that, after light activation of protected peptides, the relative absorbance at 350 nm associated with DMNPE decreases down closer to unprotected substrates.

FIG. 16A shows agarose hydrogels embedded with STREAMs and recombinant MMP9 at concentrations approximately those expected in vivo. FIG. 16B shows that agarose hydrogels have similar transmission to skin at 365 nm. This is important, as it serves to validate that light activation through skin is feasible. FIG. 16C shows that light activation of 1 minute is sufficient to drastically increase the proteolysis measurements made in the hydrogel. The signal generated can be measured over several hours (200 mW/cm$^2$).

FIG. 18A shows thermosensitive liposomes encapsulated with magnetic nanoparticles and synthetic peptides. Upon exposure to alternating magnetic fields, heat is dissipated by the co-entrapped MNPs due to hysteresis losses. The permeabilized membrane allows peptides to diffuse to the exterior where they are cleaved by proteases. Cleaved and uncleaved peptides clear into urine, where cleaved reporters are isolated by depletion of uncleaved reporters using streptavidin-coated magnetic beads. FIG. 18B shows the characterization of a cleavage quantification assay and protease specificities. The top image is a schematic of the assay. The N-terminal biotin identifies an uncleaved substrate, which can be depleted using streptavidin beads. Measurements of cleaved reporters is enabled by a Cy7 fluorophore. The lower image illustrates three different results: left, a Cy7 signal of an initial peptide solution before the addition of MMP, middle, no fluorescence signal was detected after the depletion with streptavidin beads, and right, the addition of MMP9 and subsequent streptavidin depletion results in similar fluorescent levels as the initial peptide solution, showing robust cleavage of the substrate. FIG. 18C shows a recombination assay performed for three distinct peptides substrates. Data was clustered via hierarchical clustering (one minus Pearson correlation), revealing substrate cleavage patterns.

FIG. 19A is a schematic of the in vivo profiling assay. One hour after MAPS administration, urine was collected to measure background signal. Three hours post injection, AMF was applied locally at the tumor and urine collected one hour after activation. FIG. 19B shows that, prior to activation, two cohorts of mice show similar urine reporter concentrations. FIG. 19C shows that, after activation, significantly greater urine reporter concentrations can be detected in the group exposed to AMF (n=5, *P<0.05 Student's t-test). FIG. 19D presents MAPS urinary signatures after activation across the three substrates for LS174T and HCT-8 (FIG. 19E), revealing that S1 and S3 are cleaved at greater rate than S2 in LS174T.

FIG. 20A shows dynamic light scattering measurements of MAPS (purple) and disrupted MAPS after addition of 0.1% TritonX, showing the release of coentrapped MNPs. Separate measurement of pure MNPs is overlaid in black. The inset on the left shows a Transmission Electron Microscopy image of an individual MAPS. FIG. 20B shows absorbance spectra of various components of MAPS. The final spectra of MAPS shows characteristic absorbance of NPs in liposomes and IR-tagged peptides. FIG. 20C demonstrates that no calcein release was measured from MAPS at 37° C. over 30 min. FIG. 20D shows that, at higher temperatures, the release of calcein was detected.

FIG. 21A shows optimal AMF parameters evaluated by calorimetric measurements. Increase of SLP with increasing field strength at 515 kHz (resonance frequency) was measured and extrapolated with a power law valid for field strength magnitudes between 0 and 20 kA/m. The inset depicts the fluid temperature increase during 30 s of AMF exposure at 515 kHz and 15 kA/m, the conditions that were applied in for in vitro and in vivo activation of MAPS. FIG. 21B is a technical drawing of coil with ferromagnetic core utilized in studies. The inset maps the distribution of the SLP for our 25 nm large particles at 515 kHZ across the 12.5 mm wide gap as a result of the spatial variation of the field strength. FIG. 21C depicts IR measurements of heat dissipation in gap of coil during a duty cycle of 40 s on time and 240 s off time, showing steady coil temperature cycles that do not exceed 36° C. FIG. 21D shows liposomes prepared with quenched calcein solution and with and without MNPs exposed to an AMF sequence (515 kHz, 15 kA/m for 40 s). Fluorescence release was quantified. The release profiles were compared to fluorescence signal increase by the addition of Triton-X, which destroys the liposomal structure.

FIG. 25A shows the approach for isolating uncleaved substrate-reporter tandems. FIGS. 25B and 25C demonstrate depletion in PBS (FIG. 25B) and 2% urine (FIG. 25C).

FIGS. 27A-27B show peptides shielded inside liposomes. FIG. 27A shows an analysis of whether streptavidin beads could bind to unencapsulated peptides inside liposomes after synthesis and purification. When the peptide was encapsulated, very little fluorescence was detected. FIG. 27B shows the quantification of peptide fluorescence isolated by streptavidin beads.

FIG. 28A shows plasma concentration of fluorescently labelled liposomes fit to a one-phase exponential decay equation. Activation should occur at a time greater than half-life to avoid blood activation. FIG. 28B shows the accumulation of MAPS measured by an IR scanner of organs and tumors harvested after 3, 6 and 12 hours. The relatively low fluorescence signal in the kidneys indicates that the liposomes had not released their fluorescent contents, which would result in high kidney fluorescence. Combined, these studies indicate that 3 hours post injection would be an optimal time point for triggering of the peptide release.

FIG. 30A demonstrates secreted MMP2 levels between LS174T and HCT-8 as measured by an ELISA. FIG. 30B shows the proteolysis of quenched substrates 1-3 over time by conditioned media from LS174T cells. Mar=marimastat, an MMP inhibitor. FIG. 30C shows the cleavage of S1-3 by secreted proteases from conditioned media from HCT-8 cells.

FIG. 31A illustrates that free peptides injected into healthy nude mice showed S3 with lowest background proteolysis. FIG. 31B illustrates that free peptides injected into LS174T flank tumor bearing mice show a different proteolysis pattern than MAPS. FIG. 31C shows that a heatmap and clustering of all in vivo experiments reflect the similar performances of S1 and S3 as seen in the in vitro recombinant enzyme experiments (FIG. 18C).

DETAILED DESCRIPTION

Figure 1:
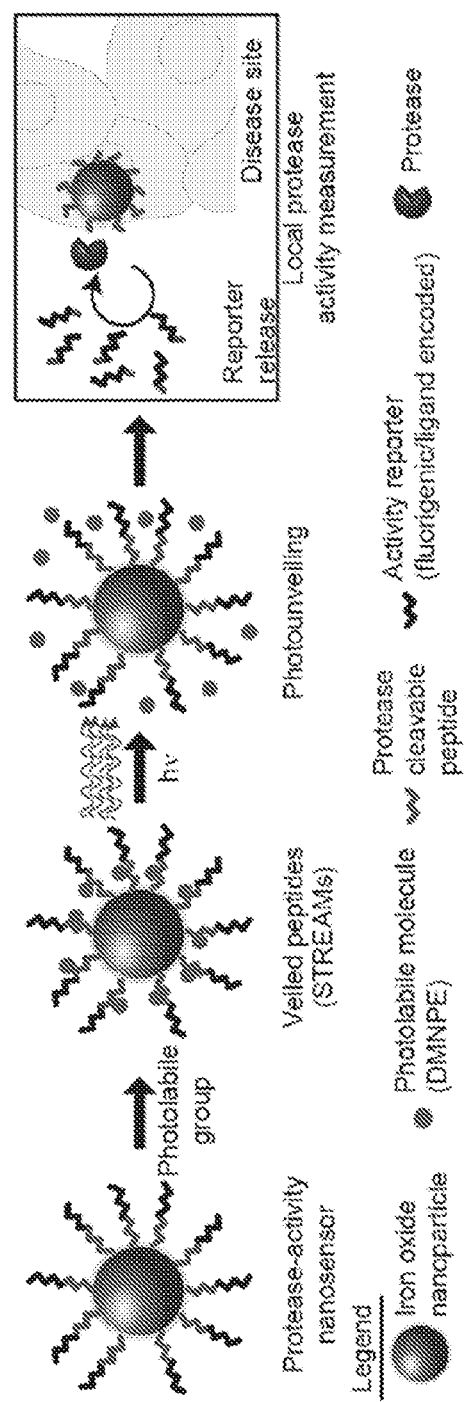
FIG. 1 illustrates photoactivatable sensors of protease activity.

The status of physiological conditions of a subject can be assessed using the methods of the disclosure, for example by identifying molecular properties also referred to as "molecular signatures" or "detectable markers". Such molecular signatures are useful, in some embodiments, for diagnosing diseases such as cancer, infectious disease and arteriosclerosis, as well as for prognostic indicators. The response of most cancers to medical intervention is currently monitored by physical exams and various clinical imaging modalities. A few cancers such as prostate and ovarian cancer are monitored by use of single biomarkers in the blood. Such diagnostic techniques are achieved, for instance using fluorescence detection of molecular markers which are activated in a particular disease state.

In some aspects, the present disclosure uses external forces to precisely control both the location and time of activity-based sensing. As shown in the Examples, photocaged activity-based sensors were created by conjugating photolabile molecules directly onto peptide substrates, thereby blocking protease cleavage by steric hindrance. At sites of disease, exposure to ultraviolet light or other external forces unveils the nanosensors to allow proteases to cleave and release a reporter fragment that can be detected remotely. The spatiotemporally controlled system is applied to probe secreted protease activity in vitro and tumor protease activity in vivo. In vitro, the ability to dynamically and spatially measure metalloproteinase activity in a 3D model of colorectal cancer was demonstrated. In vivo, veiled nanosensors were selectively activated at the primary tumor site in colorectal cancer xenografts to capture the tumor microenvironment-enriched protease activity. The ability to remotely control activity-based sensors offers a valuable tool for measuring biological activity.

In another aspect, the present disclosure includes a protease-activity nanosensor that can be remotely activated at the site of disease via alternating magnetic fields at 500 kHz and 15 kA/m. The nanosensor is comprised of thermosensitive liposome incorporating functionalized peptide substrates that are unveiled at the target site by remotely triggered heat dissipation of co-encapsulated magnetic nanoparticles (MNPs). High specific power losses of our co-encapsulated MNPs on the order of 600 W/g were found, making them amenable to remote triggering. A unique detection assay to quantify the amount of cleaved substrates in the urine was also designed. The spatiotemporally controlled system was used to determine tumor protease activity in vivo and differences in MMP profiles between two in vivo human colorectal cancer models that could not be assayed in vitro were identified.

Aberrantly expressed proteases are candidate enzymes for cancer detection and analysis as they play critical roles in many cancers. Accordingly, in some embodiments, the disclosure relates to the delivery of a set of protease-sensitive substrates to a subject. When a user would like to detect presence of signal indicative of a protease, a remote control, or external force, is activated. Upon activation the protease-sensitive substrate is free to encounter their cognate proteases. The peptide substrates are cleaved and detectable markers are excreted into urine, providing a non-invasive diagnostic readout. In some embodiments, the delivered substrates are responsive to proteases enriched in different stages of tumor invasiveness (e.g., metastasis) and provide a high resolution, functionality driven snapshot of a particular tumor microenvironment (e.g., metastases).

Accordingly, in some aspects the disclosure provides a composition comprising a biomarker nanoparticle, wherein the biomarker nanoparticle comprises a modular structure having a carrier domain linked to an enzyme susceptible detectable marker, wherein the enzyme susceptible detectable marker is comprised of an enzyme susceptible domain linked to a detectable marker and a protecting group, whereby the detectable marker is capable of being released from the biomarker nanoparticle when exposed to an enzyme when the protecting group is deactivated.

In some embodiments, the biomarker nanoparticle comprises a modular structure having a carrier domain linked to an enzyme susceptible detectable marker. A modular structure, as used herein, refers to a molecule having multiple domains.

The carrier domain may include a single type of enzyme susceptible detectable marker, such as, a single type of enzyme susceptible domain and or detectable marker or it may include multiple type of enzyme susceptible detectable markers, such as, different enzyme susceptible domains and detectable markers. For instance each carrier may include 1 type of enzyme susceptible detectable marker or it may include 2-1,000 different enzyme susceptible detectable markers or any integer therebetween. Alternatively each carrier may include greater than 1,000 enzyme susceptible detectable markers. Multiple copies of the biomarker nanoparticle are administered to the subject. Some mixtures of biomarker nanoparticles may include enzyme susceptible detectable markers that are enzymes, others may be enzymatic susceptible domains, and other may be mixtures of the two. Additionally, a plurality of different biomarker nanoparticles may be administered to the subject to determine whether multiple enzymes and/or substrates are present. In that instance, the plurality of different biomarker nanoparticles includes a plurality of detectable markers, such that each enzyme susceptible domain is associated with a particular detectable marker or molecules.

The carrier domain may serve as the core of the nanoparticle. A purpose of the carrier domain is to serve as a platform for the enzyme susceptible detectable marker. As such, the carrier can be any material or size as long as it can serve as a carrier or platform. Preferably the material is non-immunogenic, i.e. does not provoke an immune response in the body of the subject to which it will be administered. Another purpose is that it may function as a targeting means to target the modular structure to a tissue, cell or molecule. In some embodiments the carrier domain is a particle. A particle, for example, a nanoparticle, may, for instance, result in passive targeting to tumors by circulation. Other types of carriers, include, for instance, compounds that cause active targeting to tissue, cells or molecules. Examples of carriers include, but are not limited to, microparticles, nanoparticles, aptamers, peptides (RGD, iRGD, LyP-1, CREKA, etc.), proteins, nucleic acids, polysaccharides, polymers, antibodies or antibody fragments (e.g., herceptin, cetuximab, panitumumab, etc.) and small molecules (e.g., erlotinib, gefitinib, sorafenib, etc.).

In some embodiments the carrier domain is also the protecting group. In that instance the carrier/protecting group can serve two functions in a single component module or domain.

As used herein the term "particle" includes nanoparticles as well as microparticles. Nanoparticles are defined as particles of less than 1.0 μm in diameter. A preparation of nanoparticles includes particles having an average particle size of less than 1.0 μm in diameter. Microparticles are particles of greater than 1.0 μm in diameter but less than 1 mm. A preparation of microparticles includes particles having an average particle size of greater than 1.0 μm in diameter. The microparticles may therefore have a diameter of at least 5, at least 10, at least 25, at least 50, or at least 75 microns, including sizes in ranges of 5-10 microns, 5-15 microns, 5-20 microns, 5-30 microns, 5-40 microns, or 5-50 microns. A composition of particles may have heterogeneous size distributions ranging from 10 nm to mm sizes. In some embodiments the diameter is about 5 nm to about 500 nm. In other embodiments, the diameter is about 100 nm to about 200 nm. In other embodiment, the diameter is about 10 nm to about 100 nm.

The particles may be composed of a variety of materials including iron, ceramic, metallic, natural polymer materials (including lipids, sugars, chitosan, hyaluronic acid etc.), synthetic polymer materials (including poly-lactide-coglycolide, poly-glycerol sebacate, etc.), and non-polymer materials, or combinations thereof.

The particles may be composed in whole or in part of polymers or non-polymer materials. Non-polymer materials, for example, may be employed in the preparation of the particles. Exemplary materials include alumina, calcium carbonate, calcium sulfate, calcium phosphosilicate, sodium phosphate, calcium aluminate, calcium phosphate, hydroxyapatite, tricalcium phosphate, dicalcium phosphate, tricalcium phosphate, tetracalcium phosphate, amorphous calcium phosphate, octacalcium phosphate, and silicates. In certain embodiments the particles may comprise a calcium salt such as calcium carbonate, a zirconium salt such as zirconium dioxide, a zinc salt such as zinc oxide, a magnesium salt such as magnesium silicate, a silicon salt such as silicon dioxide or a titanium salt such as titanium oxide or titanium dioxide.

A number of biodegradable and non-biodegradable biocompatible polymers are known in the field of polymeric biomaterials, controlled drug release and tissue engineering (see, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; 4,638,045 to Kohn; see also Langer, Acc. Chem. Res. 33:94, 2000; Langer, J. Control Release 62:7, 1999; and Uhrich et al., Chem. Rev. 99:3181, 1999; all of which are incorporated herein by reference).

Polymers include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride and polystyrene.

Examples of non-biodegradable polymers include ethylene vinyl acetate, poly(meth) acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginnate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. In some embodiments the polymers are polyesters, polyanhydrides, polystyrenes, polylactic acid, polyglycolic acid, and copolymers of lactic and glycoloic acid and blends thereof.

PVP is a non-ionogenic, hydrophilic polymer having a mean molecular weight ranging from approximately 10,000 to 700,000 and the chemical formula $(C_6H_9NO)[n]$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan™, and Vinisil™. PVP is non-toxic, highly hygroscopic and readily dissolves in water or organic solvents.

Polyethylene glycol (PEG), also known as poly(oxyethylene) glycol, is a condensation polymer of ethylene oxide and water having the general chemical formula $HO(CH_2CH_2O)[n]H$.

Polyvinyl alcohol (PVA) is a polymer prepared from polyvinyl acetates by replacement of the acetate groups with hydroxyl groups and has the formula $(CH_2CHOH)[n]$. Most polyvinyl alcohols are soluble in water.

PEG, PVA and PVP are commercially available from chemical suppliers such as the Sigma Chemical Company (St. Louis, Mo.).

In certain embodiments the particles may comprise poly(lactic-co-glycolic acid) (PLGA).

The carrier may be composed of inorganic materials. Inorganic materials include, for instance, magnetic materials, conductive materials, and semiconductor materials.

In addition to particles the carrier may be composed of any organic carrier, including biological and living carriers such as cells, viruses, bacteria, as well as any non-living organic carriers, or any composition enabling exposure of enzyme substrates to enzymes in disease (including extracellular, membrane-bound, and intracellular enzymes).

In some embodiments, the particles are porous. A porous particle can be a particle having one or more channels that extend from its outer surface into the core of the particle. In some embodiments, the channel may extend through the particle such that its ends are both located at the surface of the particle. These channels are typically formed during synthesis of the particle by inclusion followed by removal of a channel forming reagent in the particle.

The size of the pores may depend upon the size of the particle. In certain embodiments, the pores have a diameter of less than 15 microns, less than 10 microns, less than 7.5 microns, less than 5 microns, less than 2.5 microns, less than 1 micron, less than 0.5 microns, or less than 0.1 microns. The degree of porosity in porous particles may range from greater than 0 to less than 100% of the particle volume. The degree of porosity may be less than 1%, less than 5%, less than 10%, less than 15%, less than 20%, less than 25%, less than 30%, less than 35%, less than 40%, less than 45%, or less than 50%. The degree of porosity can be determined in a number of ways. For example, the degree of porosity can be determined based on the synthesis protocol of the carriers (e.g., based on the volume of the aqueous solution or other channel-forming reagent) or by microscopic inspection of the carriers post-synthesis.

The plurality of particles may be homogeneous for one or more parameters or characteristics. A plurality that is homogeneous for a given parameter, in some instances, means that particles within the plurality deviate from each other no more than about +/−10%, preferably no more than about +/−5%, and most preferably no more than about +/−1% of a given quantitative measure of the parameter. As an example, the particles may be homogeneously porous. This means that the degree of porosity within the particles of the plurality differs by not more than +/−10% of the average porosity. In other instances, a plurality that is homogeneous means that all the particles in the plurality were treated or processed in the same manner, including for example exposure to the same agent regardless of whether every particle ultimately has all the same properties. In still other embodiments, a plurality that is homogeneous means that at least 80%, preferably at least 90%, and more preferably at least 95% of particles are identical for a given parameter.

The plurality of particles may be heterogeneous for one or more parameters or characteristics. A plurality that is heterogeneous for a given parameter, in some instances, means that particles within the plurality deviate from the average by more than about +/−10%, including more than about +/−20%. Heterogeneous particles may differ with respect to a number of parameters including their size or diameter, their shape, their composition, their surface charge, their degradation profile, whether and what type of agent is comprised by the particle, the location of such agent (e.g., on the surface or internally), the number of agents comprised by the particle, etc. The disclosure contemplates separate synthesis of various types of particles which are then combined in any one of a number of pre-determined ratios prior to contact with the sample. As an example, in one embodiment, the particles may be homogeneous with respect to shape (e.g., at least 95% are spherical in shape) but may be heterogeneous with respect to size, degradation profile and/or agent comprised therein.

Particle size, shape and release kinetics can also be controlled by adjusting the particle formation conditions. For example, particle formation conditions can be optimized to produce smaller or larger particles, or the overall incubation time or incubation temperature can be increased, resulting in particles which have prolonged release kinetics.

The particles may also be coated with one or more stabilizing substances, which may be particularly useful for long term depoting with parenteral administration or for oral delivery by allowing passage of the particles through the stomach or gut without dissolution. For example, particles intended for oral delivery may be stabilized with a coating of a substance such as mucin, a secretion containing mucopolysaccharides produced by the goblet cells of the intestine, the submaxillary glands, and other mucous glandular cells.

The particles may be liposomes or lipid-based carriers. To enhance delivery the particles may be liposomes, virosomes, cationic lipids or other lipid based structures. The term "cationic lipid" refers to lipids which carry a net positive charge at physiological pH. Such lipids include, but are not limited to, DODAC, DOTMA, DDAB, DOTAP, DC-Chol and DMRIE. Additionally, a number of commercial preparations of cationic lipids are available. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA). A variety of methods are available for preparing liposomes e.g., U.S. Pat. Nos. 4,186,183, 4,217,344, 4,235,871, 4,261,975, 4,485,054, 4,501,728, 4,774,085, 4,837,028, 4,946,787; and PCT Publication No. WO 91/17424. The particles may also be composed in whole or in part of GRAS components. i.e., ingredients are those that are Generally Regarded As Safe (GRAS) by the US FDA. GRAS components useful as particle material include non-degradable food based particles such as cellulose.

The carrier domain can serve several functions. As discussed above, it may be useful for targeting the product to a specific region, such as a tissue. In that instance it could include a targeting agent such as a glycoprotein, an antibody, or a binding protein. The carrier domain may also serve as the protecting group.

A protecting group, as used herein, is a group, optionally a small molecule, that protects the enzyme cleavable domain from the protease. The protecting group can be removed by a remote signal, or external force. One the protecting group is removed the protease is able to cleave the sensitive domain and releases the detectable marker. In some embodiments the external force is a magnetic field source, an ultraviolet A (UVA) light source, an alternating magnetic field (AMF) or an infrared light source. The UVA light may be administered via photon upconversion or two-photon technology or via an implantable light source. In some embodiments the protecting group is a photolabile group. A photolabile group in some embodiments is a small molecule responsive to different wavelength activations, 1-(4,5-dimethoxy-2-nitrophenyl) diazoethane (DMNPE), coumarin, benoquinolone, a thermosensitive molecule such as a thermosensitive liposome, a liposomal carrier containing gold nanoparticles, a pH-responsive liposomal nanocarrier or a reactive oxygen-responsive liposomal nanocarrier. In some embodiments, the thermosensitive liposome is a liposome nanocarrier containing magnetic nanoparticles. In some embodiments, the photolabile group is a large molecule that provides greater steric hindrance and therefore greater protection from enzymatic cleavage.

Further, the size of the carrier domain may be adjusted based on the particular use of the biomarker nanoparticle. For instance, the carrier domain may be designed to have a size greater than 5 nm. Particles, for instance, of greater than 5 nm are not capable of entering the urine, but rather, are cleared through the reticuloendothelial system (RES; liver, spleen, and lymph nodes). By being excluded from the removal through the kidneys any uncleaved biomarker nanoparticle will not be detected in the urine during the analysis step.

Additionally, larger particles can be useful for maintaining the particle in the blood or in a tumor site where large particles are more easily shuttled through the vasculature. In some embodiments the carrier domain is 500 microns-5 nm, 250 microns-5 nm, 100 microns-5 nm, 10 microns-5 nm, 1 micron-5 nm, 100 nm-5 nm, 100 nm-10 nm, 50 nm-10 nm or any integer size range therebetween. In other instances the carrier domain is smaller than 5 nm in size. In such instance the biomarker nanoparticle will be cleared into the urine. However, the presence of free detectable marker can still be detected for instance using mass spectrometry. In some embodiments the carrier domain is 1-5 nm, 2-5 nm, 3-5 nm, or 4-5 nm.

Optionally, the carrier domain may include a biological agent. In some embodiments, a biological agent could be incorporated in the carrier domain or it may make up the carrier domain. For instance, it may form the scaffold or platform that the proteolytic domain is attached to. Thus compositions of the disclosure can achieve two purposes at the same time, the diagnostic methods and delivery of a therapeutic agent. In some embodiments, the biological agent may be an enzyme inhibitor. In that instance the biological agent can inhibit proteolytic activity at a local site and the detectable marker can be used to test the activity of that particular therapeutic at the site of action. HIV is an example of the disease in which active proteases can be monitored. In this embodiment the composition may include a micro-particle or other delivery device carrying a protease inhibitor. The protease susceptible site may be sensitive to the HIV proteases such that feedback can be provided regarding the activity of the particular protease inhibitor.

The enzyme susceptible detectable marker is a portion of the modular structure that is connected to the carrier. An enzyme susceptible detectable marker, as used herein, is the portion of the modular structure that promotes the enzymatic reaction in the subject, causing the release of a detectable marker. The enzyme susceptible detectable marker is an enzyme susceptible domain linked to a detectable marker.

The enzyme susceptible site is dependent on enzymes that are active in a specific disease state. For instance, tumors are associated with a specific set of enzymes. If the disease state being analyzed is a tumor then the product is designed with an enzyme susceptible site that matches that of the enzyme expressed by the tumor or other diseased tissue.

Alternatively, the enzyme specific site may be associated with enzymes that are ordinarily present but are absent in a particular disease state. In this example, a disease state would be associated with a lack or signal associated with the enzyme, or reduced levels of signal compared to a normal reference.

An enzyme, as used herein refers to any of numerous proteins produced in living cells that accelerate or catalyze the metabolic processes of an organism. Enzymes act on substrates. The substrate binds to the enzyme at a location called the active site just before the reaction catalyzed by the enzyme takes place. Enzymes include but are not limited to proteases, glycosidases, lipases, heparinases, phosphatases.

The enzyme susceptible site may be optimized to provide both high catalytic activity (or other enzymatic activity) for specified target enzymes but to also release optimized detectable markers for detection. Patient outcome depends on the phenotype of individual diseases at the molecular level, and this is often reflected in expression of enzymes.

The recent explosion of bioinformatics has facilitated exploration of complex patterns of gene expression in human tissues (Fodor, S. A. Massively parallel genomics. Science 277, 393-395 (1997)). Sophisticated computer algorithms have been recently developed capable of molecular diagnosis of tumors using the immense data sets generated by expression profiling (Khan J, Wei J S, Ringner M, Saal L H, Ladanyi M, Westermann F, et al. Classification and diagnostic prediction of cancers using gene expression profiling and artificial neural networks. Nat Med 2001; 7:673-679.). This information can be accessed in order to identify enzymes and substrates associated with specific diseases. Based on this information the skilled artisan can identify appropriate enzyme or substrates to incorporate into the biomarker nanoparticle.

In some embodiments, the enzyme susceptible domain is an enzyme susceptible domain. As used herein, "enzyme susceptible domain" refers to an enzyme susceptible domain that is capable of being cleaved by a protease that is present (or upregulated) in a subject having a disease (e.g., cancer, metastatic cancer, an infection with a pathogenic agent, etc.).

An enzyme susceptible detectable marker may be attached directly to the carrier. For instance it may be coated directly on the surface of nanoparticles using known techniques. Alternatively if the carrier is a protein material it may be directly connected through a peptide bond. Additionally, the enzyme susceptible detectable marker may be connected to the carrier domain through the use of a linker. As used herein "linked" or "linkage" means two entities are bound to one another by any physicochemical means. Any linkage known to those of ordinary skill in the art, covalent or non-covalent, is embraced. Thus, in some embodiments the carrier has a linker attached to an external surface, which can be used to link the enzyme susceptible detectable marker. Another molecule can also be attached to the linker. In some embodiments, two molecules are linked using a transpeptidase, for example Sortase A. If the nanocarrier is a liposome, the enzyme susceptible detectable marker may be incorporated into the liposome using well known teachings.

The enzyme susceptible detectable marker is preferably a polymer made up of a plurality of chemical units. A "chemical unit" as used herein is a building block or monomer which may be linked directly or indirectly to other building blocks or monomers to form a polymer.

The detectable marker is capable of being released from the biomarker nanoparticle when exposed to an enzyme in vivo. The detectable marker once released is free to travel to a remote site for detection. A remote site is used herein to refer to a site in the body that is distinct from the bodily tissue housing the enzyme where the enzymatic reaction occurs. In other words the remote site is a biological 1 sample or tissue that is different than the biological sample where the enzyme susceptible detectable marker is administered and/or where the protease cleaves the molecule. In some embodiments, the bodily tissue housing the enzyme where the enzymatic reaction occurs is the blood or the tissue in a or surrounding a tumor. The remote site in some embodiments is urine.

Modification of the enzyme susceptible domain by an enzyme in vivo, results in the production of a detectable marker. Alternatively, when the enzyme susceptible detectable marker is an enzyme the enzyme cleaves an endogenous substrate producing a detectable marker from the endogenous substrate. In some embodiments, the detectable marker is a detectable molecule. It can be part of the enzyme susceptible domain, e.g. the piece that is released or added upon cleavage or it can be a separate entity. The detectable marker may be composed of two ligands joined by a linker. The detectable marker may be comprised of, for instance one or more of a peptide, nucleic acid, small molecule, fluorophore/quencher, carbohydrate, particle, radiolabel, MRI-active compound, inorganic material, organic material, with encoded characteristics to facilitate optimal detection. The peptide itself may be the detectable maker, as it can be detected in the urine using known methods e.g. as described herein.

In some embodiments, an enzyme susceptible detectable marker that comprises a capture ligand is a molecule that is capable of being captured by a binding partner. The detection ligand is a molecule that is capable of being detected by any of a variety of methods. While the capture ligand and the detection ligand will be distinct from one another in a particular detectable marker, the class of molecules that make us capture and detection ligands overlap significantly. For instance, many molecules are capable of being captured and detected. In some instances these molecules may be detected by being captured or capturing a probe. The capture and detection ligand each independently may be one or more of the following: a protein, a peptide, a polysaccharide, a nucleic acid, a fluorescent molecule, or a small molecule, for example. In some embodiments the detection ligand or the capture ligand may be, but is not limited to, one of the following: Alexa488, TAMRA, DNP, fluorescein, Oregon Green, Texas Red, Dansyl, BODIPY, Alexa405, Cascade Blue, Lucifer Yellow, Nitrotyrosine, HA-tag, FLAG-tag, His-tag, Myc-tag, V5-tag, S-tag, biotin or streptavidin. In some embodiments, the capture ligand and a detection ligand are connected by a linker. The purpose of the linker is prevent steric hindrance between the two ligands. Thus, the linker may be any type of molecule that achieves this. The linker may be, for instance, a polymer such as PEG, a protein, a peptide, a polysaccharide, a nucleic acid, or a small molecule. In some embodiments the linker is a protein of 10-100 amino acids in length. In other embodiments the linker is GluFib (SEQ ID NO. 1). Optionally, the linker may be 8 nm-100 nm, 6 nm-100 nm, 8 nm-80 nm, 10 nm-100 nm, 13 nm-100 nm, 15 nm-50 nm, or 10 nm-50 nm in length.

In some embodiments, the detectable marker is a ligand encoded reporter. Without wishing to be bound by any particular theory, a ligand encoded reporter binds to a target molecule, allowing for detection of the target molecule at a site remote from where the ligand encoded reporter bound to the target. In some embodiments, a ligand encoded reporter binds to a target molecule associated with a pathogenic agent. As used herein, "pathogenic agent" refers to a molecule that is indicative of the presence of a particular infectious agent (e.g., a virus, bacterium, parasite, etc.). Examples of pathogenic agents include viral proteins, bacterial proteins, biological toxins, and parasite-specific proteins (e.g., *S. mansoni* OVA protein).

In some embodiments, a detectable marker is a mass encoded reporter, for example an iCORE as described in WO2012/125808, filed Mar. 3, 2012, the entire contents of which are incorporated herein by reference. Upon arrival in the diseased microenvironment, the iCORE agents interface with aberrantly active proteases to direct the cleavage and release of surface-conjugated, mass-encoded peptide substrates into host urine for detection by mass spectrometry (MS) as synthetic biomarkers of disease.

The detectable marker may be detected by any known detection methods to achieve the capture/detection step. A variety of methods may be used, depending on the nature of the detectable marker. Detectable markers may be directly detected, following capture, through optical density, radioactive emissions, nonradiative energy transfers, or detectable markers may be indirectly detected with antibody conjugates, affinity columns, strepavidin-biotin conjugates, PCR analysis, DNA microarray, and fluorescence analysis.

The capture assay in some embodiments involves a detection step selected from the group consisting of an ELISA, including fluorescent, colorimetric, bioluminescent and chemiluminescent ELISAs, a paper test strip or LFA, bead-based fluorescent assay, and label-free detection, such as surface plasmon resonance (SPR). The capture assay may involve, for instance, binding of the capture ligand to an affinity agent.

The analysis step may be performed directly on the biological sample or the signature component may be purified to some degree first. For instance, a purification step may involve isolating the detectable marker from other components in the biological sample. Purification steps include methods such as affinity chromatography. As used herein an "isolated molecule" or "purified molecule" is a detectable marker that is isolated to some extent from its natural environment. The isolated or purified molecule need not be 100% pure or even substantially pure prior to analysis.

The methods for analysing detectable markers by identifying the presence of a detectable marker may be used to provide a qualitative assessment of the molecule (e.g., whether the detectable marker is present or absent) or a quantitative assessment (e.g., the amount of detectable marker present to indicate a comparative activity level of the enzymes. The quantitative value may be calculated by any means, such as, by determining the percent relative amount of each fraction present in the sample. Methods for making these types of calculations are known in the art.

The detectable marker may be labeled. For example, a label may be added directly to a nucleic acid when the isolated detectable marker is subjected to PCR. For instance, a PCR reaction performed using labeled primers or labeled nucleotides will produce a labeled product. Labeled nucleotides (e.g., fluorescein-labeled CTP) are commercially available. Methods for attaching labels to nucleic acids are well known to those of ordinary skill in the art and, in addition to the PCR method, include, for example, nick translation and end-labeling.

Labels suitable for use in the methods of the present disclosure include any type of label detectable by standard means, including spectroscopic, photochemical, biochemical, electrical, optical, or chemical methods. Preferred types of labels include fluorescent labels such as fluorescein. A fluorescent label is a compound comprising at least one fluorophore. Commercially available fluorescent labels include, for example, fluorescein phosphoramidides such as fluoreprime (Pharmacia, Piscataway, N.J.), fluoredite (Millipore, Bedford, Mass.), FAM (ABI, Foster City, Calif.), rhodamine, polymethadine dye derivative, phosphores, Texas red, green fluorescent protein, CY3, and CY5. Polynucleotides can be labeled with one or more spectrally distinct fluorescent labels. "Spectrally distinct" fluorescent labels are labels which can be distinguished from one another based on one or more of their characteristic absorption spectra, emission spectra, fluorescent lifetimes, or the like. Spectrally distinct fluorescent labels have the advantage that they may be used in combination ("multiplexed"). Radionuclides such as 3H, 125I, 35S, 14C, or 32P are also useful labels according to the methods of the disclosure. A plurality of radioactively distinguishable radionuclides can be used. Such radionuclides can be distinguished, for example, based on the type of radiation (e.g. $\alpha$, ($\beta$, or $\delta$ radiation) emitted by the radionuclides. The 32P signal can be detected using a phosphoimager, which currently has a resolution of approximately 50 microns. Other known techniques, such as chemiluminescence or colormetric (enzymatic color reaction), can also be used.

Quencher compositions in which a "donor" fluorophore is joined to an "acceptor" chromophore by a short bridge that is the binding site for the enzyme may also be used. The signal of the donor fluorophore is quenched by the acceptor chromophore through a process believed to involve resonance energy transfer (RET). Cleavage of the peptide results in separation of the chromophore and fluorophore, removal of the quench, and generation of a subsequent signal measured from the donor fluorophore.

The disease or condition assessed according to the methods of the disclosure is any disease or condition that is associated with an enzyme. For instance, cancer, cardiovascular disease, arthritis, viral, bacterial, parasitic or fungal infection, Alzheimer's disease emphysema, thrombosis, hemophilia, stroke, organ dysfunction, any inflammatory condition, vascular disease, parenchymal disease, or a pharmacologically-induced state are all known to be associated with enzymes. A pharmacologically induced state is a condition in which enzyme inhibitors and other agents directly or indirectly affect enzyme activities. Thus each of the these can be assessed or monitored or studied according to methods of the disclosure.

It is useful to be able to differentiate non-metastatic primary tumors from metastatic tumors, because metastasis is a major cause of treatment failure in cancer patients. If metastasis can be detected early, it can be treated aggressively in order to slow the progression of the disease. Metastasis is a complex process involving detachment of cells from a primary tumor, movement of the cells through the circulation, and eventual colonization of tumor cells at local or distant tissue sites. Additionally, it is desirable to be able to detect a predisposition for development of a particular cancer such that monitoring and early treatment may be initiated. For instance, an extensive cytogenetic analysis of hematologic malignancies such as lymphomas and leukemias have been described, see e.g., Solomon et al., Science 254, 1153-1160, 1991. Early detection or monitoring using the non-invasive methods of the disclosure may be useful.

Solid tumors progress from tumorigenesis through a metastatic stage and into a stage at which several different active proteases can be involved. Some protease are believed to alter the tumor such that it can progress to the next stage, i.e., by conferring proliferative advantages, the ability to develop drug resistance or enhanced angiogenesis, proteolysis, or metastatic capacity.

Accordingly, in some aspects, the disclosure provides a method for determining metastatic stage of a tumor comprising administering to the subject having a tumor a biomarker nanoparticle, wherein the biomarker nanoparticle comprises a modular structure having a carrier domain linked to an enzyme susceptible detectable marker, wherein the enzyme susceptible detectable marker is comprised of an enzyme susceptible domain linked to a detectable marker whereby the detectable marker is capable of being released from the biomarker nanoparticle when exposed to a metastatic tumor-associated enzyme; obtaining a urine sample from the subject for detection of the detectable marker; and, analyzing the urine sample using a capture assay in order to detect the presence of the detectable marker, wherein the presence of the detectable marker in the urine sample is indicative of the subject having a metastatic tumor.

In some embodiments, a protease detected by methods and compositions described herein is associated with a pathogenic agent and is thus indicative of infection in a subject. Accordingly, in some aspects, the disclosure provide a method for identifying a pathogenic agent comprising administering to the subject infected or suspected of being infected with a pathogenic agent a biomarker nanoparticle, wherein the biomarker nanoparticle comprises a modular structure having a carrier domain linked to an enzyme susceptible detectable marker, wherein the enzyme susceptible detectable marker is comprised of an enzyme susceptible domain linked to a detectable marker whereby the detectable marker is capable of being released from the biomarker nanoparticle when exposed to an enzyme associated with a pathogenic agent; obtaining a urine sample from the subject for detection of the marker; and, analyzing the urine sample using a capture assay in order to detect the presence of the detectable marker, wherein the presence of the detectable marker in the urine sample is indicative of the subject being infected with the pathogenic agent.

Examples of infectious diseases that can be detected by methods and compositions of the disclosure include but are not limited to bacterial infections, viral infections, fungal infections, and parasitic infections.

Compositions described herein can be administered to any suitable subject. As used herein, a subject is a human, non-human primate, cow, horse, pig, sheep, goat, dog, cat, or rodent. In all embodiments human subjects are preferred. In aspects of the disclosure pertaining to cancer diagnosis in general, the subject preferably is a human suspected of having cancer, or a human having been previously diagnosed as having cancer. Methods for identifying subjects suspected of having cancer may include physical examination, subject's family medical history, subject's medical history, biopsy, or a number of imaging technologies such as ultrasonography, computed tomography, magnetic resonance imaging, magnetic resonance spectroscopy, or positron emission tomography.

As used herein, a biological sample is a tissue sample. The biological sample may be examined in the body, for instance, by detecting a label at the site of the tissue, i.e. urine. Alternatively the biological sample may be collected from the subject and examined in vitro. Biological samples include but are not limited to urine, blood, saliva, or mucous secretion. In preferred embodiments the tissue sample is obtained non-invasively, such as the urine.

A "plurality" of elements, as used throughout the application refers to 2 or more of the elements.

The biomarker nanoparticles of the disclosure are administered to the subject in an effective amount for detecting enzyme activity. An "effective amount", for instance, is an amount necessary or sufficient to cause release of a detectable level of detectable marker in the presence of an enzyme. The effective amount of a compound of the disclosure described herein may vary depending upon the specific compound used, the mode of delivery of the compound, and whether it is used alone or in combination. The effective amount for any particular application can also vary depending on such factors as the disease being assessed or treated, the particular compound being administered, the size of the subject, or the severity of the disease or condition as well as the detection method. One of ordinary skill in the art can empirically determine the effective amount of a particular molecule of the disclosure without necessitating undue experimentation. Combined with the teachings provided herein, by choosing among the various active compounds and weighing factors such as potency, relative bioavailability, patient body weight, severity of adverse side-effects and preferred mode of administration, an effective regimen can be planned.

Pharmaceutical compositions of the present disclosure comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The agent may comprise different types of carriers depending on whether it is to be administered in solid, liquid or aerosol form, and whether it need to be sterile for such routes of administration as injection.

Preferably the material is injected into the body but could also be administered by other routes. For instance, the compounds of the present disclosure can be administered intravenously, intradermally, intraarterially, intralesionally, intratumorally, intracranially, intraarticularly, intraprostatically, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference).

EXAMPLES

Example 1: Photoactivated Spatiotemporally-Responsive Nanosensors of In Vivo Protease Activity Biological function is context dependent, with diverse regulatory mechanisms that function at the transcriptional, translational, and post-translational levels to modulate both the abundance and functional status of proteins. Therefore, the capacity to make dynamic measurements of protein function is crucial in achieving a thorough understanding of biological processes. Proteases are a key example of a protein family that needs to be studied at the activity level due to their extensive post-translational modifications, presence of endogenous inhibitors (e.g., R2-macroglobulin) and pivotal roles played by these proteins in the bioregulation of healthy and disease processes. In the case of cancer biology, both the intratumoral localization and the dynamics of protease activity throughout disease progression are relevant to pathogenesis. Therefore, activity-based measurements that can capture this spatiotemporal heterogeneity may provide important insights.

Numerous techniques have been developed to measure protease activity in models of cancer, including activity-based probes that can assess levels of active enzymes by irreversible binding of a chemical probe. These probes enable the high-content analysis of enzymes, but applying these tools in vivo is technically challenging. Protease-driven imaging of diseased sites, where protease activity results in an increase in contrast, has also shown great promise for early and specific detection of tumor burden. Multiple groups have leveraged these two approaches for nanoparticle (NP)-based protease sensing, using scaffolds such as quantum dots and gold NPs, to achieve improved sensitivity and targeting. A class of activity-based probes called "synthetic biomarkers" that produce a detection signal following protease cleavage similar to fluorigenic probes has been previous reported. In contrast to other platforms, however, the system is designed such that the liberated peptide fragments are concentrated in the urine and detectable by a variety of analytical techniques ranging from mass spectrometry to single molecule assays. As the function of these systems is initiated by an active protease, the measurements collected reflect protease activity rather than abundance. While each of these activity-based approaches are promising, they lack the ability to be remotely controlled.

Example 2: Development of Spatiotemporally Responsive Nanoparticle Protease Sensors Matrix metalloproteinases (MMPs) represent an important protease family to study and assay as their activities are associated with numerous pathways in health and disease. Thus, a veiled, MMP-sensitive nanosensor by conjugating the photolabile small molecule 1-(4,5-dimethoxy-2-nitrophenyl) diazoethane (DMNPE) to protease cleavable substrates was designed (FIG. 1). DMNPE reacts with acidic groups and, by coupling it to an MMP substrate sequence containing free carboxylic acid side chains, serves as a removable barrier to block enzymatic cleavage. Furthermore, based on previous studies, it was thought that DMNPE should be located within a few amino acids from the putative cleavage site in order to effectively block protease activity by steric hindrance. Based on these design criteria, a peptide sequence that is sensitive to MMP activity (sequence: PLGLEEA; SEQ ID NO: 2) and contains carboxylic acid side chains adjacent to the scissile bond (G-L) was selected. Iron oxide NPs (diameter~100 nm; FIG. 6A) with fluorescein-conjugated peptide substrates (sequence: FAM-sk-PLGLEEA-GC; SEQ ID NO: 3; lower case=D-stereoisomer; name: C1) at a surface valency>20 were functionalized (FIGS. 1, 6B). The size of the NP is larger than the kidney filtration limit and therefore acts to prevent urinary filtration of the STREAMs construct prior to peptide cleavage for applications in vivo. DMNPE was selectively removed after photolysis in the presence of 365 nm light, making the peptide substrate avail-able for cleavage by proteases and resulting in the release of reporters (FIG. 1). Thus, these constructs have the potential to enable spatiotemporal control of the accessibility of the substrate during measurements of protease activity. Since MMP activity is commonly implicated in cancer progression,[5] the utility of these STREAMs in both in vitro and in vivo models of cancer was tested.

STREAMs are designed to leverage the strengths of numerous techniques, such that the unique combination of photolabile chemistry, NP formulation, and protease sensing enables STREAMs to perform the complex task of measuring in vivo enzyme activity with spatial and temporal control. Previous demonstrations of protease measurements in vivo lack external control (e.g., controlled triggering at the tumor site), and the addition of these traits with the STREAM platform may enable greater sensitivity and tumor contrast. Similarly, synthetic biomarkers are vulnerable to background activation in circulation. The previous utilizations of DMNPE have been varied, ranging from caging nucleic acids (DNA and RNA) to caging $Ca2_{\flat}$. However, a general strategy for caging peptide substrates of proteases has not been previously described.

Example 3: Chemical Characterization of Peptide-DMNPE Conjugates

Prior to applying the STREAMs to assay for MMP activity, the chemical conjugation of the photolabile DMNPE group to the MMP substrate was validated. DMNPE is comprised of a nitrophenyl group that is efficiently activated by 365 nm light, resulting in photolysis of the veiled substrate. DMNPE reacts with weak oxo-acids and thus can modify the glutamic acids that reside at the substrate's $P2^0$ and $P3^0$ positions, located toward the C-terminal end of the scissile bond (FIG. 2A). The synthesis of the fluorescein-conjugated peptide (C1) was validated by MALDI mass spectrometry, which resulted in a major peak at 1461.43 m/z that corresponded with the calculated molecular weight of C1 (FIG. 2B). Next, the location of the scissile bond (between the glycine and leucine) was validated by incubating C1-NPs with recombinant MMP9 overnight and measured the size of the N-terminal cleavage fragment (FIG. 2C). DMNPE was incorporated into peptides using a modification of the approach of Friedman and co-workers for modifying insulin. To validate the coupling of DMNPE to the peptide, ESI-MS was used to analyze the conjugate because electrospray ionization does not lead to photolysis of DMNPE. Mass spectrometry analysis of the conjugate resulted in a mass shift associated with DMNPE coupled to the peptide (FIG. 2D, top). Next, MALDI, where ionization is based on UV light pulses, was used to simultaneously photolyze the DMNPE molecules and detect the uncaged peptide backbone. Indeed, the laser desorption resulted in a mass shift of the treated sample to yield a peak at the predicted peptide mass with no evidence of the parent mass, demonstrating that DMNPE could be efficiently photolyzed and removed upon exposure to light (FIG. 2D, bottom).

Figure 7A:
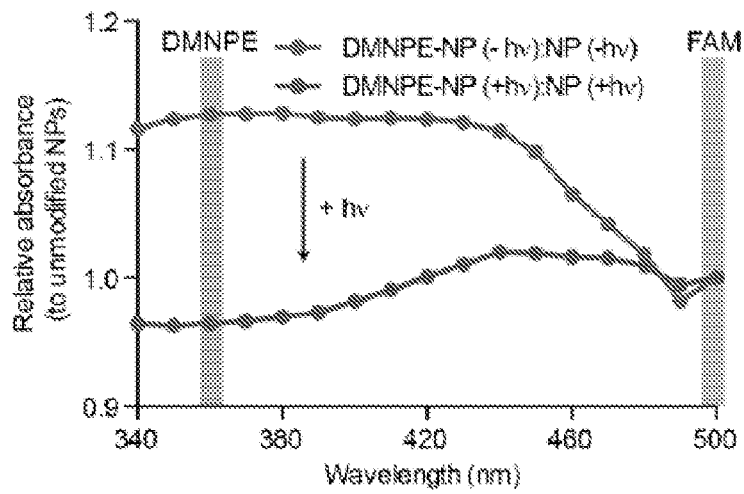
FIGS. 7A-7C shows nanoparticle and photolabile group characterization.

After successfully coupling the photolabile group to the MMP substrate/reporter backbone, the DMNPE groups were directly coupled to the conjugated C1-NPs. Uncoupled DMNPE was removed via spin filtration or FPLC, and successful conjugation of DMNPE was confirmed by shifts in absorbance values (FIG. 2E). Following conjugation of DMNPE with peptides, NPs should exhibit significant absorption at 300-350 nm, which would result in an overall absorbance shift, relative to that of unmodified NPs that should be reversed after photolysis. Consistent with this expectation, after light exposure, STREAMs exhibited an absorption peak that shifted back to overlap with that of preconjugated particles, demonstrating that DMNPE was released from the peptides (FIG. 7A).

Figure 7B:
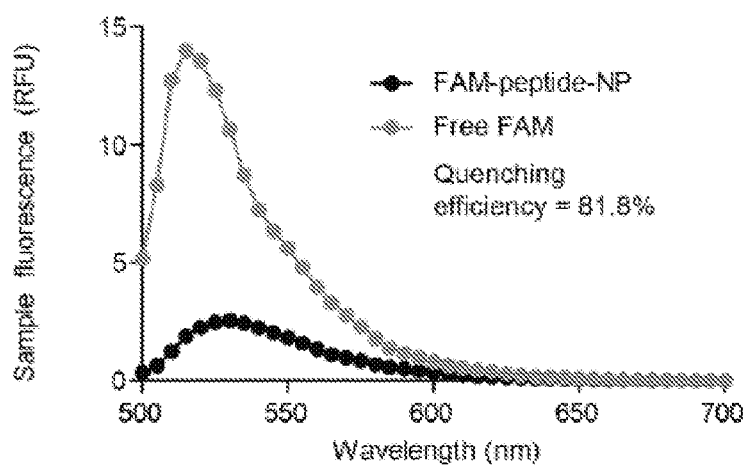
Figure 7C:
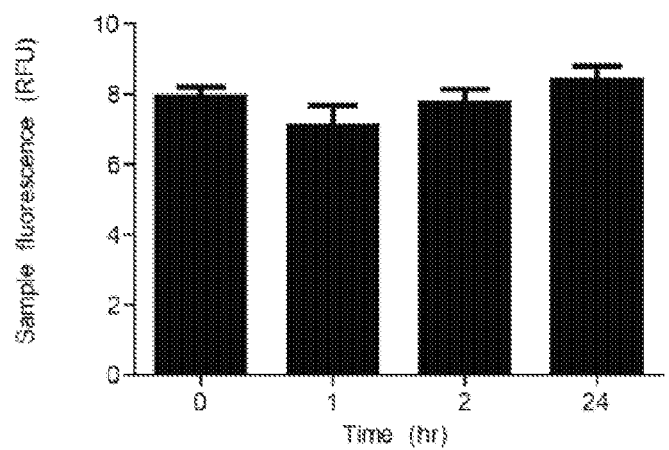

Example 4: STEAMs are Protected from Recombinant Proteases Until Photoactivation Next, whether STREAMs could provide both spatial and temporal control of MMP activity measurements was tested. First, whether the veiled NPs would block protease cleavage until activation by light was evaluated. Due to homoquenching of the fluorescent substrates once assembled on the NPs, protease activity can be monitored by measuring increases in sample fluorescence that occurs from peptide proteolysis (FIG. 7B). NPs were stable in physiological solution at 37° C. over 24 h, as confirmed by a lack of fluorescent dequenching (FIG. 7C).

Figure 3G:
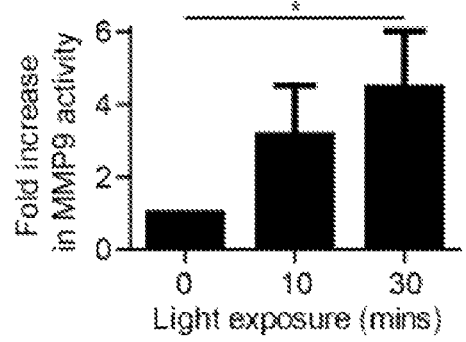
Figure 3H:
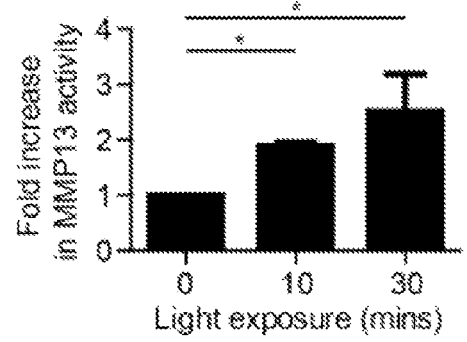
Figure 9A:
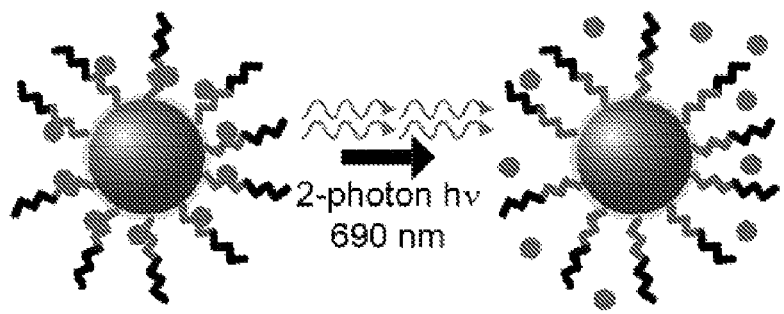
FIGS. 9A-9C show STREAMs can be unveiled by two-photon light.
Figure 9B:
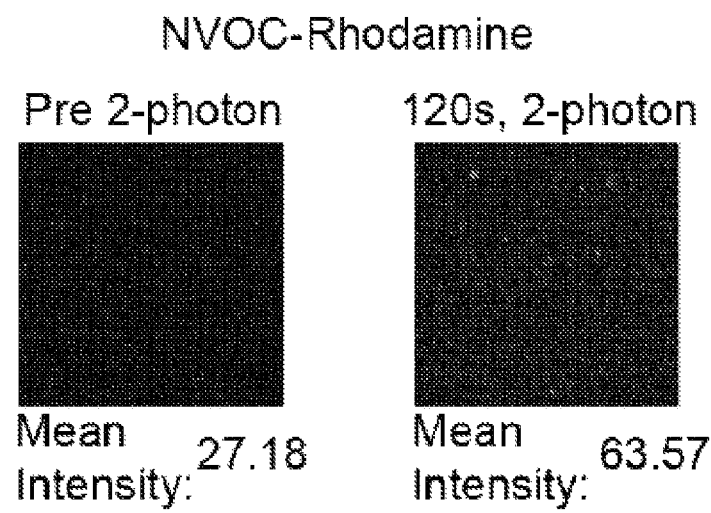
Figure 9C:
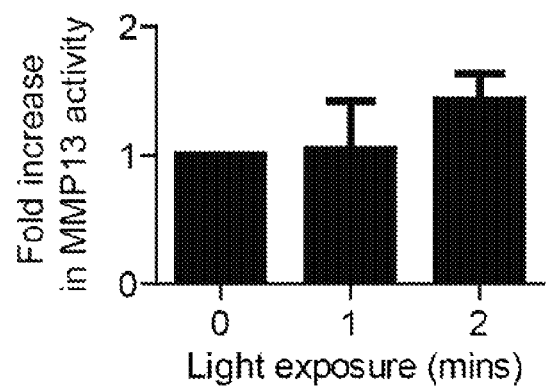

Proteolytic kinetics can be altered by presentation of peptides on surfaces. Therefore, measurements of proteolysis by recombinant enzymes were performed with the substrate on the particle, in the same formulation used in vivo, to accurately capture differences due to presentation. Proteolysis of this substrate was profiled by a panel of proteases consisting of MMPs, ADAMs, and blood-borne proteases. The unmodified substrate (C1-NP) was observed to be significantly cleaved by MMP13, 7, 1, and 9 (FIGS. 3A, 3B, 8A). It is important to note, however, that some of the differences observed in enzyme-mediated substrate cleavage across enzymes may be due in part to the activity of the recombinant enzymes in vitro. Proteolysis by MMP7 was inhibited in the presence of Marimastat, an MMP inhibitor (FIG. 8B). Substrate concentration dependence on cleavage velocity was confirmed for MMP9 and MMP13, and data were fit to the Michaelis-Menten equation, with catalytic efficiencies>$10^3$ $M^{-1}$ $s^{-1}$ and $10^4$ $M^{-1}$ $s^{-1}$, respectively (FIGS. 3C, 3D). In contrast, conjugation with DMNPE resulted in a marked reduction in proteolysis, protecting STREAMs from MMP13 and MMP9 activity (FIGS. 3E, 3F). Stability of DMNPE-peptide-NP STREAM complexes was confirmed by testing samples two weeks post-DMNPE-coupling for resistance to MMP9-mediated cleavage (FIG. 8C), where equal levels of protection compared to freshly conjugated samples were observed. Finally, it was established that exposure of DMNPE-veiled NPs to 365 nm light unveiled the scissile bond and rendered it susceptible to proteolytic cleavage by incubating NPs with MMP9 and MMP13 after increasing periods of exposure to light, which led to elevated proteolysis in a light exposure-dependent manner (FIGS. 3G, 3H). This dose response relationship between light exposure and enzyme-mediated proteolysis indicated that, in some embodiments, it is possible to tune the fraction of photolabile groups that are released and thus enable graded control for use in dynamic and repeated measurements. Furthermore, to extend the utility of this approach, unveiling of STREAMs with two-photon excitation was demonstrated, which, in some embodiments, enables deeper tissue penetration due to the near-infrared optical window (FIG. 9). These results highlight STREAMs as a framework for adding spatiotemporal control to protease-activity measurements.

Figure 10A:
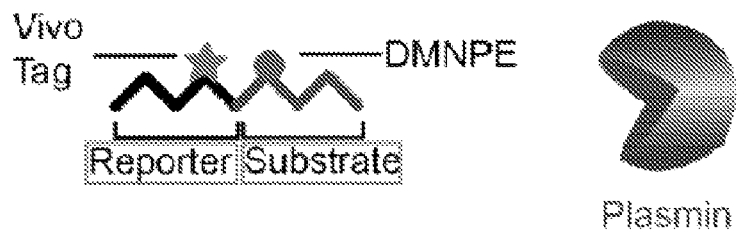
FIGS. 10A-10C show an application of photolabile group to an alternate substrate.
Figure 10B:
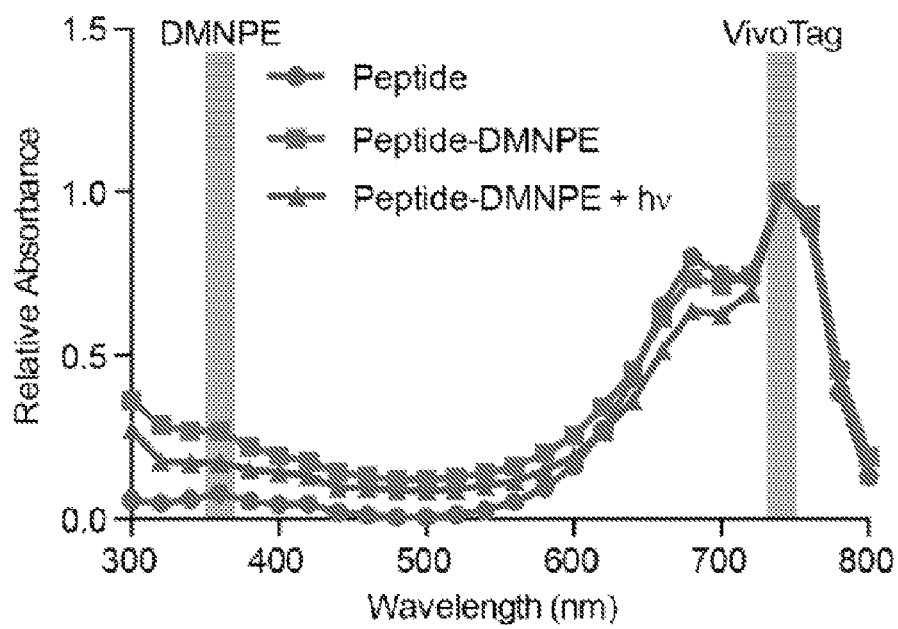
Figure 10C:
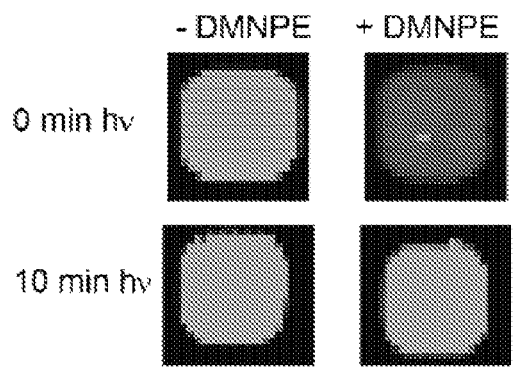

To validate that the approach is generalizable to alternative substrates, the STREAMs principle was applied to a second peptide sequence. Additionally, the reporter for this additional sequence was designed to be orthogonal to the original sequence (containing a near IR dye as opposed to fluorescein). Coupling of DMNPE to this second substrate (RLVGEGC; SEQ ID NO: 15) reduced proteolysis by plasmin, which was recovered by UV exposure (FIG. 10). The ability to produce STREAMs with orthogonal reporters for multiple substrate targets, in some embodiments, enables multiplexing. Additionally, coupling this approach with alternate modes for multiplexing analyte detection, in some embodiments, enables simultaneous monitoring of several substrates.

Figure 11A:
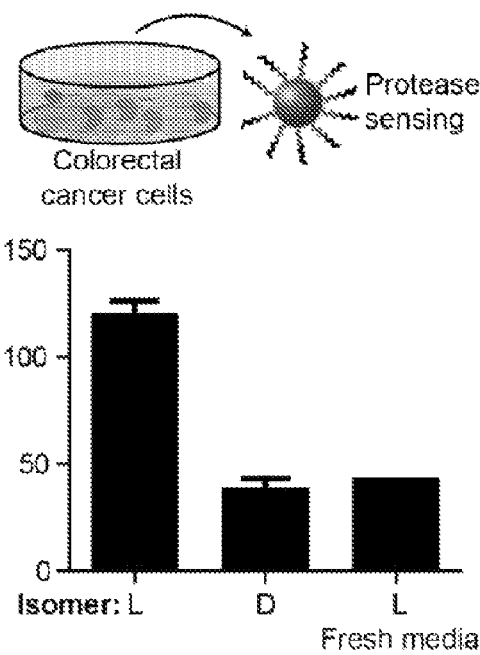
FIGS. 11A-11C show that cellular proteases can cleave protease sensors.
Figure 11B:
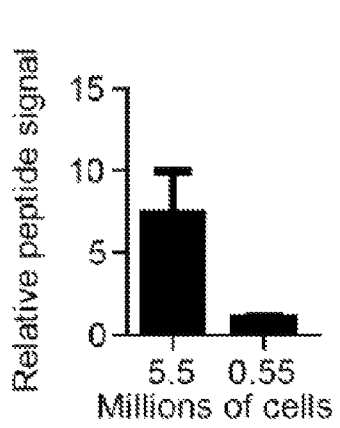
Figure 11C:
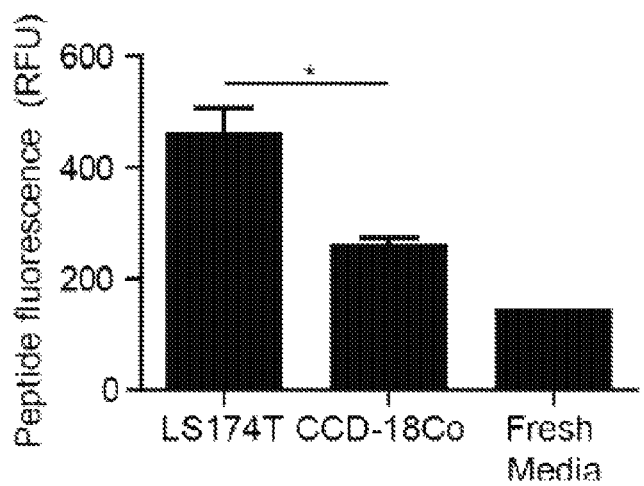

Example 5: STREAMs are Spatiotemporally Responsive Protease Sensors in 3D Cancer Models To investigate whether STREAM constructs might be applied in more complex settings, their performance as proteolysis sensors in a 3D cancer model in vitro was assayed. The LS174T cell line, which has been used extensively for in vivo cancer models and is known to secrete active MMPs (including MMP2, 9) was selected. In order to confirm that the nanosensors were responsive to secreted proteases, fluorigenic C1-NPs were incubated with conditioned media from LS174T cells grown on tissue culture plastic, which resulted in peptide cleavage and a dose-dependent increase in fluorescence that was specific for the L-amino acid version of the protease sensor. By contrast, control NPs conjugated to D-amino acid stereoisomers, which are not cleavable by proteases, were not cleaved by cell-secreted proteases present in conditioned media (FIGS. 11A, 11B). Protease activity derived from the CCD-18Co cell line, which is a line of nontransformed cells isolated from normal colon tissue that has been used previously as a control in cancer studies was also measured. Protease cleavage from these cells, while detectable, was significantly lower compared to LS174T cells (FIG. 11C).

Figure 4C:
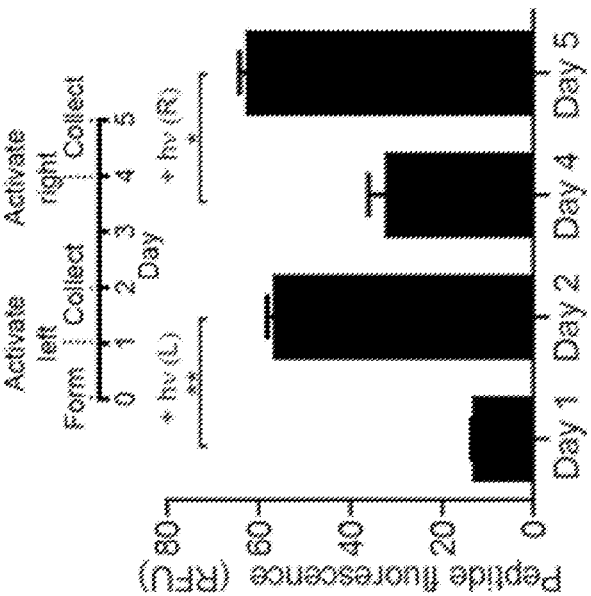
FIGS. 4A-4C shows STREAMs embedded in cancer tissue models for protease sensing.
Figure 4B:
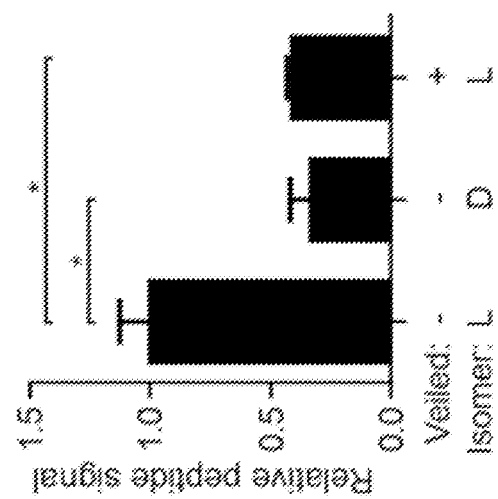
Figure 4A:
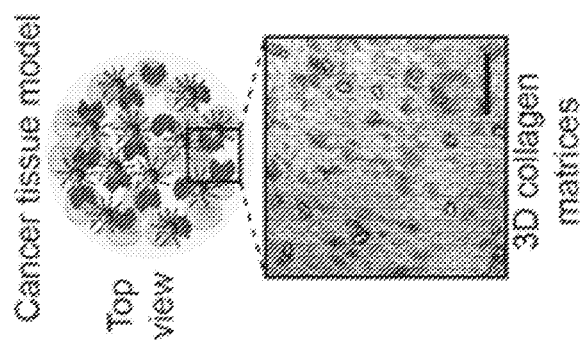

Next, the activation of the nanosensors in a 3D ECM environment was probed. Forty LS174T cells were embedded in collagen I together with veiled or unmodified nanosensors (FIG. 4A). The constructs were monitored for protease activity by collecting the supernatant and measuring liberated peptide fragments under different conditions: L-amino acid peptide substrates were compared to D-amino acid counterparts to measure nonspecific background, and the role of DMPNE veiling was measured. On the first day, constructs bearing L-amino acid sensors released significantly more fluorescent peptides than those with D-amino acid NPs. Additionally, DMNPE-veiled, L-amino acid sensors produced significantly less peptide fluorescence compared to unmodified L-amino acid sensors, indicating that the photolabile groups shielded the NPs from proteolytic cleavage in the context of cell-secreted proteases (FIG. 4B).

Figure 12A:
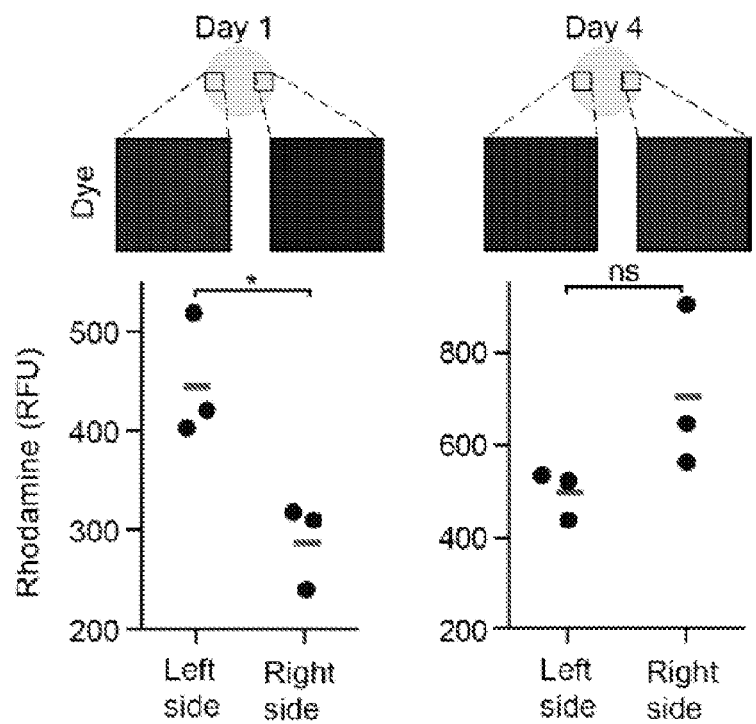
FIGS. 12A-12B show the characterization of a collagen cancer model.
Figure 12B:
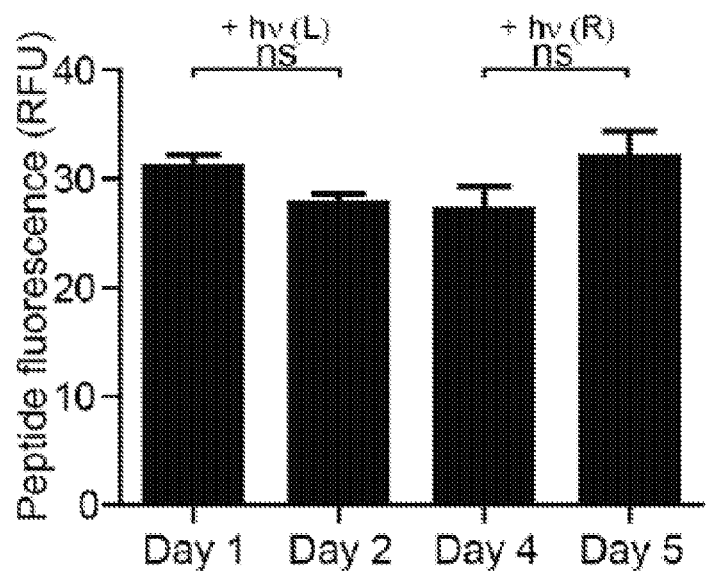

In order to correlate regions of light-activation with protease activity measurements, light-activated rhodamine dye was included to visualize regions exposed to light (FIG. 12A). To explore the ability to monitor protease activity with spatial and temporal control, only the left half of the gels was illuminated. After 24 h, the supernatant surrounding the gels contained higher levels of peptide fluorescence, indicating that restricted light activation unveiled peptides and made them available for proteolysis (FIG. 4C) Similarly, when the opposite side of the cancer tissue model was illuminated 3 days later, a significant increase in fluorescent reporters released was observed. By contrast, unmodified sensors did not exhibit significant changes in peptide fluorescence after UV exposure (FIG. 12B). Collectively, these results demonstrate that STREAMs can be used to spatially probe enzyme activity in engineered constructs.

Example 6: STREAMs are Protected from In Vivo Proteases Until Photoactivated

Having established that STREAMs can be used to spatially and temporally detect cancer cell-derived MMP activity, a method to measure protease activity in vivo was derived. First, whether DMNPE-veiled STREAMs were protected in the context of the enzyme milieu present in living animals was examined. To this end, the STREAM paradigm was adapted for use with the synthetic biomarker platform recently developed, which provides a urinary readout of in vivo proteolysis. Synthetic biomarkers are comprised of peptide-reporter tandem conjugates that are coupled to a NP core. These protease nanosensors are infused intravenously and passively accumulate at sites of disease. Proteolysis of the peptide substrate liberates the reporter, which accumulates in the urine and can be quantified by mass spectrometry or ELISA.

Figure 13:
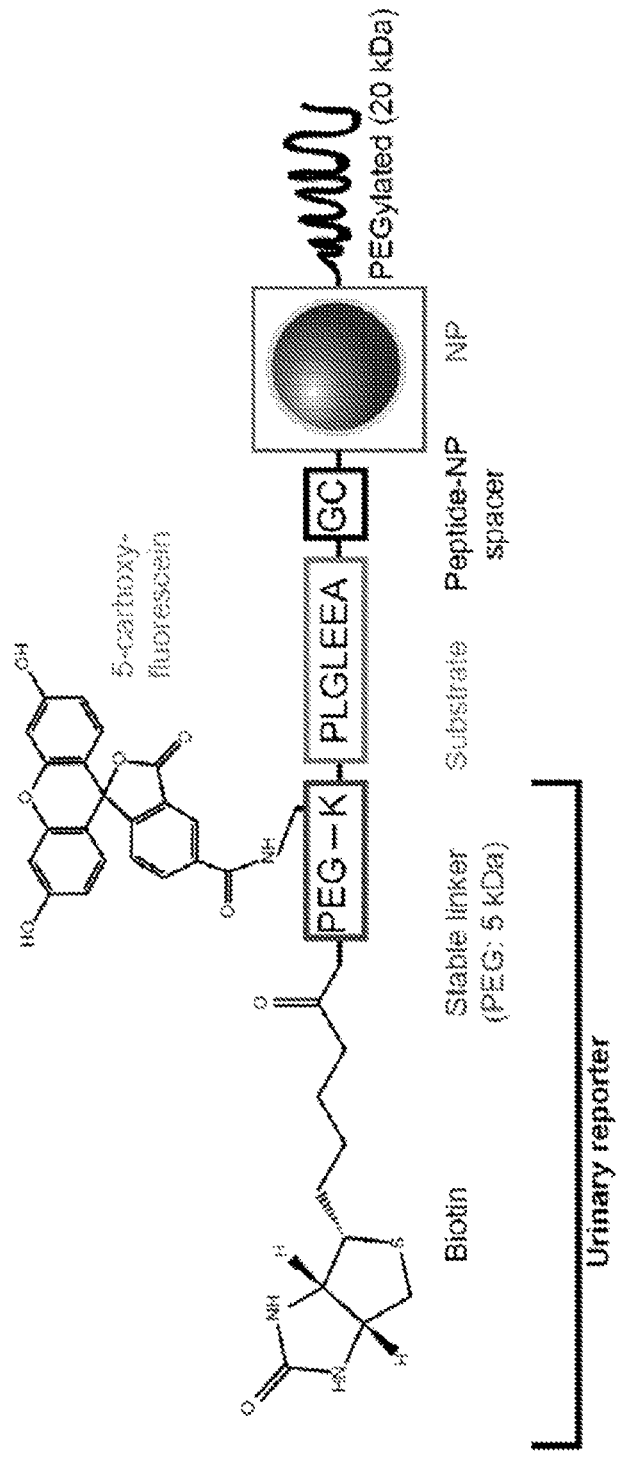
FIG. 13 shows the design of in vivo STREAM synthetic biomarkers. The in vivo protease sensor (V1-NPs) is comprised of a urinary reporter that clears through kidney into urine where it can be detected using a customized sandwich ELISA, coupled to the substrate. The sequence corresponds to SEQ ID NO: 13.
Figure 14A:
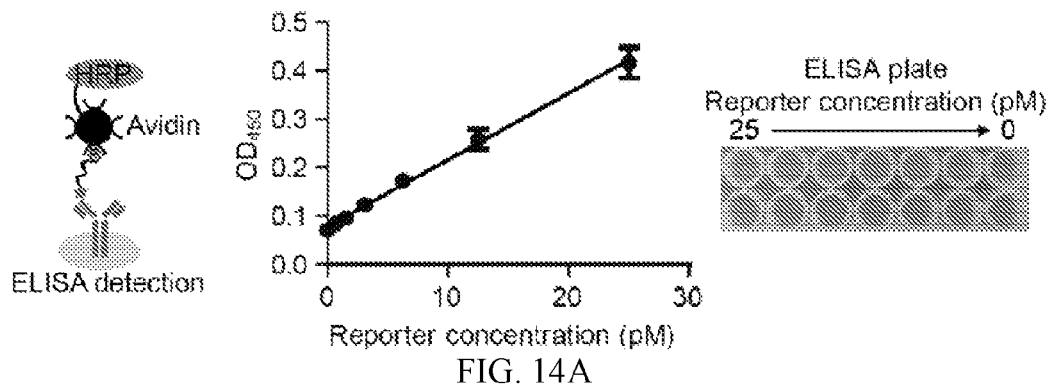
FIGS. 14A-14C show in vivo assay analysis.

For the in vivo studies, previous approaches for engineering ligand-encoded urinary reporters and companion ELISAs were utilized. This urinary reporter is comprised of a poly(ethylene-glycol) element (PEG; 5 kDa) that efficiently clears into the urine and bears a fluorescein group and a biotin, enabling detection in the urine via a sandwich ELISA for the reporter (sequence: Biotin-PEG(5 kDa)-(KFAM)-PLGLEEA-GC; SEQ ID NO: 4; reporter: Biotin-PEG(5 kDa)-(KFAM); name: V1). This reporter element is released upon proteolysis and clears into the urine for quantification (FIG. 13). The custom sandwich ELISA exhibited high sensitivity, as it detected low picomolar concentrations of the reporter (FIG. 14A). This peptide-reporter element is coupled to PEGylated (20 kDa) NPs and modified with DMNPE in the same manner as in vitro STREAMs. All in vivo experiments were performed with the V1 substrate coupled to NPs.

Figures 5A, 5B:
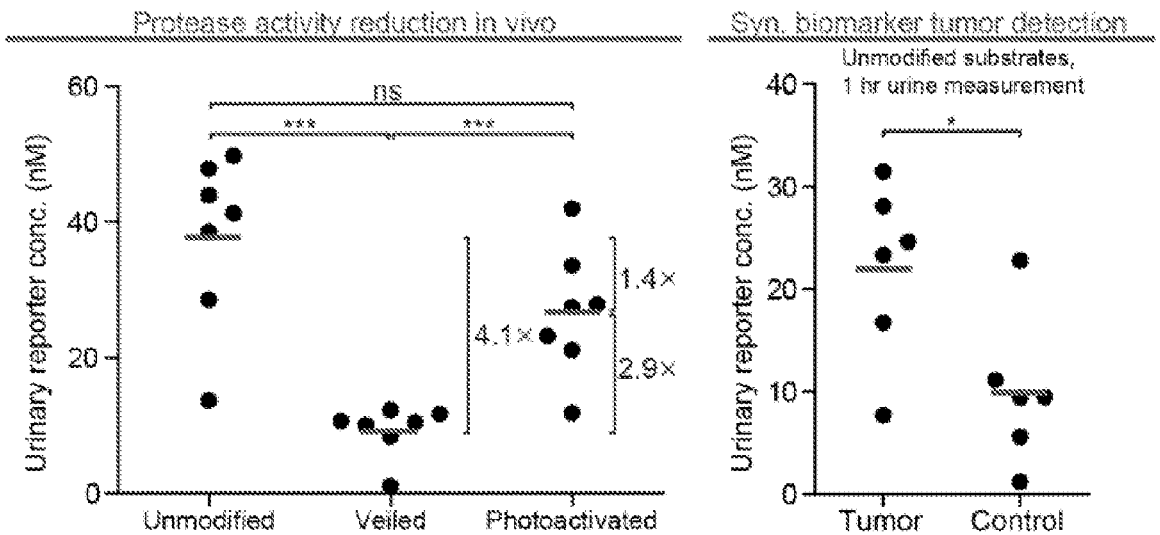
FIGS. 5A-5C shows in vivo STREAMs for urinary measurements of protease activity.
Figure 14B:
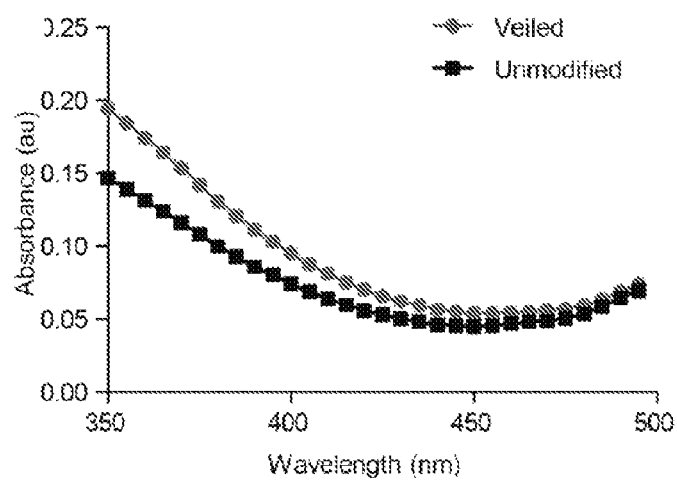
Figure 14C:
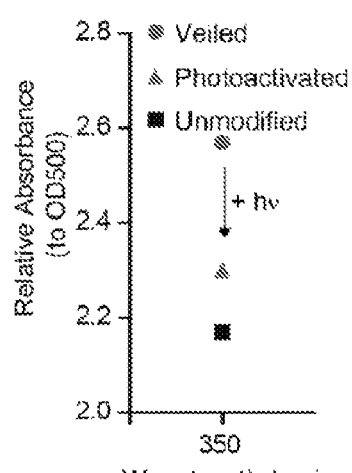
Figure 15:
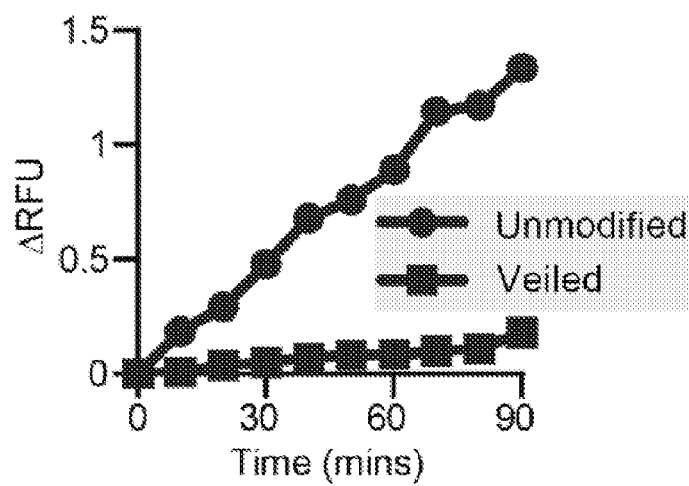
FIG. 15 shows STREAMs are protected from non-specific cleavage by thrombin. Recombinant thrombin, a representative blood protease, elicits reduced proteolysis of the veiled sensors enabling a decrease in background blood signal. C1-NPs (unmodified or veiled) were exposed at the same concentration to thrombin and cleavage was monitored by fluorescence release.

To assay their performance in vivo, equivalent concentrations (by peptide) of unmodified synthetic biomarkers and STREAM synthetic biomarkers were injected intravenously into healthy Swiss Webster mice (FIG. 14B), and urine was collected 30 min after NP infusion. A significant decrease in the reporter release from STREAM synthetic biomarkers (>4-fold) in healthy mice was observed (FIG. 5A). To confirm that the protecting group modification was the source of the dampened urinary signal, in a separate cohort of animals, STREAMs that were preactivated ex vivo to induce photolysis of DMNPE were infused (FIG. 14C) and observed that the majority of the signal reduction associated with veiled peptides was lost (~3-fold recovery). The observation that veiled particles yield a lower urine signal in healthy animals indicated that STREAM synthetic biomarkers are protected from cleavage in circulation. This observation was validated by incubating veiled C1-NPs with recombinant thrombin, an ubiquitous plasma protease essential for blood clotting, and noting reduced cleavage of the substrate (FIG. 15). Thus, the application of STREAMs to protease-sensitive synthetic biomarkers has the potential to enable improved specificity in protease measurements by localizing the sites of activation.

Example 7: Photoactivated STREAMs Measure Protease Activity in the Tumor Microenvironment With the adaptation of STREAMs for use in vivo, the platform was utilized to interrogate protease activity of the tumor microenvironment. Since the V1 peptide had yet to be validated within the synthetic biomarker framework to detect cancer, its capacity to distinguish healthy mice from those bearing bilateral flank human colorectal cancer xenografts was first tested. Previous work identified an optimal time frame in which to perform urinary measurements to achieve signal separation between tumor-bearing and healthy mice. At early time points (minutes), signal is primarily generated by blood-borne protease activity as NPs need longer periods in order to accumulate at the tumor site via the enhanced permeability and retention effect. At later time points (hours), the vast majority of administered substrates have been consumed in both tumor and healthy controls, dampening any distinguishable signal between the two groups. Therefore, with an optimized time point of 1 h post-administration of V1-NPs, a significantly higher reporter signal was present in the urine of tumor-bearing mice 1 h after infusion, validating the use of this peptide as a synthetic biomarker for cancer (FIG. 5B).

Figure 16A:
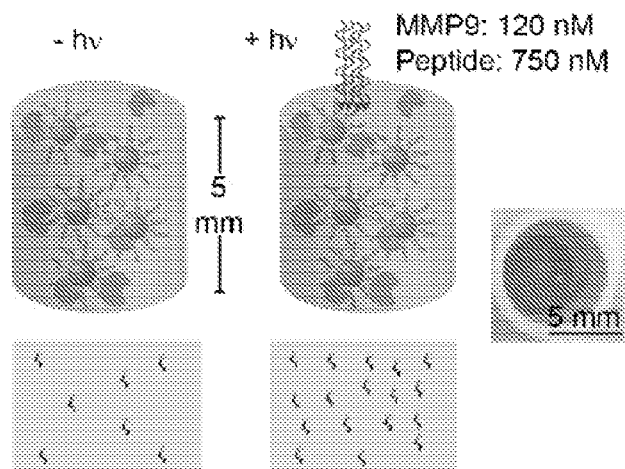
FIGS. 16A-16C present a 3D agarose hydrogel demonstration.
Figure 16B:
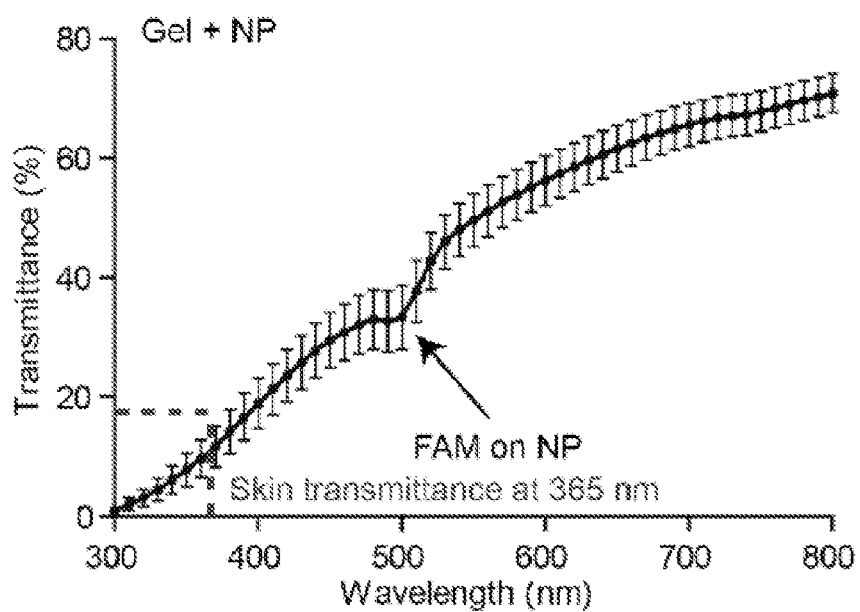
Figure 16C:
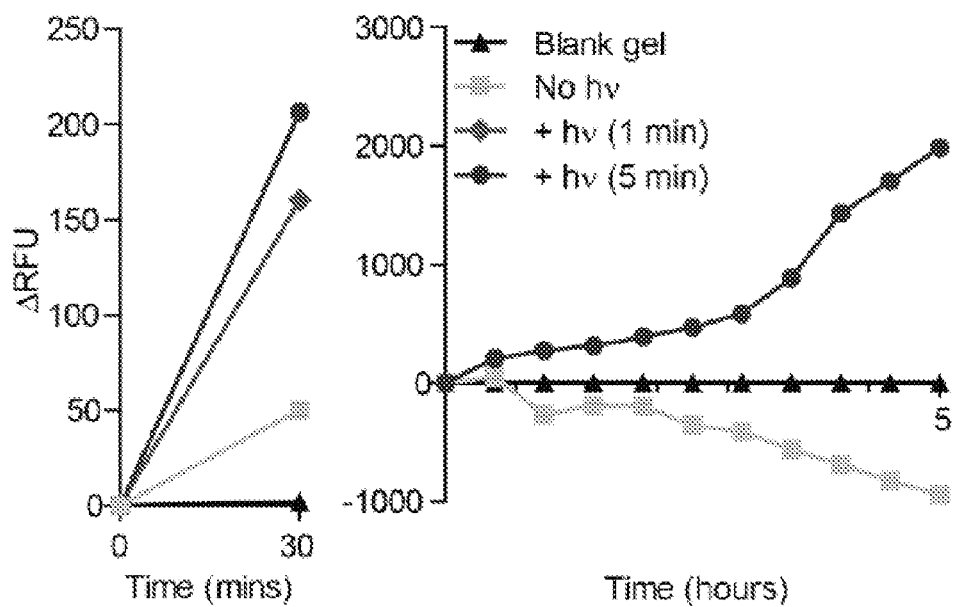

The levels of tumor-associated protease activity in vivo, via transdermal activation of STREAMs, were next detected. It was first necessary to confirm that light penetration through skin is adequate to activate STREAMs. To this end, an agarose gel embedded with recombinant MMP9 and STREAMs was developed (FIG. 16A) with similar transmittance at 365 nm as skin (10% vs 17%; 44 FIG. 16B). A brief light exposure (1 min) of the gel resulted in dramatic increase in proteolytic cleavage of the sensors, indicating that transdermal activation is feasible in vivo (FIG. 16C).

Figure 5C:
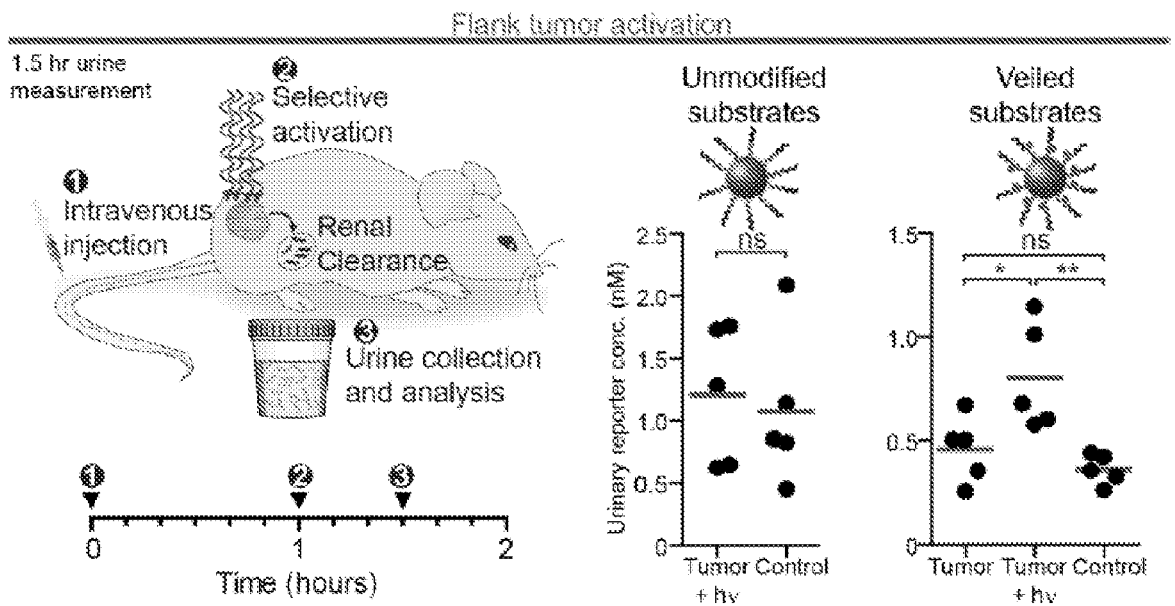
Figure 17:
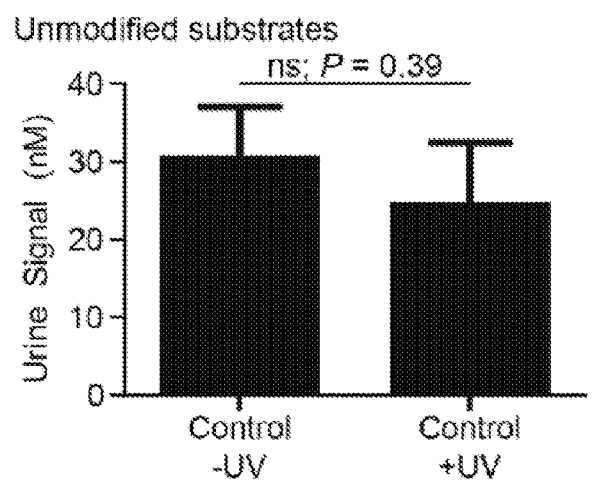
FIG. 17 shows that UV exposure does not affect the urinary signal. Healthy nude mice were exposed to UV as before and then infused with unmodified synthetic biomarkers. Urine was collected 30 minutes later and compared to urine from mice that had not been exposed to UV. (n=3, error bars: +SD, two tail Student's t-test).

Using the in vivo tumor model employed above, bilateral flank human colorectal tumors were implanted and veiled STREAM synthetic biomarkers were injected intravenously. In this approach, the STREAMs are protected from cleavage in blood and other organs, including the tumor, unless selectively unveiled by exposure to light. Thus, by shining light on tumor-bearing flanks, subsequent reporter release should be mediated by the elevated protease concentration in the vicinity of the tumor (FIG. 5C). 1 h after injection, urine was voided to eliminate reporters that had already accumulated by nonspecific protease cleavage. STREAMs were activated by illuminating the tumor site for 30 s per flank, and urine was collected again 30 min after exposure. Unmodified synthetic biomarkers, following this protocol, were unable to distinguish between tumor and healthy animals, due to rapid depletion of the substrate within the first hour and to greater noise generated by blood-borne protease cleavage. This result that unprotected synthetic biomarkers, using this substrate, are unable to distinguish between tumor and healthy mice at late time points is supported by previous work, which characterizes the importance of the time point for urine measurement. This waning sensitivity is due to a diminished signal separation that occurs over time, as this class of substrates is susceptible to cleavage by background proteases. Alternate substrates that are more resistant to background proteases do not suffer from this drawback. Therefore, another benefit of the STREAMs approach is that it provides greater temporal flexibility in when urine samples are collected, as the kinetics of the experiment are externally controlled by initiating activation with light. In contrast to unmodified synthetic biomarkers, a significantly higher signal was present in the urine of tumor-bearing mice after light activation of STREAM synthetic bio-markers when compared to the nonilluminated cohort (2.1-fold). This finding indicates that STREAMs were activated at the tumor by light and cleaved by tumor-associated proteases. The urine signals obtained from the light-activated group were also significantly higher than the STREAM-derived signal observed in healthy animals without light treatment (2.6-fold; FIG. 5C). This signal enhancement is consistent with previous work, but in the case of STREAMs, it is associated with proteases in the tumor bed as opposed to tumor-derived proteases secreted into the bloodstream. In order to test whether UV exposure itself had an impact on the proteolysis of unmodified substrates, urine in mice with and without light exposure was tested and no significant differences of the urine signals collected in each case were observed (FIG. 17). Collectively, STREAM synthetic biomarkers enable the tissue specific detection of protease activity in vivo with simple quantifications in the urine.

One important aspect of the present approach to consider is the choice of light source and the wavelength used for unveiling. A power density of approximately 200 mW/cm$^2$ for a 30 s exposure was used. This dosing is similar to or lower than the power used in other examples of in vivo photoactivation that maintain cellular viability and thus has been cited as demonstrations of the safety of this approach for brief exposures. As photolabile chemistry advances to improve quantum yield of photolysis, these power requirements will diminish. Additionally, the use of UVA light (320-400 nm) versus UVB light (280-320 nm) is of importance as UVA light is a relatively poor tumor-initiating agent and UVA light is used clinically as a therapeutic for skin diseases. Importantly, the present system is compatible with two-photon unveiling, which should benefit potential in vivo applications (FIG. 8). Furthermore, it has been shown that implantable light sources can be used to probe previously inaccessible tumors. For immediate applications, STREAMs have the potential to help guide the development of therapeutics as well as profile the invasive potential of tumors. As one example, there has been a growing interest in developing therapeutic antibodies that are unveiled in the tumor microenvironment due to proteolytic stimuli. By measuring activity in patient-derived xenografts, STREAMs could be used to identify optimal substrates that can mask therapeutics, such that their specific release occurs only at tumor sites. This capacity may instill the STREAM platform with the potential to stratify protease-activated therapeutics based on tumor type and specific protease activity in vivo.

Example 8: Materials and Methods of Examples 1-7

Synthesis of Peptides/Reporters and Nanoparticles (NPs)

Fluorescein-conjugated peptides (MMP sensitive, C1: FAM-sk-PLGLEEA-GC; SEQ ID NO: 3) were synthesized. D-amino acid controls were also synthesized, where the substrate sequence was all D-stereoisomers. Peptides for in vivo studies that contain a ligand-encoded reporter for urinary clearance and subsequent ELISA detection were synthesized (V1: Biotin-PEG(5 kDa)-(KFAM)-PLGLEEA-GC; SEQ ID NO: 4). The PEG 5 kDa reporter is efficiently cleared by the renal system into the urine and can be quantified by ELISA for the conjugated ligands. The alternate substrate to show STREAMs extensibility was synthesized at a different location (sequence: eGvndneeGff-sarKsRLVGEGC; SEQ ID NO: 5). VT750 (PerkinElmer) was conjugated to the free lysine prior to coupling to DMNPE. DMNPE can indeed react with numerous glutamic acids throughout the tandem peptide, necessitating a high DMNPE:peptide excess of 100:1.

NPs were formed by reacting iron(III) chloride hexahydrate and iron(II) chloride tetrahydrate with dextran as previously described. NPs were aminated by reacting with ammonium hydroxide. Size measurements were performed by dynamic light scattering (Malvern Instruments Nano ZS90) revealed a mean diameter less than 100 nm. NPs were reacted with a 500-fold molar excess of N-succinimidyl iodoacetate (SIA) (Pierce) for 1 h at room temperature in 50 mM sodium borate, pH 8.3, 5 mM EDTA to provide thiol reactive handles. Excess SIA was removed either by fast-protein liquid chromatography (FPLC, GE Healthcare) or by spin-filters (MWCO=30 kDa, Millipore). SIA-NPs were reacted with peptide substrate-reporter complexes at a 1:95 ratio in the borate buffer overnight at room temperature. For the in vivo particles, mPEG thiol (20 kDa, Laysan) was also reacted with at a 20 molar excess ratio to NPs to provide stability and prevent phagocytic uptake. After purification and buffer exchange into PBS, peptide-reporter valency was quantified by absorbance. For strong quenching, valency>20 was needed. NP-peptide-reporter complexes were stored at 4° C.

Conjugation of DMNPE to Peptides and Peptide-NPs

Peptides were coupled to DMNPE either before or after conjugation to nanoparticles (NPs). DMNPE was generated using the DMNPE generation kit (Life Technologies) according to manufacturer protocols. DMNPE was then allowed to react with peptides in a 50:50 DMSO to PBS ratio overnight on a shaker with excess DMNPE. After the reaction was completed, excess DMNPE was removed either by high-pressure liquid chromatography (HPLC) or by FPLC/spin filters (if peptide was already coupled to NPs). Confirmation of modification was either verified by absorbance changes (DMNPE has a max absorbance around 350 nm) or by mass spectrometry.

Mass Spectrometry Analysis of Peptide-DMNPE

After purification by HPLC, peptide-DMNPE was analyzed by mass spectrometry by ESI-MS. DMNPE (MW=209.66 Da) presence was confirmed by a mass shift from the peptide mass. Typical MALDI analysis cannot be used to detect DMNPE, as the MALDI laser operates at the same wavelength as DMNPE max absorbance. Therefore, to demonstrate that DMNPE can be removed by light treatment, the MALDI analysis was performed on the same peptide-DMNPE complex showing a mass shift back to the original peptide mass.

In Vitro Recombinant Protease Assays

C1-NP complexes sensitive to MMP cleavage were mixed with 1% (wt/vol) BSA (Sigma) and incubated with recombinant proteases (MMPs and ADAMs: Enzo Life Sciences; Clotting proteases: Haematologic Technologies) in a final volume of 100 μL in enzyme-specific buffers (MMP buffer: 50 mM Tris, 150 mM NaCl, 5 mM CaCl2, 1 μM ZnCl2, pH 7.5; Clotting proteases: PBS) in a 384-well plate for time-lapse fluorimetry to measure dequenching from homo-quenched peptides at 37° C. (SpectroMax Gemini EM Microplate Reader). For the metalloproteinase, enzymes were diluted 1:10 in enzyme specific buffer, and for clotting proteases, enzymes were diluted 1:100. Cleavage heatmap was generated using GENE-E (Broad Institute). Michaelis-Menten constants were determined by assessing initial cleavage velocities at different substrate concentrations. The MMP inhibitor Marimatstat (Tocris) was added to the mixture at 100 μM final concentration. To identify the cleavage position by MMP9, C1-NPs were incubated with MMP9 overnight, and the N-terminal cleavage fragment was isolated and analyzed by MALDI. The sequence corresponding to the dominant peak was identified, and the final amino acid was in that sequence represents the P1 position (toward the N-terminal end from scissile bond). For protease resistance assays, various DMNPE: peptide ratios were reacted overnight and purified prior to being added to proteases.

Light Activation of Peptides

Light activation of peptides for biochemical studies was performed using a CL-1000 UV Cross-linker (UVP, 8 mW/cm$^2$). Power density was measured by an OAI 306 UV power meter at 365 nm. Typical exposure time for these studies was 10-30 min. For activation in cell and animal studies, Lumen Dynamics UV system with 365 nm fiber light guide was used (OmniCure 1000, 200 mW/cm$^2$). For in vivo activation at the tumor site, mice were anesthetized, and the light was guided through an optical cable and placed approximately 3 cm from the flank tumor. Each flank tumor was exposed for 30 s.

Two-photon unveiling was performed at the KI Microscopy Core with a multiphoton microscope (Olympus FV-1000MP) operating at 690 nm with a Spectra-Physics Deepsea Tia-sapphire laser at power 1 W using a 25× objective with 1.05 NA. Samples were placed in glass bottom 384-well plates. Images were captured at 840 nm.

Cell Culture and Secreted Protease Activity Assay

LS174T and CCD-18Co (ATCC CRL-1459) cells were cultured in Eagle's Minimal Essential Medium (ATCC) supplemented with 10% FBS (Gibco) and 1% penicillin-streptomycin (CellGro). Cells were passaged when confluence reached 80%. To isolate secreted proteases, after cells were plated, cells were washed and replaced in serum-free media. Conditioned media was collected 24 h later and exposed to C1-NPs to measure fluorescence dequenching.

3D Tissue Engineering Models

LS174T cells were encapsulated in 2.5 mg/mL collagen hydrogels (rat tail collagen type I, Corning). Imaging was done on Nikon Eclipse Ti Inverted Microscopes and Zeiss Stereoscope Discovery v20. When protease activity was measured, surrounding media was serum-free.

Agarose Gel Assay

Agarose (type I-A, Sigma) was dissolved in MMP9 specific buffer (1% w/v) and heated. As the gel mixture was cooling, gel solution was transferred into a 96-well plate and mixed with STREAMs and recombinant MMP9. After gelation, the gels were activated (as above), and fluorescence dequenching through cleavage was monitored using time-lapse fluorimetry.

In Vivo Wild-Type Animal Studies

The in vivo STREAM synthetic biomarkers (V1-NPs) were diluted to 1 µM in sterile PBS. Wild-type, female Swiss Webster mice (4-6 wk, Taconic) were infused intravenously via the tail vein. Immediately after infusion, mice were placed in an in-house devised urine collector with a 96-well plate base. To quantify level of protection, unmodified synthetic biomarkers were also injected. Additionally, for a third group, STREAMs were activated prior to injection. Thirty min post-injection, urine was collected and stored at −80° C.

For analysis, urine was diluted from 100× to 10,000× in PBS BSA (1%). Reporter concentration was quantified by a custom designed and characterized ELISA as described previously.[22,23] Briefly, R-FITC antibodies (GeneTex) were used as the capture antibody at the bottom of a high-binding 96-well plate. NeutrAvidin-HRP (Pierce) was used as the detection antibody to recognize the N-terminal biotin on the reporter. Bound HRP was exposed to Ultra-TMB (Pierce) substrate, and the reaction was allowed to progress. The reaction was quenched when the ladder could be visualized using 1 M HCl. Absorbance was measured at 450 nm using a plate reader (Molecular Devices SpectraMax Plus).

Flank Tumor Model of Colorectal Cancer

Female NCr Nude mice (4-6 week, Taconic) were inoculated subcutaneously with 3×10$^6$ LS174T cells per flank and allowed to grow. Two weeks after inoculation, the mice were infused with the STREAMs. Tumor-bearing mice and age-matched controls were infused with STREAM synthetic biomarkers and placed in urine collectors. After 1 h, the mice were voided of urine. A fraction of these animals were exposed to light over the flank tumors as described. All animals were infused with 0.5 mL of PBS subcutaneously to increase urine production at 1 h. The animals were placed back into urine collectors. Urine from all animals was collected 30 min later and analyzed as described above. Unmodified synthetic biomarkers were also infused in a different cohort of mice, and a similar set of operations was performed.

Example 9: Magnetically Actuated Protease Sensors for In Vivo Tumor Profiling

With the advent of molecular targeted therapies, there has been significant effort towards precision medicine to match the right therapy to the right patient with high confidence for increased efficacy. To help clinicians make informed decisions about treatment, robust companion molecular diagnostics are needed to stratify individual patients to identify appropriate therapies. Current companion diagnostics include molecular imaging strategies to stratify patients, such as identifying vascular permeability to nanotherapeutics. Alternatively, analysis of samples acquired by invasive biopsies is used to identify therapeutic targets (e.g. Her2 overexpression for prescription of Herceptin). Finally, liquid biopsies have gained momentum (e.g. for circulating tumor cells or cell-free nucleic acids) as a sample source to stratify patients and identify therapies. An emerging area of targeted therapies is protease-activated therapeutics, which have the promise to improve therapeutic windows of numerous agents and represent an exciting class of proteins to target as they play a role in almost every hallmark of cancer. Protease-activated antibodies, 'probodies', being commercialized by CytoMx are one such example. Functional diagnostics that provide information on the activity and function of proteases within the tumor will further increase the utility of these therapies.

Protease activity is typically measured using functionalized synthetic peptide sequences that generate image contrast after cleavage. Proteases, however, are promiscuous in their cleavage specificities for short synthetic peptides resulting in high-background and off-target activation.

The development of magnetically actuated protease sensors (MAPS) that rely on alternating magnetic fields (AMF) to release peptide substrates from thermosensitive liposomes into the tumor microenvironment to sample protease activity is described. To accomplish this, peptide substrates are co-encapsulated with magnetic nanoparticles (MNPs), which can locally raise the temperature due to hysteretic heat dissipation. The temperature sensitivities of MAPS and responsiveness to AMF in vitro was characterized and the newly formulated sensor was applied to profile protease cleavage specificities across two xenograft mouse models of colorectal cancer by local, remote activation at the tumor site.

Example 10: Development and Characterization of Magnetically Actuated Protease Sensors (MAPS)

Matrix metalloproteinases (MMPs) are a family of structurally related, zinc-dependent endopeptidases with important roles in development, tissue injury and repair, and many diseases. In cancer, MMPs promote invasion and metastasis and different tumors often have unique MMP expression profiles. Determination of tumor MMP activity profiles of individual patients would enable the development of targeted therapeutics in a personalized manner. Thus, a remotely controllable nanosensor was designed to locally assay MMP profiles in tumors by encapsulating protease-sensitive substrates into thermosensitive liposomes capable of remotely triggered release after excitation with AMF.

Figure 18A:
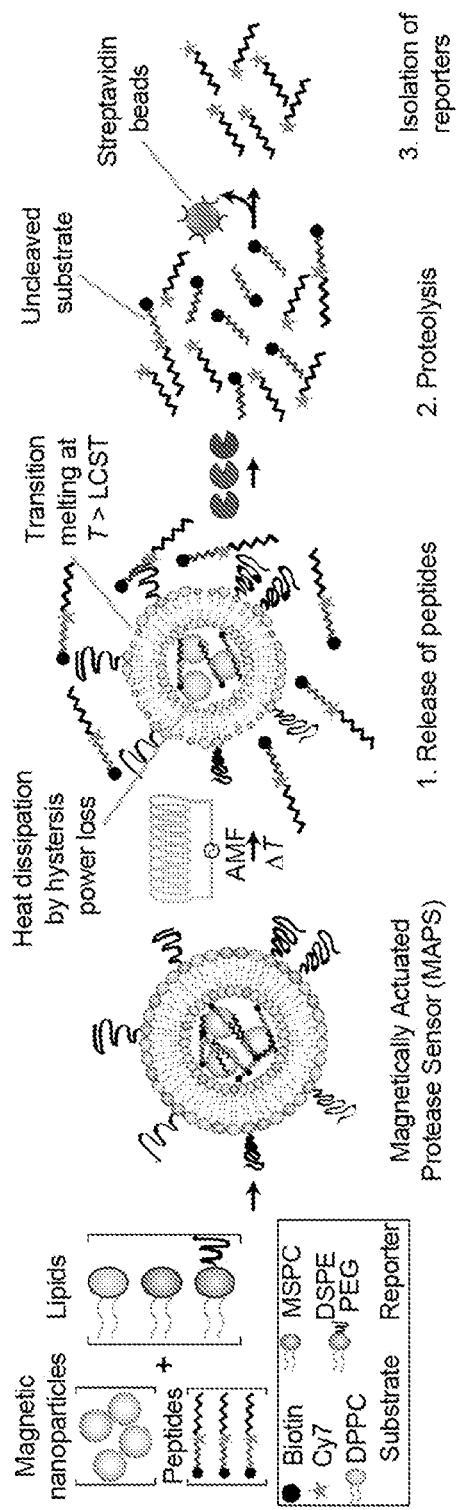
FIGS. 18A-18C show magnetically actuated protease sensors (MAPS).

The capability of liposomal carrier to entrap a variety of materials and their ability to accumulate at tumor sites via the enhanced permeability and retention (EPR) effect was utilized to shield the peptide-substrates from nonspecific cleavage in the blood stream. The sensor consisted of a liposomal, thermosensitive shell loaded with a selection of protease-cleavable substrates in tandem with urinary reporters and co-entrapped magnetic NPs enabling electromagnetically induced heat triggers (FIG. 18A). These magnetically activatable protease sensors (MAPS) are triggered to release the peptide substrates by applying alternating magnetic fields (AMF) in the range of hundreds of kHz. Heat is dissipated through hysteretic losses of the co-entrapped magnetic nanomaterial, which results in permeabilization of the thermosensitive liposomal bilayer (FIG. 18).

A clinically approved thermosensitive liposome formulation containing DCCP, the most commonly phosphoglyceride used as backbone for liposomal bilayer preparation, was chosen as the lysolipid (MSPC) and DSPE-PEG(2000). This thermosensitive construct has been widely studied due to a rapid increase of membrane permeability for fast release, which results in a sharp thermal transition at ideally moderate temperatures, while preserving stability and sufficiently long circulation time in blood at body temperature. At the phase transition temperature, liposomal bilayers exhibit leaky interfacial regions between still solid and melting liquid phases. The resulting permeability can be significantly enhanced through the addition of the lysolipid MSPC, which is assumed to stabilize the pores yielding higher and faster release rates. For the chosen volume ratio of 80:15:5 for DCCP:MSPC:DSPE-PEG, the critical melting temperature was determined as $T_m \approx 41°$ C.,[72, 74] and thus, required only mild temperature elevation through externally triggered magnetic heat dissipation.

Figures 20A, 20B:
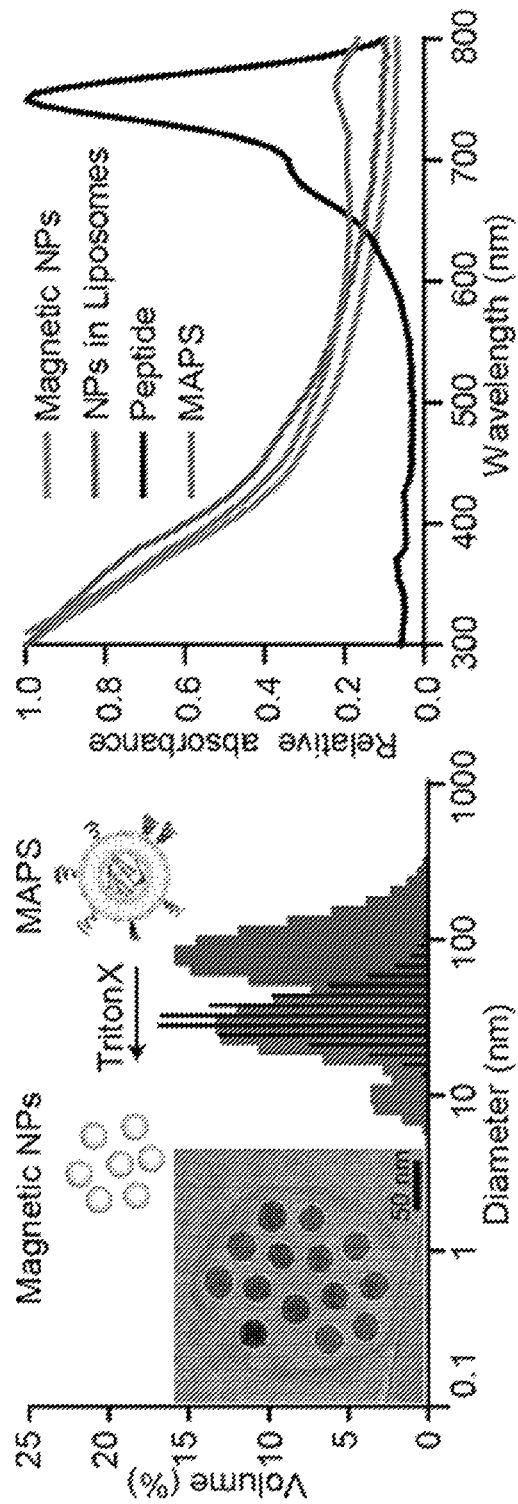
FIGS. 20A-20D present MAPS characterization: size, composition, magnetic properties and stability.
Figure 22:
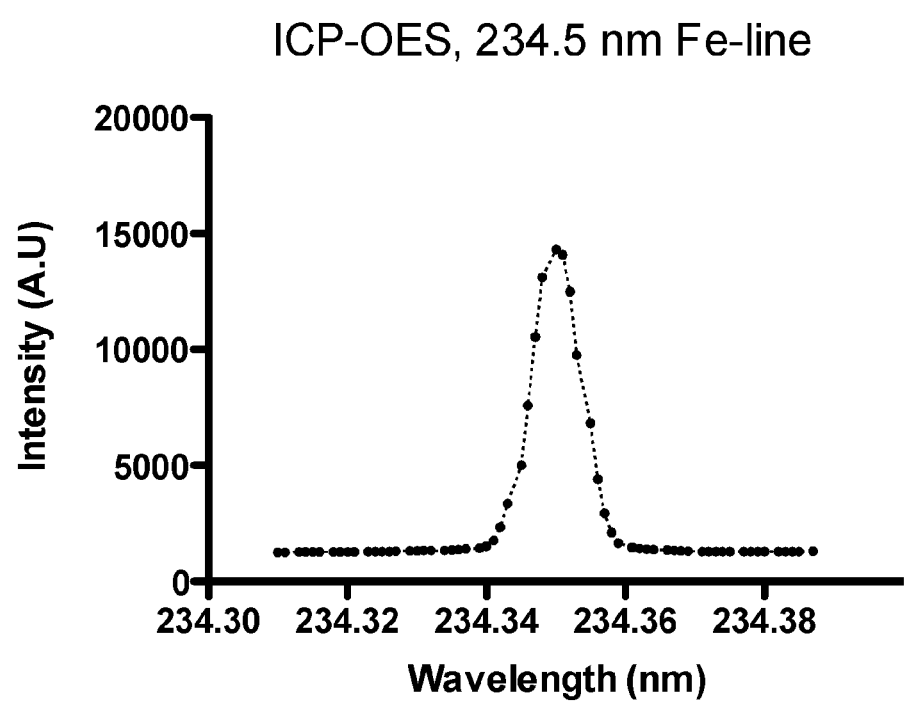
FIG. 22 shows the quantification of iron content through ICP-OES measurements.

To reach the required temperature elevation, iron oxide nanoparticles with a diameter of 25 nm (Ocean Nanotech LLC, SHA-25, FIG. 20A) were selected. The final sensor containing MNPs and peptides yield a narrow size distribution of 130 nm (FIG. 20A) and the amount of the individual loaded components of MAPS suspensions after filtration was measured by absorbance spectroscopy (FIG. 20B). Sufficient loading of MAPS with MNPs is crucial to ensure magnetothermal activation and the iron content was determined by inductively coupled plasma optical emission spectrometry (ICP-OES) yielding 1.89±0.15 mg/ml (FIG. 22).

Example 11: Stability and Magnetically Triggered Release Profile of MAPS

Prior to applying MAPS to profile MMP activity, the thermosensitivity and temperature-related release profile was characterized. A calcein-based assay utilizing the homoquenching at high concentrations of this membrane impermeable dye was used, which allowed release quantification, by measuring the increase of the fluorescence signal.

Figure 20C:
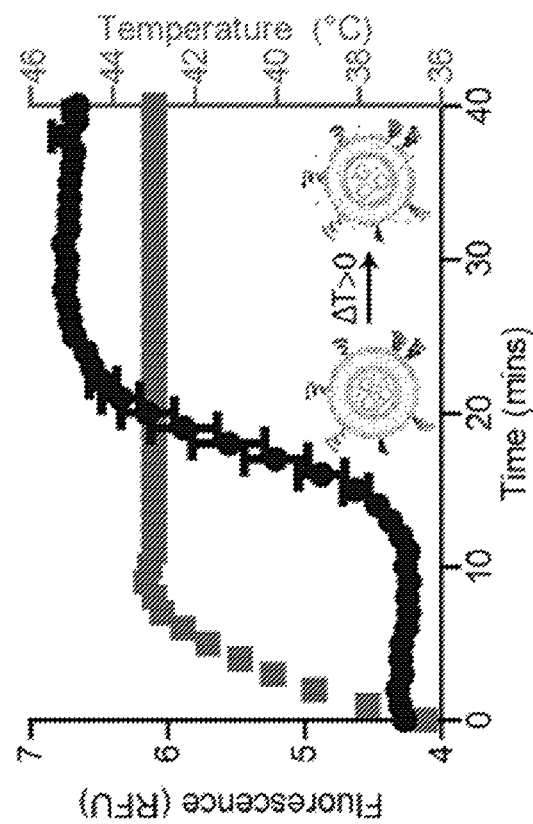
Figure 20D:
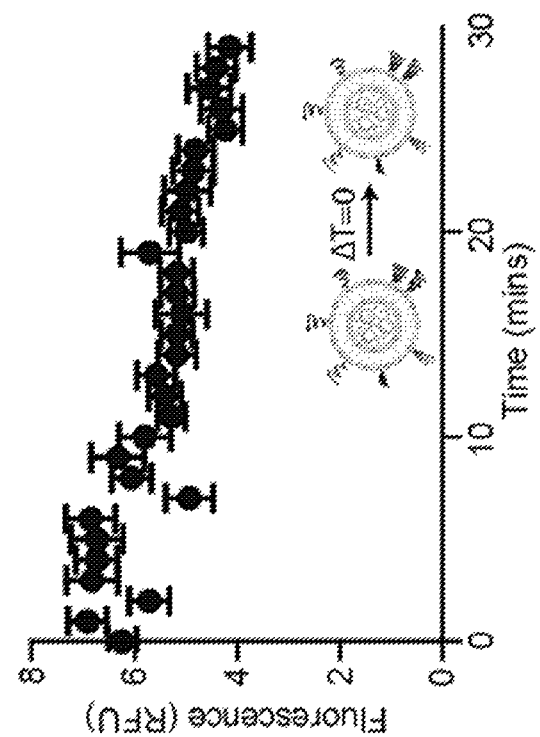

The permeation over time at 37° C. was first probed and the liposomes were found to be stable, as no increase of the fluorescence signal was detected (FIG. 20C). The temperature was increased to 43° C. to assess the dynamic response of the thermosensitive liposomes and dramatic increases in sample fluorescence at higher temperatures were noted (FIG. 20D).

Example 12: Magnetothermal Activation

Next, the driving magnetic field parameters to achieve sufficient heating rates through magnetothermal activation were determined. A high specific loss power (SLP) of the co-encapsulated MNPs is needed such that there is sufficiently high heat dissipation at the liposomal bilayer to achieve melting of the membrane. To achieve a high SLP and, thus, high heating rates, several parameters come into play such as the strength of the externally applied magnetic field and its frequency, and intrinsic factors such as the nanoparticle size, shape anisotropy and composition.[75] The SLP is determined as SLP=c/m $\Delta T/\Delta t$, where C is approximately the specific heat capacity of water (C=4.184 J K−1 ml−1), m is the concentration of the ferrofluid (in g Fe/mL) and $\Delta T/\Delta t$ is the experimentally measured initial slope of the temperature increase over time under AMF exposure.

While earlier reported magnetic liposomes are commonly loaded with small iron oxide nanoparticles in the size range of 5-15 nm21, comparatively larger 25 nm MNPs were chosen due to their high specific loss power (SLP) at low frequencies. This is explained due to the significant contribution of Stoner-Wohlfahrt-like hysteresis losses to the heating rate at increasing particle sizes, while smaller particles exhibit solely Néel and Brownian relaxation as energy loss mechanisms. Given particles of differing size and same SLP, larger particles dissipate more heat due to their greater volume, which becomes evident when comparing the intrinsic particle loss power per particle (IPLP)—normalized with respect to the externally applied field magnitude and frequency (Table 1). In addition, with the reported steep temperature increase at the surface of the nanoparticles, in some embodiments, a smaller number of somewhat larger MNPs in close contact with the liposomal bilayer efficiently triggers release.

TABLE 1

Estimations of individual particle loss power (IPLP) for increasing particle size

| Particle Size | SLP (W/g) | Estimated IPLP (fW) |
|---|---|---|
| 10 nm | 75 ± 5 | 0.15 |
| 15 nm | 302 ± 16 | 2.0 |
| 20 nm | 569 ± 17 | 8.4 |
| 25 nm | 610 ± 16 | 19.0 |

Figure 21B:
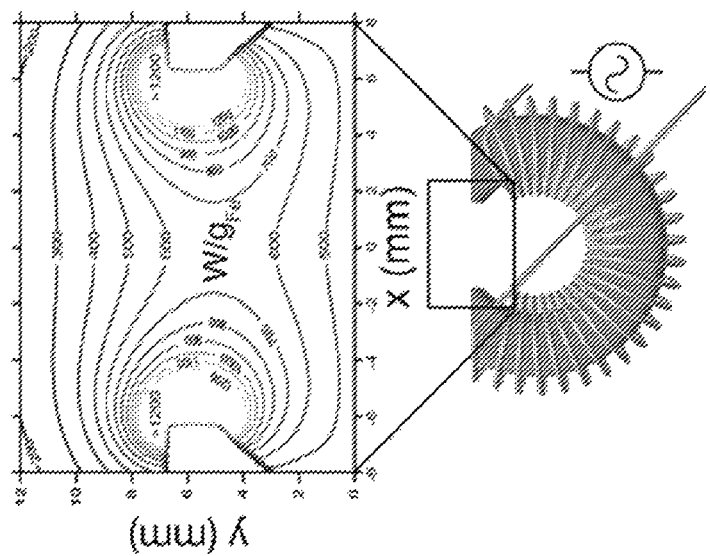
FIGS. 21A-21D show magnetothermal activation: coil design and parameter determination for magnetically-induced release.
Figure 21A:
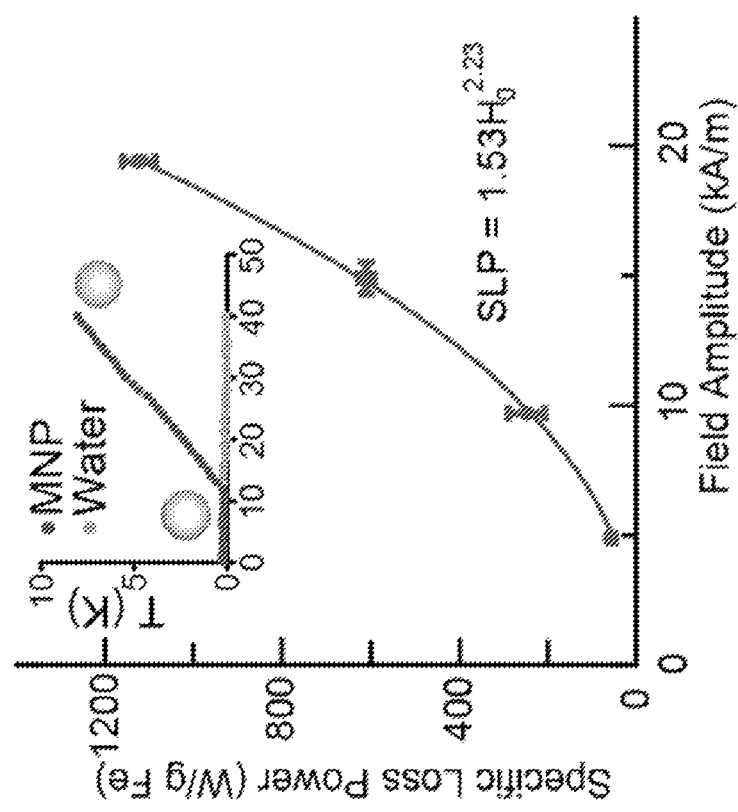
Figure 23:
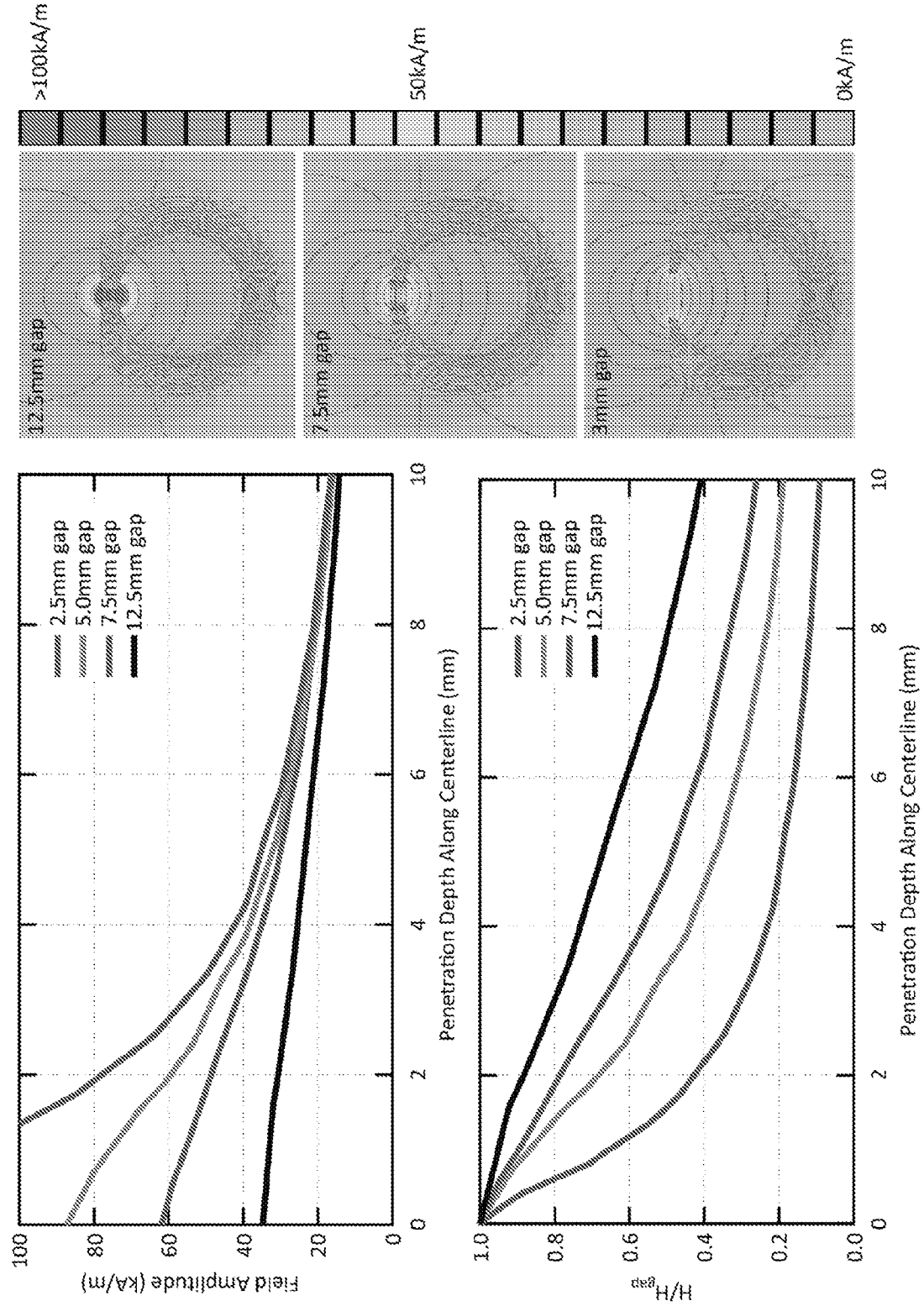
FIG. 23 shows modeling of magnetic field strength along the centerline for varying gap size.
Figure 24:
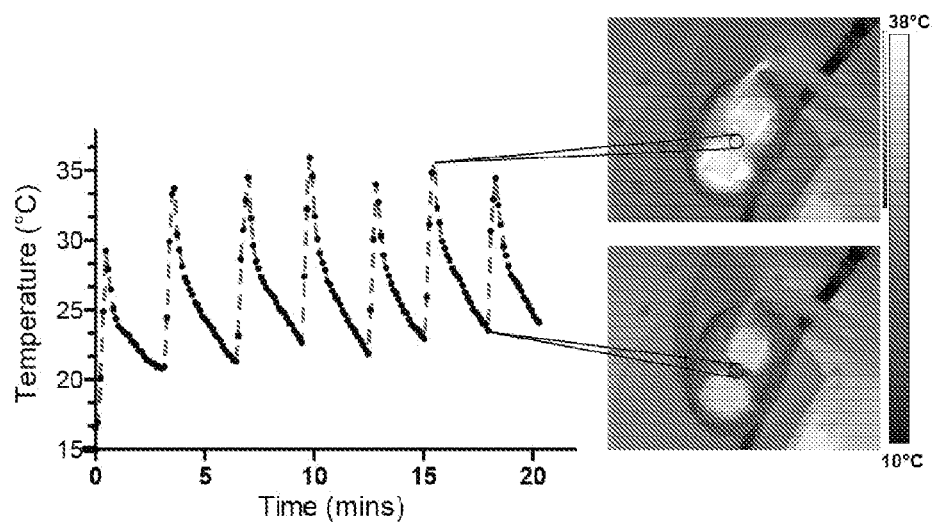
FIG. 24 shows thermal imaging of heat dissipation of a coil during duty cycles using an infrared camera. The temperature values plotted are derived from the averaged temperature across the area of a circle of 10 mm diameter located in the center of the gap, i.e. the location of the flank tumor during operation.

For the selected MNPs, the SLP at 515 kHz and 15 kA/m was determined as 610±16 W/g(Fe) using a fiber optic sensor for temperature monitoring of the ferrofluid (FIG. 21A, and inset). A coil setup with a gap size of 12.5 mm to accommodate up to approximately 1 cm³ large tumors while operating at the same conditions (FIG. 21B, FIG. 23) without significant overheating (FIG. 21C, FIG. 24) was designed. A duty cycle at heating intervals of 40 sec with a 240 sec break yielding in steady state operation conditions was determined. The SLP was also modeled across the operating area to ensure sufficient heating rates across the tumor (FIG. 21B).

Figures 21C, 21D:
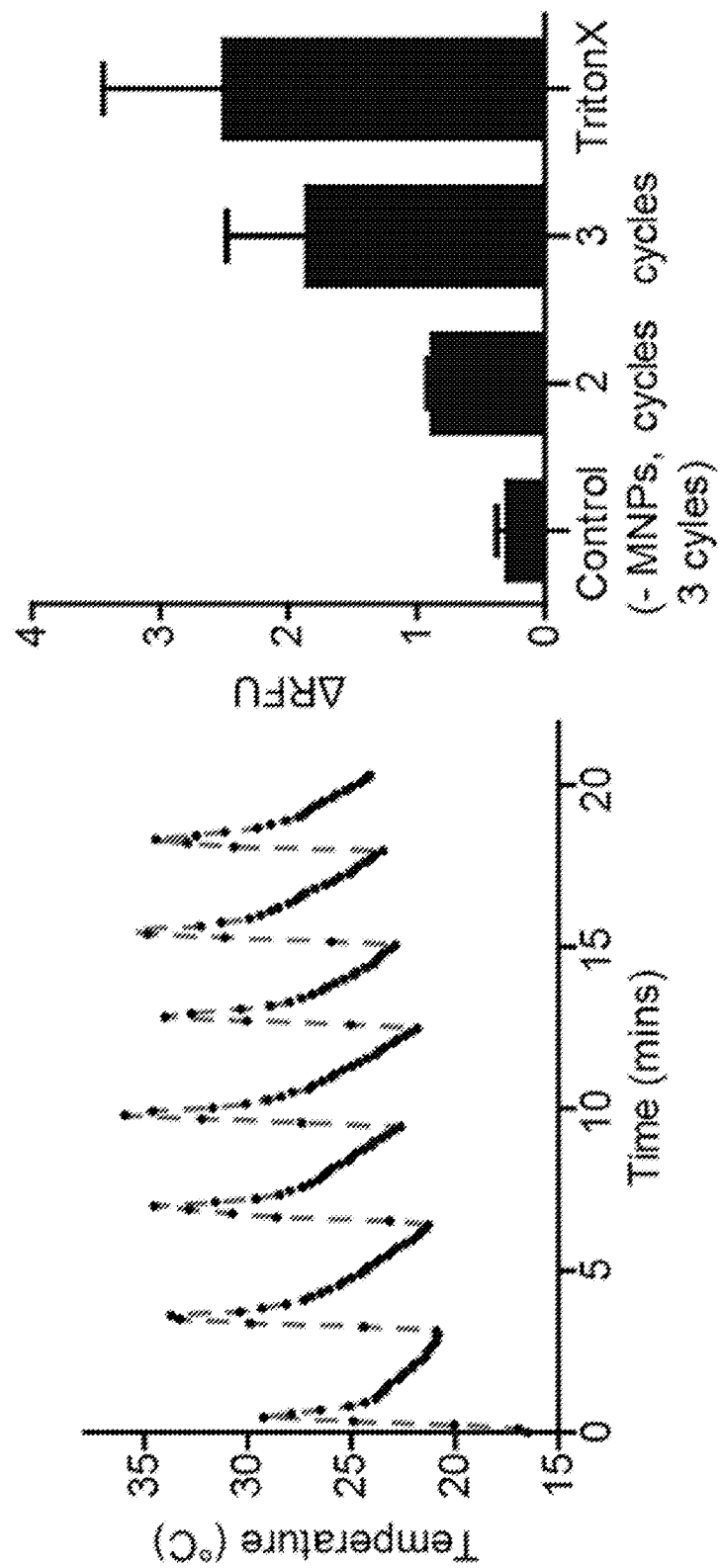

Next, the release profile was probed by remotely induced in situ heat dissipation using AMF. Samples were exposed with and without MNPs to AMF activation sequences of 40 s. The relative fluorescence signal did not significantly increase for the control sample, which did not contain coencapsulated MNPs (FIG. 21D). The fluid temperature was monitored with a fiber optic sensor ensuring that heat contributions from the setup did not exceed 38° C. Increasing the cycle number was found to cause a corresponding increase in release when MNPs were coencapsulated (FIG. 21D). This dose response relationship between AMF exposure and content release indicated that graded control for use in dynamic and repeated measurements was applicable. Liposome disruption was achieved using Triton X-100 and resulted in fluorescence increase on par with magnetic release (FIG. 21D).

Figure 18B:
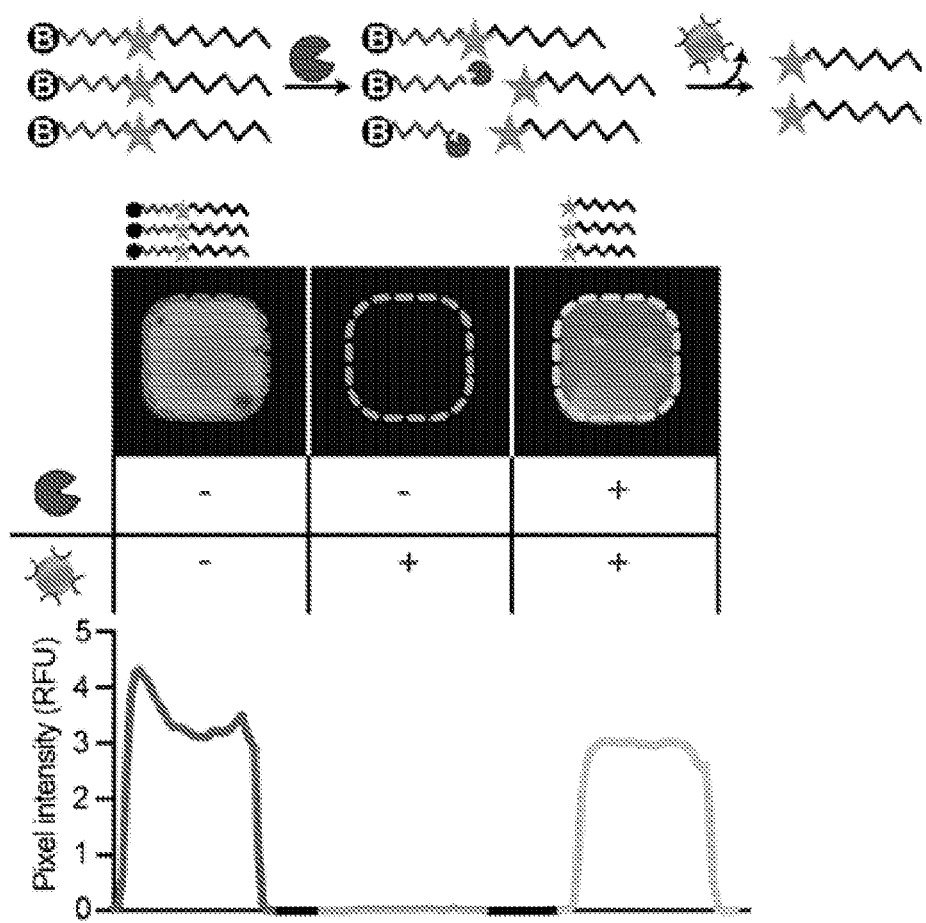
Figure 18C:
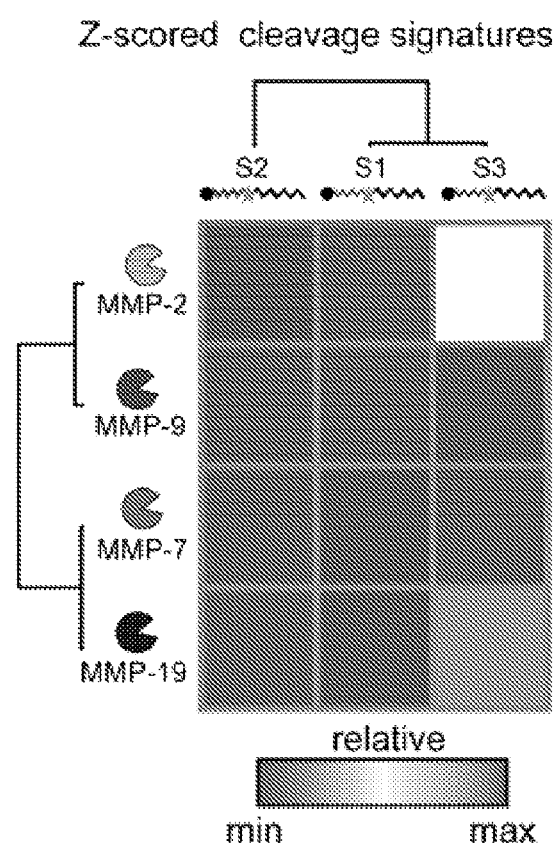
Figure 25A:
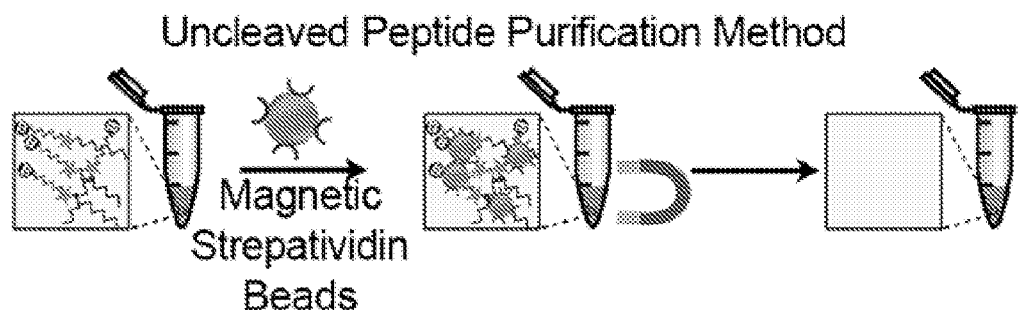
FIGS. 25A-25C show urine depletion of uncleaved substances.
Figures 25B, 25C:
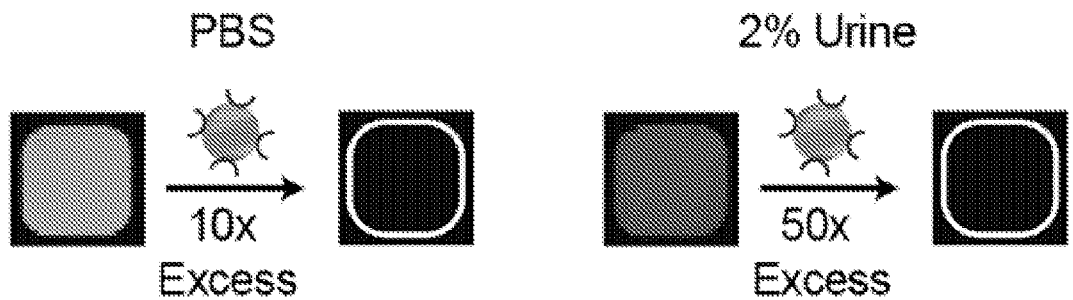
Figure 26A:
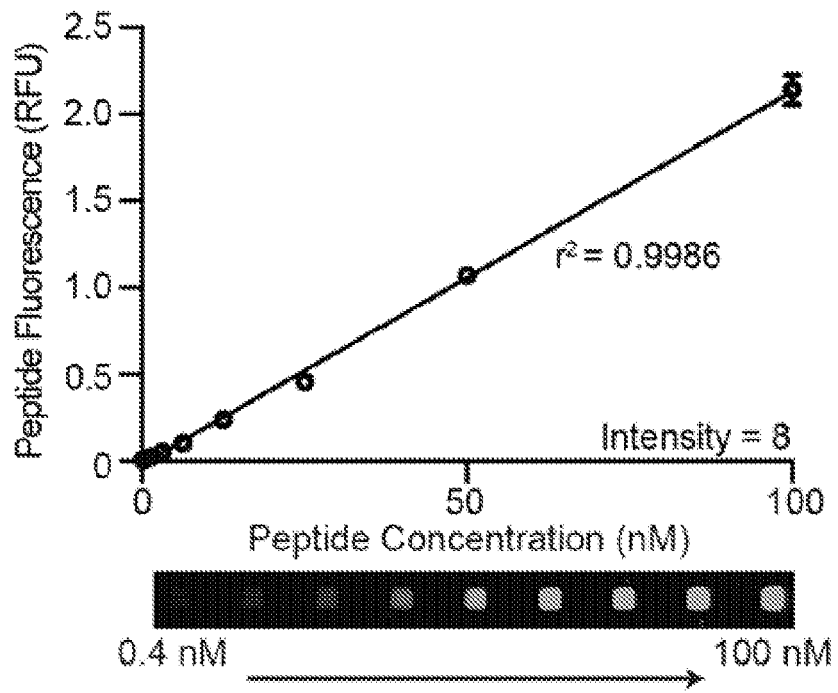
FIGS. 26A-26B show Cy7 ladder reading on an IR scanner. The scanner is sensitive to large dynamic range of peptide concentrations at different intensity gains enabling both high (FIG. 26A) and low (FIG. 26B) peptide concentration quantification.
Figure 26B:
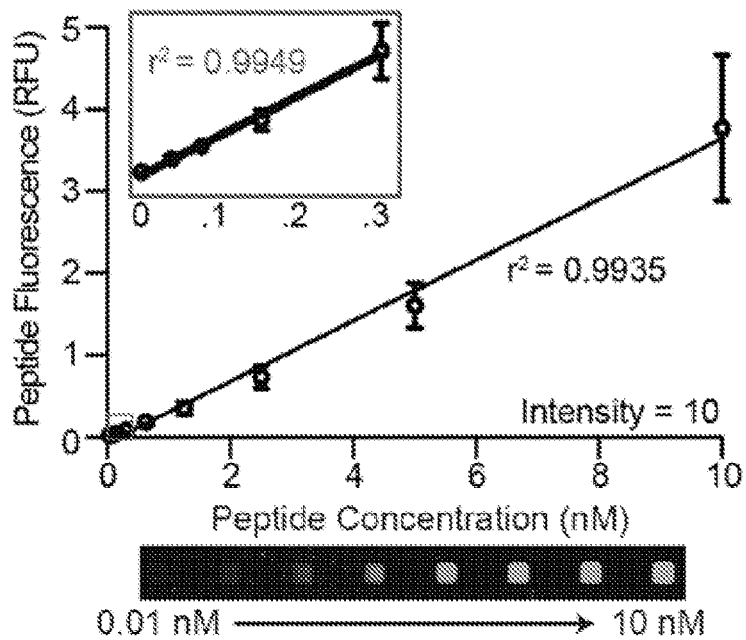

Example 13: Characterization of Peptide Substrates and Associated Protease Cleavage Signatures Based on previous work on synthetic urinary biomarkers, three peptide substrates that respond to MMPs were chosen. These protease substrates are each in tandem with a D-stereoisomer of glutamate fibrinopeptide coupled with a near IR dye as a urinary reporter, similar to previous synthetic biomarker developments (FIG. 18B, Table 2). In the previous work; however, synthetic biomarkers were constructed of peptide-reporter tandem conjugates coupled to iron oxide nanoparticle backbones. Upon intravenous injection, these biomarkers passively accumulated at sites of disease and proteolysis of the peptide substrate freed the reporter, which was then be detected in the urine. In contrast to previous approaches, the peptides used in this study were not tethered directly to a nanoparticle scaffold. Therefore, the peptide construct could potentially enter the urine without proteolysis, thereby confounding the urine signal. To circumvent this, an N-terminal biotin was tethered to all peptides, which could be depleted in the urine such as to only measure cleaved reporters (FIG. 25A). This new detection method was validated by first confirming the capability to completely remove uncleaved excess substrate by measuring the fluorescence signal of free peptide sequences in PBS and 2% urine pre- and post-magnetic separation (FIGS. 25B, 25C). Cy7 measurements were robust and could be measured over several log dilutions using an IR fluorescence scanner (FIG. 26). Moreover, the shielding mechanism of the liposomal bilayer was confirmed by incubating MAPS with streptavidin beads and exposure to a permanent magnet (FIG. 27). Using this new detection method, relative proteolysis of the substrates by several MMPs was measured (FIGS. 18B, 18C). By hierarchical clustering, S1 and S3 performed similarly and responded primarily to MMP2 and MMP9. S2 was cleaved efficiently by MMP7 and MMP19 (FIG. 18C). Using three distinct substrates was thought to enable more specific profiling of tumor protease activity in vivo.

TABLE 2

Sequences of peptides employed in study

| Peptide Name | Sequence |
| --- | --- |
| S1 | Biotin-CG<u>PVGLIG</u>*K(Cy7)*<u>eGvndneeGffsar-NH<sub>2</sub></u> (SEQ ID NO: 6) |
| S2 | Biotin-CG<u>PVPLSLVM</u>*K(Cy7)*<u>eGvndneeGffsar-NH<sub>2</sub></u> (SEQ ID NO: 7) |
| S3 | Biotin-CG<u>PLGVRGK</u>*K(Cy7)*<u>eGvndneeGffsar-NH<sub>2</sub></u> (SEQ ID NO: 8) |

Legend:
molecular spacers,
*fluorophore,*
<u>protease substrate,</u>
urinary reporter
Note:
biotin is for isolation of uncleaved substrates;
lowercase letters indicate D-steroisomers

Example 14: Blood Circulation Kinetics and Biodistribution of MAPS

Figures 28A, 28B:
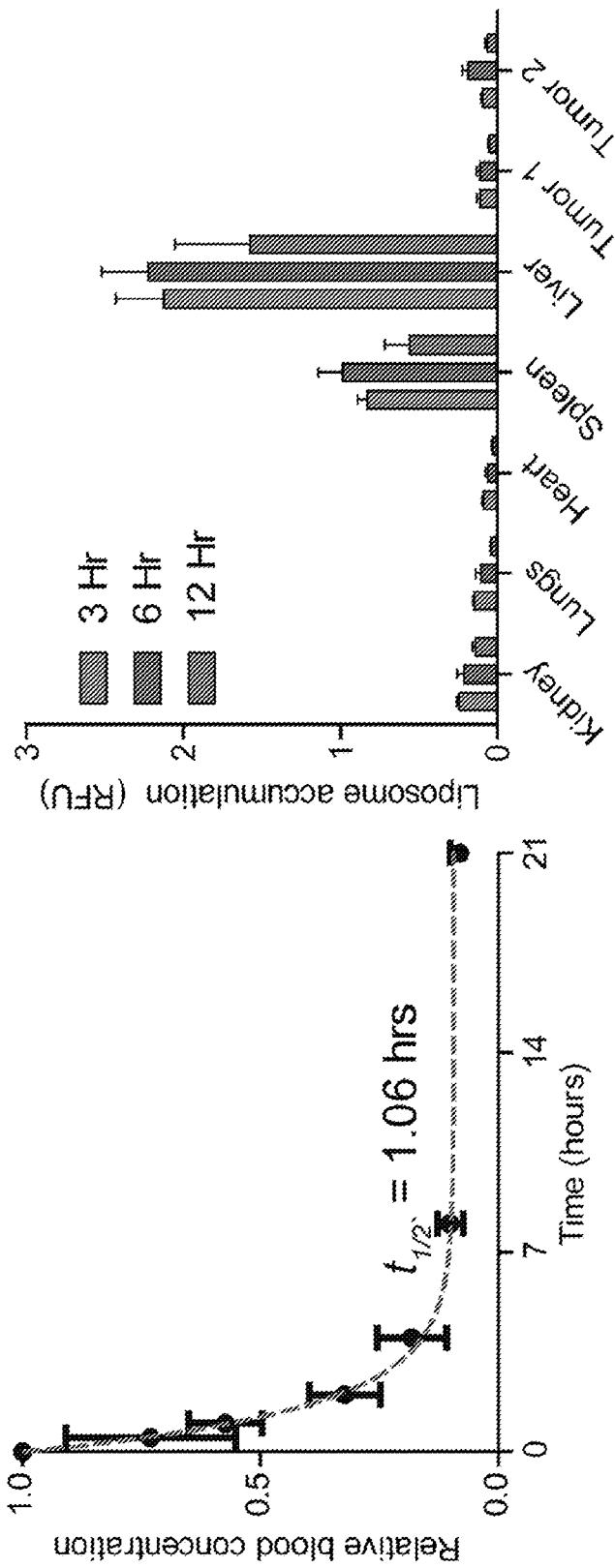
FIGS. 28A-28B show the pharmacokinetic characterization of MAPS.

The performance of MAPS in vivo was next assayed. The blood half-life of fluorescently labeled liposomes in healthy mice was determined to be approximately 1 hour and it was hypothesized that this ensures sufficiently long circulation time to allow for passive accumulation at the tumor (FIG. 28A). Next, organ and tumor accumulation in nude mice over time was measured to identify the optimal timepoint for remote triggering with AMF (FIG. 28B). Significant accumulation in the liver was measured, as was expected for nanomaterials. The high liver accumulation highlights the importance of site-specific triggering. Importantly, the kidneys did not have very high fluorescence, which would be indicative of leakage of cargo from the liposomes. Tumor accumulation was also observed and was relatively constant for several hours. The optimal time for tumor activation of the MAPS was determined to be 3 hours post-administration, as there should be relatively low blood concentration and reasonable tumor accumulation for specific activation.

Figure 19A:
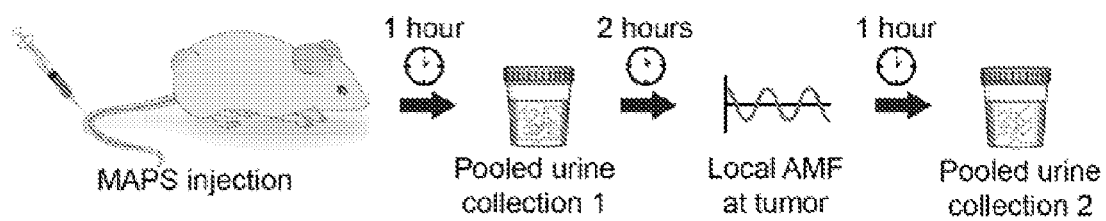
FIGS. 19A-19E show MAPS enable in vivo profiling of protease activity in tumors.
Figures 19B, 19C:
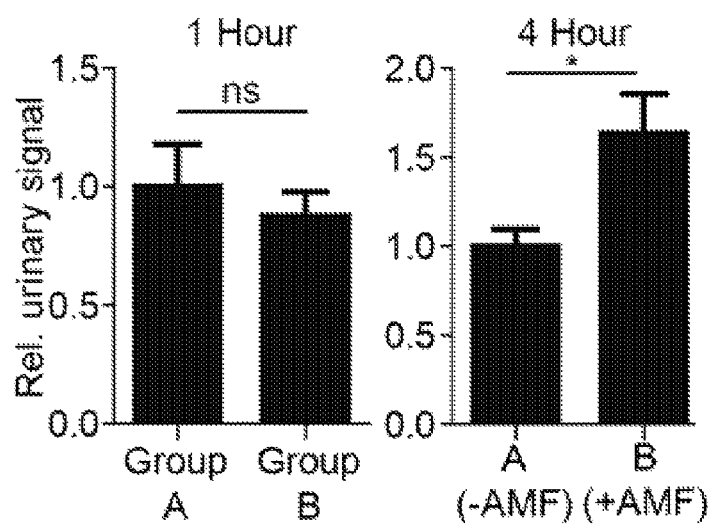
Figure 29:
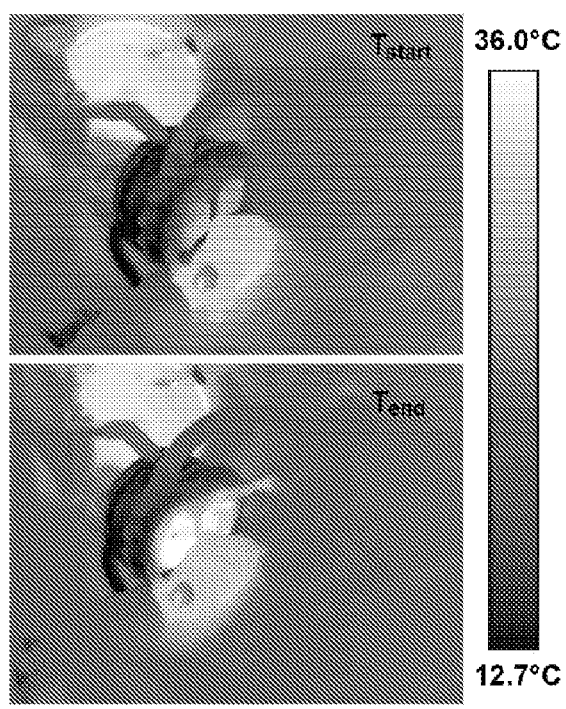
FIG. 29 shows thermal imaging of coil during an in vivo trial. $T_{start}$ and $T_{end}$ denote the time at the beginning and end of a duty cycle, respectively. No tumor specific heating due to local heat dissipation of the coil was observed, and the temperature of the mouse appears homogenous across the body.

Example 15: MAPS Allow Remote, Non-Invasive Activation of Synthetic Biomarkers Next, MAPS were applied to profile tumor protease activity in vivo using the synthetic biomarker system developed. Local activation of MAPS by AMF was first confirmed to be feasible. Flank tumors were implanted using the colorectal cancer cell line LS174T, which has been used extensively for in vivo cancer models and secretes active MMPs, including MMP2, 9. MAPS-S3 were intravenously injected in two cohorts of mice. One hour post-administration, urine from both cohorts was collected; two hours later, one group was exposed to AMF by fitting the flank tumor within a 12.5 mm large gap of a custom-made ring coil at the and urine collected again one hour later (FIG. 19A and FIG. 29). At the one-hour timepoint, as expected, there was no statistically significant difference in the urine signal between the two groups (FIG. 19B). The urine signal measured is likely a result of non-specific leakage in circulation from the liposomes and subsequent proteolytic cleavage. By applying the earlier described 2-cycled AMF signal at the tumor site, it was confirmed that peptide sequences are released and become available to proteolytic cleavage, when urine was collected 1 hour post-activation (4 hours post-injection), for both groups and a statistically significant increase in urine signal derived for the activated group was determined (FIG. 19C).

Example 16: MAPS Distinguish MMP Profiles of Tumor Variants In Vivo

Figures 30A, 30B, 30C:
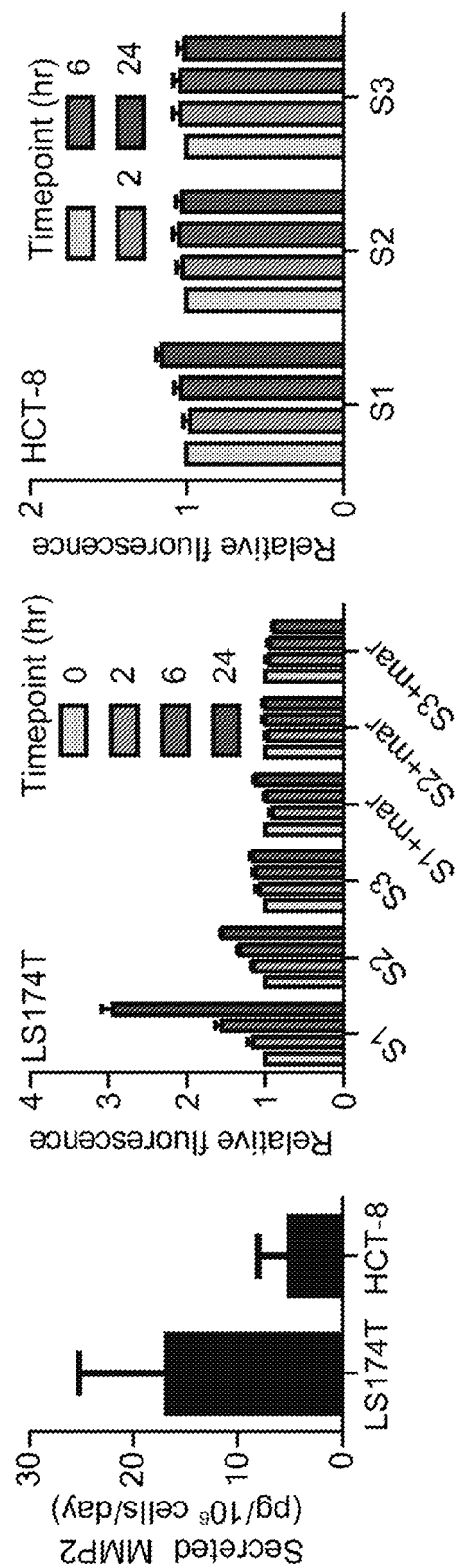
FIGS. 30A-30C show in vitro cellular protease analysis.

Next, whether the MAPS(S1-S3) could distinguish MMP profiles of different tumor types was probed. Another human colon carcinoma line, HCT-8, was selected because it previously showed lower MMP9 secretion compared to LS174T. Additionally, HCT-8 had lower MMP2 secretion compared to LS174T by ELISA for the protein in cell culture supernatant (FIG. 30A). Cleavage of the substrates was tested by cell-secreted proteases by employing fluorescently quenched versions and exposing them to conditioned supernatant. From these in vitro cleavage assays, S1 was cleaved most significantly by LS174T proteases and minimal cleavage of S2 and S3 was observed (FIG. 30B). This proteolysis was abrogated in the presence of Marimastat, an MMP inhibitor. In contrast, none of the substrates were efficiently cleaved by HCT-8 secreted proteases (FIG. 30C).

Figures 19D, 19E:
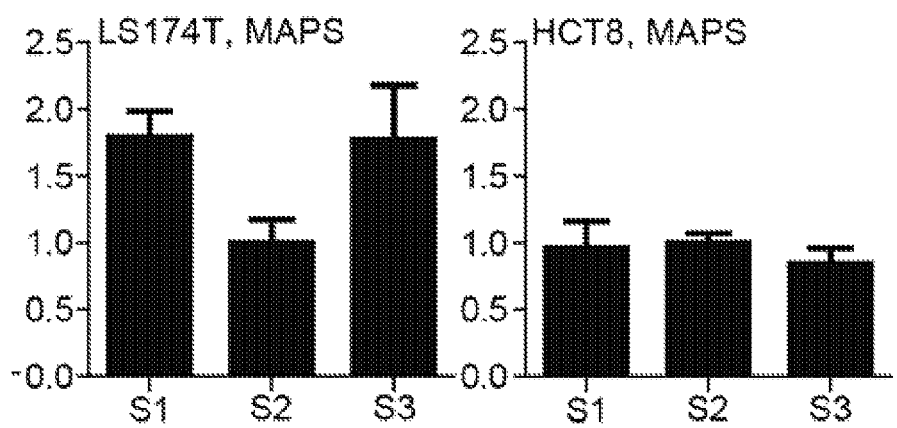
Figure 31A:
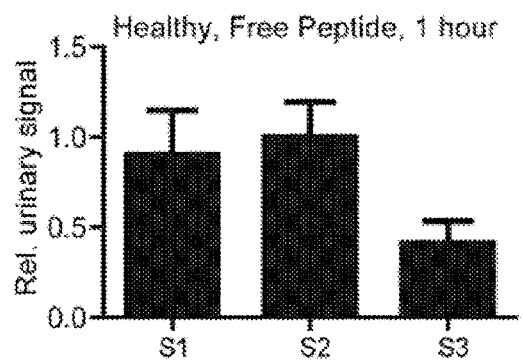
FIGS. 31A-31C show the in vivo performance of unencapsulated S1-3 peptides.
Figure 31B:
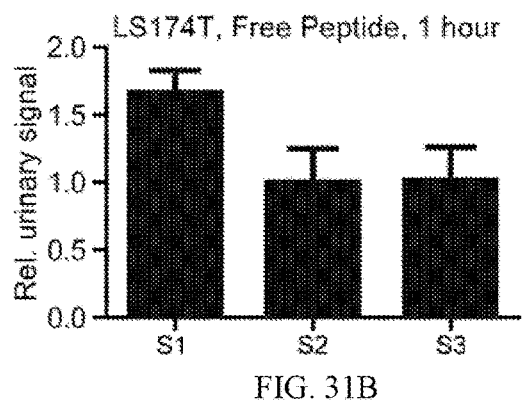
Figure 31C:
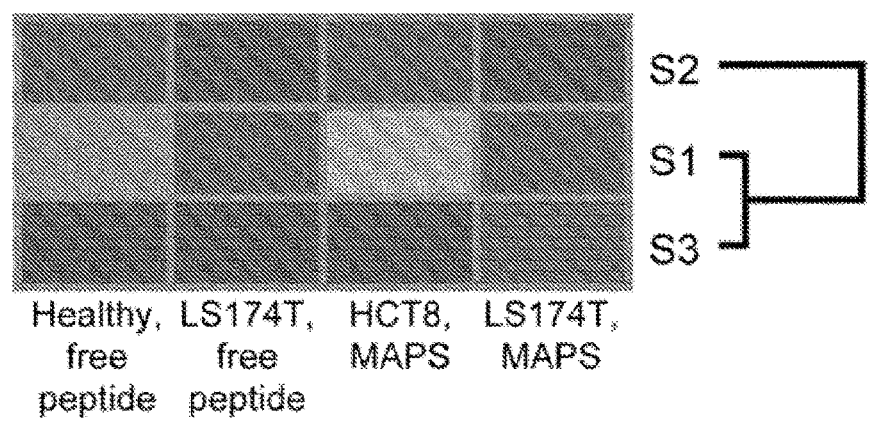

The in vivo activation protocol was applied to specifically activate the three sets of MAPS to profile tumor protease activity between LS174T and HCT8 tumors. In contrast to the in vitro cleavage assay, LS174T mice, MAPS-S1 and MAPS-S3 had higher urinary signal compared to MAPS-S2 (FIG. 19D). This difference highlights the importance of performing these assays in an in vivo setting as previous work has highlighted the biological difference from 2D culture to in vivo. One potential explanation could be that the proteases are not adequately processed from their zymogen form when secreted in vitro. All three constructs generated similar urine signals when tested in HCT8 tumor-bearing mice (FIG. 19E). This is reflective of the lower MMP2, 9 secretion rate, as S1 and S3 respond strongly to MMP2 and 9. Injection of free peptide into healthy mice showed that S3 had the lowest background cleavage, validating its application as a diagnostic protease substrate for cancers with high sensitivity and specificity (FIG. 31A). In contrast to the MAPS signature of LS174T mice, injection of free peptides in tumor-bearing mice, which should primarily sample blood activity (including proteases secreted from the tumor into the blood),[29] showed similar S2 and S3 signals and elevated S1 signal (FIG. 31B). Taken together, hierarchical clustering of urine signal from in vivo experiments shows the need to shield and locally assay protease activity, the capability of MAPS to distinguish protease profiles of two human colon cancer lines with differing protease levels (FIG. 5, FIG. 19F, and FIG. 30).

Example 17: Conclusions

Here, an approach to measure protease activity in vivo with greater specificity using a remotely triggered nanosystem is reported. It was demonstrated that peptides are shielded in thermosensitive liposomes and can be specifically released with application of AMF when co-encapsulated with magnetic nanoparticles. This system is not hindered by optical windows and allows for deep-tissue activation. It was shown that this technique is able to identify differences in MMP profiles across two in vivo human colorectal cancer xenograft models. The urinary reporters employed can be readily multiplexed (e.g. by mass encoding[21]) to enable high-content profiling of tumors. Furthermore, multimodal diagnosis and profiling could be enabled by magnetic resonance imaging for the magnetic nanoparticles within the liposomes. MAPS were primarily applied to profile MMP activity, but this approach is readily applicable to a variety of enzyme systems.

Example 18: Materials and Methods of Examples 9-17

Synthesis of Peptide Substrates and Liposomes

Peptides were synthesized by CPC Scientific, Inc. For full peptide sequence and description see Table 2. Briefly, peptide-reporter tandems are comprised of an N-terminal biotin for depletion, followed by protease substrate, and then D-stereoisomer of Glutamate Fibrinopeptide conjugated to Cy7 for urinary measurements. Liposomes were prepared by applying the lipid-film hydration method with subsequent sequential extrusion. A lipid composition of 11.18 mg of dipalmitoylphosphatidyl-choline (DCCP), 1.31 mg monostearoylphosphatidylcholine (MSPC) and 2.51 mg poly(ethylene glycol)-conjugated distearoylphosphatidylethanolamine, DSCP-PEG-2000, was dissolved in 1.5 mL isopropanol, shortly sonicated and 3 aliquots of each 0.5 mL were dried under gentle nitrogen flow. All components were purchased from Avanti Polar lipids. The formed lipid cakes were then kept at least for 12 hours under vacuum. A volume of 300 µl trizma-based hydration media was prepared and mixed with magnetic nanoparticles (Ocean Nanotech, SHA-25) at a final iron concentration of 2.5 mg/mL and DMSO-based peptide solutions at a concentration of 2 µM. The solution was pre-warmed to 65° C. and added to the liposomal cake which was hydrated for 1 hour at 65° C. in a water bath under continuous agitation. For in vitro release studies, 80 mM calcein was added to the trizma solution instead of peptide substrates. At this concentration, the self-quenching properties of calcein in solution were ensured. After hydration, the liposomes were extruded sequentially using 400, 200 and 100 nm large filter membranes to narrow the size distribution. The solutions were then purified from excess particles and free substrates by gravity column filtration. The resulting size was quantified by dynamic light scattering and peptide and iron concentration were measured by absorbance scans. The final solutions for in vivo injection were equally adjusted to 0.5 µM for peptides S1, S2 and S3 by dilution in PBS.

In Vitro Thermo-Release Studies

Temperature stability and kinetic release profile were measured in a fluorescence plate reader (Tecan) by suspending MAPS samples of 80 µl in 384 well plates. Temperature was set and kept at 37° C. and increased to 43° C. for kinetic release measurements when crossing the melting temperature. Calcein release was determined by measuring the increase of the fluorescence signal for an excitation wavelength of $\lambda_{ex}$=494 nm and emission wavelength $\lambda_{em}$=517 nm.

Magnetic Activation of Thermosensitive Liposomes

Magnetic activation of the liposomes was performed using a custom AMF setup. Two coils were fabricated and specifically designed to fit the requirements for in vitro and in vivo experiments. A toroid composed of a soft ferromagnetic material optimized for high frequency power transformers (Ferroxcube 3F3) was used as coil core. A transformer circuit with a resistive ballast in the primary circuit was used to generate high, stable currents in the secondary while simultaneously matching the impedance of the variable frequency 200 W amplifier (1020L, Electronics & Innovation). In the secondary, the coil acted as the resistive and inductive elements of an RLC resonance circuit, with a high voltage series capacitor setting the resonant frequency. The field magnitude was measured by a custom built probe employing a pickup loop and an oscilloscope. A simple cooling system with circulating ice water was coupled to the coil via silicone tubing and an electric fan was positioned in proximity to the coil. For in vitro release studies and calorimetric measurements of the particles, temperature measurements were conducted using an AMF insensitive fiber optic temperature probe and recorded during AMF exposure. SLP measurements were repeated 3 times and control samples with only water were measured after every 4 trials to determine the background heating rate. All samples were 1 mL with a MNP concentration of approximately 2 mg/mL. The SLP value measured was normalized to the metal content determined by elemental analysis. In vitro release studies were temperature monitored and fluid temperatures did not exceed T=39° C. due to background heating. Measurements were repeated three times and calcein release was evaluated in a multi-well plate fluorescence reader as described above.

In Vitro Recombinant Protease Assays

MMPs (~100 nM working concentration, Enzo Life Sciences) were added to substrates in 384-well plates in activity buffer (50 mM Tris, 150 mM NaCl, 5 mM $CaCl_2$, 1 µM ZnCl2) containing 1% BSA. After one hour, uncleaved peptide was extracted using Dynabeads Strepatividin C1

(Life Technologies) as per manufacturer protocols. An excess of Dynabeads was used.

Cell Culture and Secreted Protease Activity Assay

LS174T and HCT-8 cells were cultured in Eagle's Minimal Essential Medium (ATCC) supplemented with 10% FBS (Gibco) and 1% penicillin-streptomycin (CellGro). Cells were passaged when confluence reached 80%. To isolate secreted proteases, after cells were plated, cells were washed and replaced in serum-free media. Media was collected and MMP2 was measured in supernatant using a Quantikine MMP-2 kit following manufacturer protocols (R&D Systems). Secretion was normalized to number of cells and days in culture. A similar approach was used when collecting supernatants for measuring proteolysis of S1-3.

Pharmacokinetic Studies

Wild-type, female Swiss Webster mice (4-6 wk, Taconic) were infused intravenously via the tail vein with liposomes carrying a near IR dye (VT750, Perkin Elmer). Blood was withdrawn retro-orbitally (~10 µL) and then immediately transferred into 90 µL of PBS with 5 mM EDTA and spun at 1000×g to pellet blood cells. Concentration of liposome was measured using an Odyssey Infrared scanner (Li-Cor Inc.). Nude mice bearing LS174T tumors (see below) were infused with labeled liposomes. Mice were sacrificed at different timepoints, followed by necropsy to remove organs and tumors. Organ accumulation was measured using an Odyssey scanner and quantified using ImageJ (NIH).

In Vivo Cancer Model Studies

Female nude mice (4-6 week, Taconic) were inoculated subcutaneously with $3\times10^6$ LS174T cells and HCT-8 cells on the hind flank and allowed to grow. Two weeks after inoculation, tumor-bearing mice were infused with MAPS. Suspensions were diluted to each 0.5 µM peptide concentration in 200 µl sterile PBS Immediately after infusion, mice were placed in an in-house devised urine collector with a 96 well plate base. Urine was collected and stored at −80° C. For analysis, urine was diluted from 25-fold in PBS. Reporter concentration was quantified by Cy7 fluorescence measurements in the Odyseey Scanner and compared to a ladder (FIG. 30).

Statistics and Data Analysis

All statistical analyses were performed in GraphPad (Prism 5.0). Statistical significance and individual tests are described in figure legends. Heatmaps and hierarchical clusters were generated using GENE-E (Broad Institute). Data were clustered by one minus Pearson correlation.

The foregoing written specification is considered to be sufficient to enable one skilled in the art to practice the methods described by the disclosure. The present disclosure is not limited in scope by the examples provided, since the examples are intended as illustrations of various aspect of the disclosure and other functionally equivalent embodiments are within the scope of the disclosure. Various modifications of the disclosure in addition to those shown and described herein will become apparent to those skilled in the art from the foregoing description and fall within the scope of the appended claims. The advantages and objects of the disclosure are not necessarily encompassed by each embodiment of the methods and compositions described by the disclosure.

All references, patents and patent publications that are recited in this application are incorporated in their entirety herein by reference.

The invention claimed is:

1. A composition comprising:
a biomarker particle, wherein the biomarker particle comprises a carrier domain linked to a detectable marker via an enzyme substrate, wherein:
(a) a photolabile protecting group is positioned at a residue adjacent to an enzyme-target scissile bond in the enzyme substrate; and/or
(b) a liposome encapsulates the carrier domain linked to the detectable marker via the enzyme substrate, wherein the liposome is a thermosensitive liposome, a liposome comprising gold nanoparticles, a pH-responsive liposome, or a reactive oxygen-responsive liposome.

2. The composition of claim 1, wherein the enzyme substrate comprises a cancer substrate.

3. The composition of claim 1, wherein the carrier domain is an iron oxide nanoparticle and the detectable marker comprises fluorescein.

4. The composition of claim 1, wherein the photolabile protecting group is 1-(4,5-dimethoxy-2-nitrophenyl) diazoethane (DMNPE), coumarin, or benoquinolone.

5. The composition of claim 1, wherein the thermosensitive liposome comprises magnetic nanoparticles.

6. The composition of claim 5, wherein the magnetic nanoparticles are at least 25 nm in diameter.

7. The composition of claim 1, wherein the residue is glutamic acid.

8. The composition of claim 1, wherein the biomarker particle comprises the photolabile protecting group.

9. The composition of claim 1 comprising the thermosensitive liposome.

* * * * *

UNITED STATES PATENT AND TRADEMARK OFFICE
CERTIFICATE OF CORRECTION

PATENT NO. : 11,428,689 B2
APPLICATION NO. : 16/099147
DATED : August 30, 2022
INVENTOR(S) : Sangeeta N. Bhatia et al.

It is certified that error appears in the above-identified patent and that said Letters Patent is hereby corrected as shown below:

In the Claims

In Claim 4, at Column 52, Lines 41-43:
"The composition of claim 1, wherein the photolabile protecting group is 1-(4,5-dimethoxy-2-nitrophenyl) diazoethane (DMNPE), coumarin, or benoquinolone."

Should read:
--The composition of claim 1, wherein the photolabile protecting group is 1-(4,5-dimethoxy-2-nitrophenyl) diazoethane (DMNPE), coumarin, or benzoquinolone.--

Signed and Sealed this
Twentieth Day of December, 2022

Katherine Kelly Vidal
*Director of the United States Patent and Trademark Office*

SEQUENCE LISTING

```
<160> NUMBER OF SEQ ID NOS: 15

<210> SEQ ID NO 1
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 1

Glu Gly Val Asn Asp Asn Glu Glu Gly Phe Phe Ser Ala Arg
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (3)..(4)
<223> OTHER INFORMATION: Modified by a scissile bond

<400> SEQUENCE: 2

Pro Leu Gly Leu Glu Glu Ala
1               5

<210> SEQ ID NO 3
<211> LENGTH: 11
<212> TYPE: PRT
<213> ORGANISM: Artificial Sequence
<220> FEATURE:
```

<223> OTHER INFORMATION: Synthetic polypeptide
<220> FEATURE:
<221> NAME/KEY: MISC_FEATURE
<222> LOCATION: (1)..(1)
<223> OTHER INFORMATION: Modifed by FAM
<220> FEATURE:
<221> NAME/KEY: MOD_RES
<222> LOCATION: (1)..(1)
<223> OTHER INFORMATION: D stereoisomer of Ser
<220> FEATURE:
<221> NAME/KEY: MOD_RES
<222> LOCATION: (2)..(2)
<223> OTHER INFORMATION: D stereoisomer of Lys

<400> SEQUENCE: 3

Ser Lys Pro Leu Gly Leu Glu Glu Ala Gly Cys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by Biotin-PEG(5 kDa)-(KFAM)

<400> SEQUENCE: 4

Pro Leu Gly Leu Glu Glu Ala Gly Cys
1               5

<210> SEQ ID NO 5
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: D stereoisomer of Glu
<220> FEATURE:
<221> NAME/KEY: MOD_RES
<222> LOCATION: (3)..(3)
<223> OTHER INFORMATION: D stereoisomer of Val
<220> FEATURE:
<221> NAME/KEY: MOD_RES
<222> LOCATION: (4)..(4)
<223> OTHER INFORMATION: D stereoisomer of Asn
<220> FEATURE:
<221> NAME/KEY: MOD_RES
<222> LOCATION: (5)..(5)
<223> OTHER INFORMATION: D stereoisomer of Asp
<220> FEATURE:
<221> NAME/KEY: MOD_RES
<222> LOCATION: (6)..(6)
<223> OTHER INFORMATION: D stereoisomer of Asn
<220> FEATURE:
<221> NAME/KEY: MOD_RES
<222> LOCATION: (7)..(7)
<223> OTHER INFORMATION: D stereoisomer of Glu
<220> FEATURE:
<221> NAME/KEY: MOD_RES
<222> LOCATION: (8)..(8)
<223> OTHER INFORMATION: D stereoisomer of Glu
<220> FEATURE:
<221> NAME/KEY: MOD_RES
<222> LOCATION: (10)..(10)
<223> OTHER INFORMATION: D stereoisomer of Phe
<220> FEATURE:
<221> NAME/KEY: MOD_RES
<222> LOCATION: (11)..(11)
<223> OTHER INFORMATION: D stereoisomer of Phe

```
<220> FEATURE:
<221> NAME/KEY: MOD_RES
<222> LOCATION: (12)..(12)
<223> OTHER INFORMATION: D stereoisomer of Ser
<220> FEATURE:
<221> NAME/KEY: MOD_RES
<222> LOCATION: (13)..(13)
<223> OTHER INFORMATION: D stereoisomer of Ala
<220> FEATURE:
<221> NAME/KEY: MOD_RES
<222> LOCATION: (14)..(14)
<223> OTHER INFORMATION: D stereoisomer of Arg
<220> FEATURE:
<221> NAME/KEY: MOD_RES
<222> LOCATION: (16)..(16)
<223> OTHER INFORMATION: D stereoisomer of Ser

<400> SEQUENCE: 5

Glu Gly Val Asn Asp Asn Glu Glu Gly Phe Phe Ser Ala Arg Lys Ser
1               5                   10                  15

Arg Leu Val Gly Glu Gly Cys
            20

<210> SEQ ID NO 6
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by Biotin
<220> FEATURE:
<221> NAME/KEY: MISC_FEATURE
<222> LOCATION: (9)..(10)
<223> OTHER INFORMATION: Modified by Cy7
<220> FEATURE:
<221> NAME/KEY: MOD_RES
<222> LOCATION: (10)..(10)
<223> OTHER INFORMATION: D stereoisomer of Glu
<220> FEATURE:
<221> NAME/KEY: MOD_RES
<222> LOCATION: (12)..(12)
<223> OTHER INFORMATION: D stereoisomer of Val
<220> FEATURE:
<221> NAME/KEY: MOD_RES
<222> LOCATION: (13)..(13)
<223> OTHER INFORMATION: D stereoisomer of Asn
<220> FEATURE:
<221> NAME/KEY: MOD_RES
<222> LOCATION: (14)..(14)
<223> OTHER INFORMATION: D stereoisomer of Asp
<220> FEATURE:
<221> NAME/KEY: MOD_RES
<222> LOCATION: (15)..(15)
<223> OTHER INFORMATION: D stereoisomer of Asn
<220> FEATURE:
<221> NAME/KEY: MOD_RES
<222> LOCATION: (16)..(16)
<223> OTHER INFORMATION: D stereoisomer of Glu
<220> FEATURE:
<221> NAME/KEY: MOD_RES
<222> LOCATION: (17)..(17)
<223> OTHER INFORMATION: D stereoisomer of Glu
<220> FEATURE:
<221> NAME/KEY: MOD_RES
<222> LOCATION: (19)..(19)
<223> OTHER INFORMATION: D stereoisomer of Phe
<220> FEATURE:
<221> NAME/KEY: MOD_RES
<222> LOCATION: (20)..(20)
<223> OTHER INFORMATION: D stereoisomer of Phe
<220> FEATURE:
<221> NAME/KEY: MOD_RES
<222> LOCATION: (21)..(21)
```

```
<223> OTHER INFORMATION: D stereoisomer of Ser
<220> FEATURE:
<221> NAME/KEY: MOD_RES
<222> LOCATION: (22)..(22)
<223> OTHER INFORMATION: D stereoisomer of Ala
<220> FEATURE:
<221> NAME/KEY: MOD_RES
<222> LOCATION: (23)..(23)
<223> OTHER INFORMATION: D stereoisomer of Arg
<220> FEATURE:
<221> NAME/KEY: MISC_FEATURE
<222> LOCATION: (23)..(23)
<223> OTHER INFORMATION: Modified by NH2

<400> SEQUENCE: 6

Cys Gly Pro Val Gly Leu Ile Gly Lys Glu Gly Val Asn Asp Asn Glu
1               5                   10                  15

Glu Gly Phe Phe Ser Ala Arg
            20

<210> SEQ ID NO 7
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by Biotin
<220> FEATURE:
<221> NAME/KEY: MISC_FEATURE
<222> LOCATION: (11)..(12)
<223> OTHER INFORMATION: Modified by Cy7
<220> FEATURE:
<221> NAME/KEY: MOD_RES
<222> LOCATION: (12)..(12)
<223> OTHER INFORMATION: D stereoisomer of Glu
<220> FEATURE:
<221> NAME/KEY: MOD_RES
<222> LOCATION: (14)..(14)
<223> OTHER INFORMATION: D stereoisomer of Val
<220> FEATURE:
<221> NAME/KEY: MOD_RES
<222> LOCATION: (15)..(15)
<223> OTHER INFORMATION: D stereoisomer of Asn
<220> FEATURE:
<221> NAME/KEY: MOD_RES
<222> LOCATION: (16)..(16)
<223> OTHER INFORMATION: D stereoisomer of Asp
<220> FEATURE:
<221> NAME/KEY: MOD_RES
<222> LOCATION: (17)..(17)
<223> OTHER INFORMATION: D stereoisomer of Asn
<220> FEATURE:
<221> NAME/KEY: MOD_RES
<222> LOCATION: (18)..(18)
<223> OTHER INFORMATION: D stereoisomer of Glu
<220> FEATURE:
<221> NAME/KEY: MOD_RES
<222> LOCATION: (19)..(19)
<223> OTHER INFORMATION: D stereoisomer of Glu
<220> FEATURE:
<221> NAME/KEY: MOD_RES
<222> LOCATION: (21)..(21)
<223> OTHER INFORMATION: D stereoisomer of Phe
<220> FEATURE:
<221> NAME/KEY: MOD_RES
<222> LOCATION: (22)..(22)
<223> OTHER INFORMATION: D stereoisomer of Phe
<220> FEATURE:
<221> NAME/KEY: MOD_RES
<222> LOCATION: (23)..(23)
<223> OTHER INFORMATION: D stereoisomer of Ser
<220> FEATURE:
<221> NAME/KEY: MOD_RES
```

```
<222> LOCATION: (24)..(24)
<223> OTHER INFORMATION: D stereoisomer of Ala
<220> FEATURE:
<221> NAME/KEY: MOD_RES
<222> LOCATION: (25)..(25)
<223> OTHER INFORMATION: D stereoisomer of Arg
<220> FEATURE:
<221> NAME/KEY: MISC_FEATURE
<222> LOCATION: (25)..(25)
<223> OTHER INFORMATION: Modified by NH2

<400> SEQUENCE: 7

Cys Gly Pro Val Pro Leu Ser Leu Val Met Lys Glu Gly Val Asn Asp
1               5                   10                  15

Asn Glu Glu Gly Phe Phe Ser Ala Arg
            20                  25

<210> SEQ ID NO 8
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by Biotin
<220> FEATURE:
<221> NAME/KEY: MISC_FEATURE
<222> LOCATION: (10)..(11)
<223> OTHER INFORMATION: Modified by Cy7
<220> FEATURE:
<221> NAME/KEY: MOD_RES
<222> LOCATION: (11)..(11)
<223> OTHER INFORMATION: D stereoisomer of Glu
<220> FEATURE:
<221> NAME/KEY: MOD_RES
<222> LOCATION: (13)..(13)
<223> OTHER INFORMATION: D stereoisomer of Val
<220> FEATURE:
<221> NAME/KEY: MOD_RES
<222> LOCATION: (14)..(14)
<223> OTHER INFORMATION: D stereoisomer of Asn
<220> FEATURE:
<221> NAME/KEY: MOD_RES
<222> LOCATION: (15)..(15)
<223> OTHER INFORMATION: D stereoisomer of Asp
<220> FEATURE:
<221> NAME/KEY: MOD_RES
<222> LOCATION: (16)..(16)
<223> OTHER INFORMATION: D stereoisomer of Asn
<220> FEATURE:
<221> NAME/KEY: MOD_RES
<222> LOCATION: (17)..(17)
<223> OTHER INFORMATION: D stereoisomer of Glu
<220> FEATURE:
<221> NAME/KEY: MOD_RES
<222> LOCATION: (18)..(18)
<223> OTHER INFORMATION: D stereoisomer of Glu
<220> FEATURE:
<221> NAME/KEY: MOD_RES
<222> LOCATION: (20)..(20)
<223> OTHER INFORMATION: D stereoisomer of Phe
<220> FEATURE:
<221> NAME/KEY: MOD_RES
<222> LOCATION: (21)..(21)
<223> OTHER INFORMATION: D stereoisomer of Phe
<220> FEATURE:
<221> NAME/KEY: MOD_RES
<222> LOCATION: (22)..(22)
<223> OTHER INFORMATION: D stereoisomer of Ser
<220> FEATURE:
<221> NAME/KEY: MOD_RES
<222> LOCATION: (23)..(23)
<223> OTHER INFORMATION: D stereoisomer of Ala
<220> FEATURE:
```

```
<221> NAME/KEY: MOD_RES
<222> LOCATION: (24)..(24)
<223> OTHER INFORMATION: D stereoisomer of Arg
<220> FEATURE:
<221> NAME/KEY: MISC_FEATURE
<222> LOCATION: (24)..(24)
<223> OTHER INFORMATION: Modified by NH2

<400> SEQUENCE: 8

Cys Gly Pro Leu Gly Val Arg Gly Lys Lys Glu Gly Val Asn Asp Asn
1               5                   10                  15

Glu Glu Gly Phe Phe Ser Ala Arg
            20

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by a Reporter
<220> FEATURE:
<221> NAME/KEY: MISC_FEATURE
<222> LOCATION: (3)..(4)
<223> OTHER INFORMATION: Modified by a scissile bond
<220> FEATURE:
<221> NAME/KEY: MISC_FEATURE
<222> LOCATION: (5)..(6)
<223> OTHER INFORMATION: Modified by DMNPE
<220> FEATURE:
<221> NAME/KEY: MISC_FEATURE
<222> LOCATION: (9)..(9)
<223> OTHER INFORMATION: Modified by NP

<400> SEQUENCE: 9

Pro Leu Gly Leu Glu Glu Ala Gly Cys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(6)
<223> OTHER INFORMATION: Modified by NP

<400> SEQUENCE: 10

Leu Glu Glu Ala Gly Cys
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by FAM
<220> FEATURE:
<221> NAME/KEY: MOD_RES
<222> LOCATION: (1)..(1)
<223> OTHER INFORMATION: D stereoisomer of Ser
<220> FEATURE:
<221> NAME/KEY: MOD_RES
```

<222> LOCATION: (2)..(2)
<223> OTHER INFORMATION: D stereoisomer of Lys

<400> SEQUENCE: 11

Ser Lys Pro Leu Gly
1               5

<210> SEQ ID NO 12
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by 5-carboxy-fluorescein
<220> FEATURE:
<221> NAME/KEY: MOD_RES
<222> LOCATION: (1)..(1)
<223> OTHER INFORMATION: D stereoisomer of Ser
<220> FEATURE:
<221> NAME/KEY: MOD_RES
<222> LOCATION: (2)..(2)
<223> OTHER INFORMATION: D stereoisomer of Lys
<220> FEATURE:
<221> NAME/KEY: MISC_FEATURE
<222> LOCATION: (11)..(11)
<223> OTHER INFORMATION: Modified by an Iron oxide nanoparticle

<400> SEQUENCE: 12

Ser Lys Pro Leu Gly Leu Glu Glu Ala Gly Cys
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by Biotin-PEG and Lys-5-carboxy-
      fluorescein
<220> FEATURE:
<221> NAME/KEY: MISC_FEATURE
<222> LOCATION: (9)..(9)
<223> OTHER INFORMATION: Modified by NP

<400> SEQUENCE: 13

Pro Leu Gly Leu Glu Glu Ala Gly Cys
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Modified by FAM
<220> FEATURE:
<221> NAME/KEY: MOD_RES
<222> LOCATION: (1)..(1)
<223> OTHER INFORMATION: D stereoisomer of Ser
<220> FEATURE:
<221> NAME/KEY: MOD_RES
<222> LOCATION: (2)..(2)
<223> OTHER INFORMATION: D stereoisomer of Lys
<220> FEATURE:

```
<221> NAME/KEY: MOD_RES
<222> LOCATION: (3)..(3)
<223> OTHER INFORMATION: D stereoisomer of Pro
<220> FEATURE:
<221> NAME/KEY: MOD_RES
<222> LOCATION: (4)..(4)
<223> OTHER INFORMATION: D stereoisomer of Leu
<220> FEATURE:
<221> NAME/KEY: MOD_RES
<222> LOCATION: (6)..(6)
<223> OTHER INFORMATION: D stereoisomer of Leu
<220> FEATURE:
<221> NAME/KEY: MOD_RES
<222> LOCATION: (7)..(7)
<223> OTHER INFORMATION: D stereoisomer of Glu
<220> FEATURE:
<221> NAME/KEY: MOD_RES
<222> LOCATION: (8)..(8)
<223> OTHER INFORMATION: D stereoisomer of Glu
<220> FEATURE:
<221> NAME/KEY: MOD_RES
<222> LOCATION: (9)..(9)
<223> OTHER INFORMATION: D stereoisomer of Ala

<400> SEQUENCE: 14

Ser Lys Pro Leu Gly Leu Glu Glu Ala Gly Cys
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 15

Arg Leu Val Gly Glu Gly Cys
1               5
```